(12) United States Patent
Lim et al.

(10) Patent No.: US 11,624,342 B2
(45) Date of Patent: *Apr. 11, 2023

(54) RECONFIGURABLE SURGICAL FRAME AND METHOD FOR USE THEREOF

(71) Applicant: Warsaw Orthopedic, Inc., Warsaw, IN (US)

(72) Inventors: Roy K. Lim, Germantown, TN (US); Richard A. Hynes, Melbourne Beach, FL (US); Matthew M. Morrison, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 65 days.

This patent is subject to a terminal disclaimer.

(21) Appl. No.: 17/157,016

(22) Filed: Jan. 25, 2021

(65) Prior Publication Data

US 2021/0140395 A1 May 13, 2021

Related U.S. Application Data

(63) Continuation of application No. 16/108,892, filed on Aug. 22, 2018, now Pat. No. 10,900,448.

(51) Int. Cl.
*A61G 13/04* (2006.01)
*A61G 13/08* (2006.01)
(Continued)

(52) U.S. Cl.
CPC ........... *F02M 31/183* (2013.01); *A61G 13/04* (2013.01); *A61G 13/08* (2013.01); *F02M 31/087* (2013.01);
(Continued)

(58) Field of Classification Search
CPC .... A61G 13/08; A61G 13/04; A61G 13/0054; A61G 13/104; A61G 13/121; A61G 13/122; A61G 13/123
See application file for complete search history.

(56) References Cited

U.S. PATENT DOCUMENTS 2,691,979 A 10/1954 Watson
3,060,925 A 10/1962 Honsaker et al.
(Continued)

FOREIGN PATENT DOCUMENTS

CN 2100875 U 4/1992
CN 201185976 1/2009
(Continued)

OTHER PUBLICATIONS

Office Action and Search Report dated Aug. 27, 2019 for corresponding Chinese application No. 201680046857.4.
(Continued)

*Primary Examiner* — David R Hare
*Assistant Examiner* — Adam C Ortiz

(57) ABSTRACT

A surgical frame and method for use thereof is provided. The surgical frame is capable of reconfiguration before, during, or after surgery. The surgical frame includes a main beam that can be rotated, raised/lowered, and tilted upwardly/downwardly to afford positioning and repositioning of a patient supported thereon. The main beam is capable of be reconfigured between a left configuration and a right configuration to support the patient in different positions thereon.

20 Claims, 74 Drawing Sheets

(51) Int. Cl.

| | |
|---|---|
| *A61B 34/30* | (2016.01) |
| *A61G 13/00* | (2006.01) |
| *A61G 13/12* | (2006.01) |
| *F02M 31/18* | (2006.01) |
| *F02M 31/08* | (2006.01) |
| *F02M 31/087* | (2006.01) |
| *F02M 31/135* | (2006.01) |

(52) U.S. Cl.
CPC ...... *F02M 31/0825* (2013.01); *F02M 31/135* (2013.01); *A61B 34/30* (2016.02); *A61B 2034/304* (2016.02); *A61G 13/0054* (2016.11); *A61G 13/121* (2013.01); *A61G 13/122* (2013.01); *A61G 13/123* (2013.01)

(56) References Cited

U.S. PATENT DOCUMENTS

| | | |
|---|---|---|
| 3,227,440 A | 1/1966 | Scott |
| 3,293,667 A | 12/1966 | Ohrberg |
| 3,306,287 A | 2/1967 | Arp |
| 3,389,702 A | 6/1968 | Kennedy |
| 3,828,377 A | 8/1974 | Fary, Sr. |
| 4,029,089 A | 6/1977 | Mulhlland |
| 4,655,200 A | 4/1987 | Knight |
| 4,705,026 A | 11/1987 | Chaussy |
| 4,866,796 A | 9/1989 | Robinson |
| 4,872,656 A | 10/1989 | Brendgord |
| 4,901,384 A | 2/1990 | Eary |
| 4,915,101 A | 4/1990 | Cuccia |
| 5,009,407 A | 4/1991 | Watanabe |
| 5,088,706 A | 2/1992 | Jackson |
| 5,103,511 A | 4/1992 | Sequin |
| 5,131,106 A | 7/1992 | Jackson |
| 5,362,302 A | 11/1994 | Jenson et al. |
| 5,390,383 A | 2/1995 | Carn |
| 5,410,769 A | 5/1995 | Waterman |
| 5,444,882 A | 8/1995 | Andrews |
| 5,613,254 A | 3/1997 | Clayman |
| 5,642,302 A | 6/1997 | Dumont |
| 5,860,899 A | 1/1999 | Rassman |
| 5,991,651 A | 11/1999 | LaBarbera |
| 6,003,176 A | 12/1999 | Wasley |
| 6,076,525 A | 6/2000 | Hoffman |
| 6,112,349 A | 9/2000 | Connolly |
| 6,154,901 A | 12/2000 | Carr |
| 6,260,220 B1 | 7/2001 | Lamb |
| 6,295,671 B1 | 10/2001 | Reesby et al. |
| 6,311,349 B1 | 11/2001 | Kazakia |
| 6,367,104 B1 | 4/2002 | Fallbo, Sr. et al. |
| 6,378,149 B1 | 4/2002 | Sanders et al. |
| 6,516,483 B1 | 2/2003 | VanSteenburg |
| 6,566,833 B2 | 5/2003 | Barlett |
| 6,615,430 B2 | 9/2003 | Heimbrock |
| 6,671,905 B2 | 1/2004 | Bartlett et al. |
| 6,681,423 B2 | 1/2004 | Zachrisson |
| 6,701,553 B1 | 3/2004 | Hand et al. |
| 6,701,554 B2 | 3/2004 | Heimbrock |
| 6,701,558 B2 | 3/2004 | VanSteenburg |
| 6,715,169 B2 | 4/2004 | Niederkrom |
| 6,728,983 B2 | 5/2004 | Bartlett et al. |
| 6,732,390 B2 | 5/2004 | Krywiczanin |
| 6,739,006 B2 | 5/2004 | Borders et al. |
| 6,820,621 B2 | 11/2004 | DeMayo |
| 6,874,181 B1 | 4/2005 | Connolly et al. |
| 6,934,986 B2 | 8/2005 | Krywiczanin et al. |
| 6,941,951 B2 | 9/2005 | Hubert et al. |
| 6,966,081 B1 | 11/2005 | Sharps |
| 7,100,225 B1 | 9/2006 | Bailey |
| 7,189,214 B1 | 3/2007 | Saunders |
| 7,219,379 B2 | 5/2007 | Krywiczanin et al. |
| 7,234,180 B2 | 6/2007 | Horton et al. |
| 7,290,302 B2 | 11/2007 | Sharps |
| 7,426,930 B1 | 9/2008 | Bailey |
| 7,472,440 B2 | 1/2009 | Bartlett et al. |
| 7,484,253 B1 | 2/2009 | Coppens |
| 7,496,980 B2 | 3/2009 | Sharps |
| 7,600,281 B2 | 10/2009 | Skripps |
| 7,669,262 B2 | 3/2010 | Skripps |
| 7,739,762 B2 | 6/2010 | Lamb et al. |
| 7,882,583 B2 | 2/2011 | Skripps |
| 8,118,029 B2 | 2/2012 | Gneiting et al. |
| 8,286,283 B2 | 10/2012 | Copeland et al. |
| 8,286,637 B2 | 10/2012 | Kaska |
| 8,413,660 B2 | 4/2013 | Weinstein et al. |
| 8,439,948 B1 | 5/2013 | King |
| 8,443,473 B2 | 5/2013 | Maxwell |
| 8,584,281 B2 | 11/2013 | Diel et al. |
| 8,635,725 B2 | 1/2014 | Tannoury et al. |
| 9,072,646 B2 | 7/2015 | Skripps et al. |
| 9,265,680 B2 | 2/2016 | Sharps |
| 9,339,430 B2 | 5/2016 | Jackson et al. |
| 9,358,170 B2 | 6/2016 | Jackson |
| 9,414,982 B2 | 8/2016 | Jackson |
| 9,498,397 B2 | 11/2016 | Hight et al. |
| 9,522,078 B2 | 12/2016 | Pizzini |
| 9,554,959 B2 | 1/2017 | Carn |
| 9,655,793 B2 | 5/2017 | Hertz |
| 9,700,476 B2 | 7/2017 | Hoel et al. |
| 9,713,562 B2 | 7/2017 | Perlman et al. |
| 9,744,089 B2 | 8/2017 | Jackson |
| 9,937,006 B2 | 4/2018 | Skripps et al. |
| 9,993,380 B2 | 6/2018 | Jackson |
| 10,136,863 B2 | 11/2018 | Kaiser et al. |
| 10,314,758 B2 | 6/2019 | Dolliver et al. |
| 10,342,722 B2 | 7/2019 | Garrido |
| 10,406,054 B1 | 9/2019 | Scholl et al. |
| 10,426,684 B2 | 10/2019 | Dubois et al. |
| 10,543,142 B2 | 1/2020 | Lim et al. |
| 10,548,796 B2 | 2/2020 | Lim et al. |
| 10,576,006 B2 | 3/2020 | Lim et al. |
| 10,695,252 B2 | 6/2020 | Jackson |
| 10,722,413 B2 | 7/2020 | Lim et al. |
| 10,729,607 B2 | 8/2020 | Jackson |
| 10,751,240 B2 | 8/2020 | Lim et al. |
| 10,835,438 B2 | 11/2020 | Jackson |
| 10,835,439 B2 | 11/2020 | Lim et al. |
| 10,849,809 B2 | 12/2020 | Lim et al. |
| 10,874,570 B2 | 12/2020 | Lim et al. |
| 10,881,570 B2 | 1/2021 | Lim et al. |
| 10,888,484 B2 | 1/2021 | Lim et al. |
| 10,893,996 B2 | 1/2021 | Lim et al. |
| 10,898,401 B2 | 1/2021 | Lim et al. |
| 10,900,448 B2 | 1/2021 | Lim et al. |
| 2002/0138905 A1 | 10/2002 | Barltett et al. |
| 2002/0138906 A1 | 10/2002 | Barltett et al. |
| 2002/0157186 A1 | 10/2002 | VanSteenburg |
| 2003/0140419 A1 | 7/2003 | Barltett et al. |
| 2003/0140420 A1 | 7/2003 | Niederkrom |
| 2003/0145382 A1 | 8/2003 | Krywiczanin |
| 2003/0178027 A1 | 9/2003 | DeMayo et al. |
| 2004/0010849 A1 | 1/2004 | Krywiczanin et al. |
| 2004/0133983 A1 | 7/2004 | Newkirk |
| 2005/0181917 A1 | 8/2005 | Dayal |
| 2006/0037141 A1 | 2/2006 | Krywiczanin et al. |
| 2006/0123546 A1 | 6/2006 | Horton |
| 2006/0162076 A1 | 7/2006 | Bartlett et al. |
| 2006/0162084 A1 | 7/2006 | Mezue |
| 2008/0034502 A1 | 2/2008 | Copeland et al. |
| 2008/0134434 A1 | 6/2008 | Celauro |
| 2008/0222811 A1 | 9/2008 | Gilbert et al. |
| 2009/0139030 A1 | 6/2009 | Yang |
| 2010/0037397 A1 | 2/2010 | Wood |
| 2010/0192300 A1 | 8/2010 | Tannoury |
| 2010/0293719 A1 | 11/2010 | Klemm et al. |
| 2011/0099716 A1 | 5/2011 | Jackson |
| 2012/0103344 A1 | 5/2012 | Hunter |
| 2012/0144589 A1 | 6/2012 | Skripps et al. |
| 2012/0255122 A1 | 10/2012 | Diel et al. |
| 2013/0111666 A1 | 5/2013 | Jackson |
| 2013/0191994 A1 | 8/2013 | Bellows et al. |
| 2013/0283526 A1 | 10/2013 | Gagliardi |
| 2013/0307298 A1 | 11/2013 | Meiki |
| 2014/0059773 A1 | 3/2014 | Carn |

(56) References Cited

U.S. PATENT DOCUMENTS

| | | |
|---|---|---|
| 2014/0068861 A1 | 3/2014 | Jackson |
| 2014/0109316 A1 | 4/2014 | Jackson et al. |
| 2014/0137327 A1 | 5/2014 | Tannoury et al. |
| 2015/0044956 A1 | 2/2015 | Hacker |
| 2015/0245971 A1 | 9/2015 | Bernardoni et al. |
| 2015/0272681 A1 | 10/2015 | Skripps et al. |
| 2016/0000621 A1 | 1/2016 | Jackson |
| 2016/0081582 A1 | 3/2016 | Rapoport |
| 2016/0089287 A1 | 3/2016 | Buerstner |
| 2016/0193099 A1 | 7/2016 | Drake |
| 2017/0027797 A1 | 2/2017 | Dolliver et al. |
| 2017/0049651 A1 * | 2/2017 | Lim .................. A61G 13/123 |
| 2017/0049653 A1 | 2/2017 | Lim |
| 2017/0079864 A1 | 3/2017 | Riley |
| 2017/0112698 A1 | 4/2017 | Hight et al. |
| 2017/0135891 A1 | 5/2017 | Kettner |
| 2017/0151115 A1 | 6/2017 | Jackson |
| 2017/0341232 A1 | 11/2017 | Perplies |
| 2017/0348171 A1 | 12/2017 | Jackson |
| 2018/0116891 A1 | 5/2018 | Beale et al. |
| 2018/0185228 A1 | 7/2018 | Catacchio et al. |
| 2018/0193104 A1 | 7/2018 | Beale et al. |
| 2018/0363596 A1 | 12/2018 | Lim et al. |
| 2019/0000702 A1 | 1/2019 | Lim et al. |
| 2019/0000707 A1 | 1/2019 | Lim et al. |
| 2019/0046381 A1 | 2/2019 | Lim et al. |
| 2019/0046383 A1 | 2/2019 | Lim et al. |
| 2019/0209409 A1 | 7/2019 | Jackson et al. |
| 2020/0000668 A1 | 1/2020 | Lim et al. |
| 2020/0060913 A1 | 2/2020 | Lim et al. |
| 2020/0060914 A1 | 2/2020 | Lim et al. |
| 2020/0060915 A1 | 2/2020 | Lim et al. |
| 2020/0138660 A1 | 5/2020 | Jackson |
| 2020/0170868 A1 | 6/2020 | Jackson |
| 2020/0188208 A1 | 6/2020 | Lim et al. |
| 2020/0138659 A1 | 7/2020 | Lim et al. |
| 2020/0281788 A1 | 9/2020 | Lim et al. |
| 2020/0297568 A1 | 9/2020 | Lim et al. |
| 2020/0337923 A1 | 10/2020 | Lim et al. |
| 2020/0337926 A1 | 10/2020 | Lim et al. |
| 2020/0337927 A1 | 10/2020 | Lim et al. |
| 2020/0360214 A1 | 11/2020 | Lim et al. |

FOREIGN PATENT DOCUMENTS

| | | |
|---|---|---|
| CN | 103298440 | 9/2013 |
| JP | 2012-228509 | 11/2012 |
| JP | 5237301 | 7/2013 |
| JP | 2017113528 | 6/2017 |
| JP | 2018069048 | 5/2018 |
| WO | 2000062731 | 10/2000 |
| WO | 2007058673 | 5/2007 |
| WO | 2017031225 | 2/2017 |
| WO | 2017139548 | 8/2017 |

OTHER PUBLICATIONS

Office Action dated Dec. 17, 2019 for corresponding Japanese Application No. 2018-504646 with English translation.
International Search Report dated Nov. 21, 2016 from International Application No. PCT/US2016/047394.
International Search Report and Written Opinion dated Dec. 4, 2019 from International Application No. PCT/US2019/046979.
Extended European Search Report dated May 4, 2022 for EP Application No. 19851276.6.

* cited by examiner

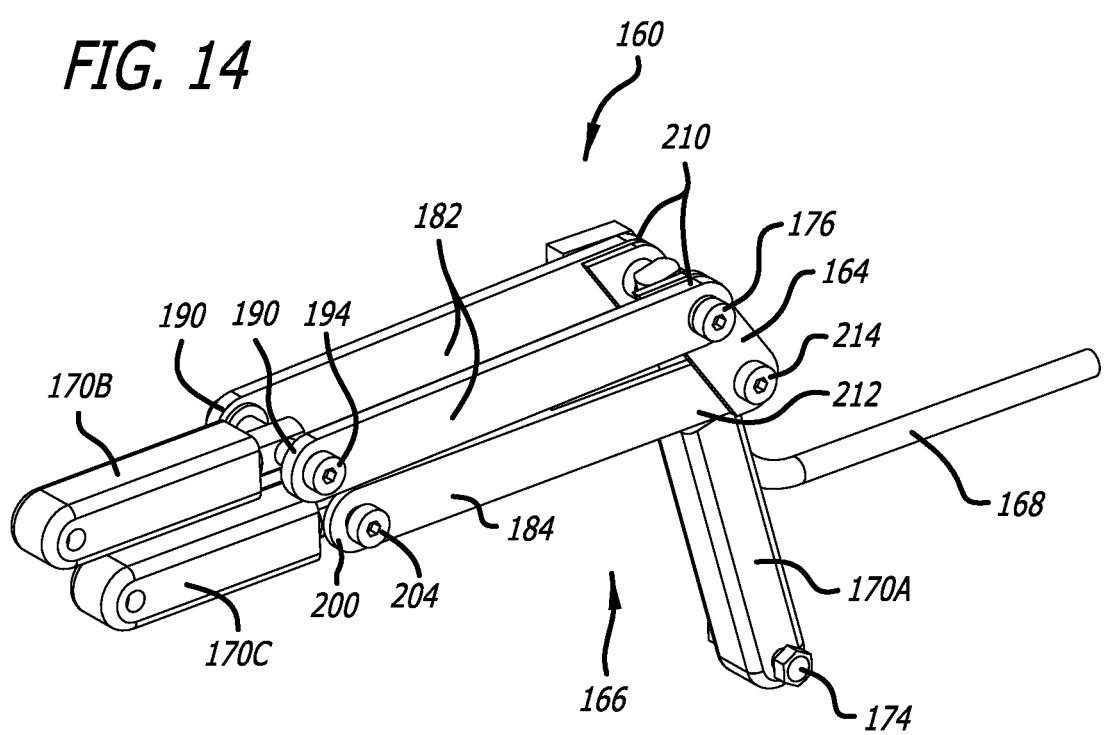

RECONFIGURABLE SURGICAL FRAME AND METHOD FOR USE THEREOF

RELATED APPLICATIONS

The present application is a continuation of U.S. application Ser. No. 16/108,892, filed Aug. 22, 2018; all of which is incorporated by reference herein.

FIELD

The present technology is generally related to a surgical frame and a method for use thereof incorporating a main beam convertible between a left configuration and a right configuration.

BACKGROUND

Access to a patient is of paramount concern during surgery. Surgical frames have been used to position and reposition patients during surgery. For example, surgical frames have been configured to manipulate the rotational position of the patient before, during, and even after surgery. Such surgical frames include support structures to facilitate the rotational movement of the patient. Typical support structures can include main beams supported at either ends thereof for rotational movement about axes of rotation extending along the lengths of the surgical frames. The main beams can be positioned and repositioned to afford various positions of the patients positioned thereon. To illustrate, the main beams can be rotated for positioning a patient in prone positions, lateral positions, and positions 45° between the prone and lateral positions. To facilitate such positioning and repositioning, the main beams have been structured for supporting the patient during such movement. However, typical main beams are structured to afford unfettered access to only one lateral side of the patient. That is, at least portions of typical main beams are structured to always be positioned adjacent one lateral side of the patient. Therefore, there is a need for a main beam that can be reconfigured between a left configuration and a right configuration to afford greater access to a left lateral side and a right lateral side, respectively, of the patient as needed by the type of surgery or preferred by the surgeon.

SUMMARY

The techniques of this disclosure generally relate to a surgical frame and a method for use thereto that incorporates a convertible main beam reconfigurable between a left configuration and a right configuration.

In one aspect, the present disclosure provides a positioning frame for supporting a patient being reconfigurable between a left configuration and a right configuration, the positioning frame including a main beam having a first end, a second end, and a length extending between the first and second end, the main beam defining an axis of rotation relative to a first vertical support portion and a second vertical support portion, the main beam being rotatable about the axis of rotation between at least a first position and a second position, the axis of rotation substantially corresponding to a cranial-caudal axis of the patient when the patient is supported on the positioning frame, the main beam including a first portion at the first end rotatably interconnected relative to a first portion attached to the first vertical support portion, a second portion at the second end rotatably interconnected relative to a first portion attached to the second vertical support portion, and an elongated portion extending between the first portion and the second portion, the first portion of the main beam being rotatably adjustable between a first fixed position and a second fixed position relative to a second portion attached to the first vertical support portion, and a first end of the elongated portion of the main beam being rotatably adjustable between a first fixed position and a second fixed position relative to the first portion of the main beam and a second end of the elongated portion of the main beam being rotatably adjustable between a first fixed position and a second fixed position relative to the second portion of the main beam; a chest support and at least one leg support being moveably attached to the elongated portion of the main beam, the chest support and the at least one leg support each being moveable between a first location on a first side of the elongated portion of the main beam and a second location on a second side of the elongated portion of the main beam; and the first vertical support portion and the second vertical support portion supporting the main beam, the first support portion and the second vertical support portion spacing the main beam from the ground; where, when the first portion of the main beam is in the first fixed position thereof, the first end of the elongated portion of the main beam is in the first fixed position thereof, the second end of the elongated portion of the main beam is in the first fixed position thereof, and the chest support and the at least one leg support are in the first location thereof, the positioning frame is capable of supporting the patient in the left configuration to provide greater access to a left lateral side of the patient, and when the first portion of the main beam is in the second fixed position thereof, the first end of the elongated portion of the main beam is in the second fixed position thereof, the second end of the elongated portion of the main beam is in the second fixed portion thereof, and the chest support and the at least one leg support are in the second position thereof, the positioning frame is capable of supporting the patient in the right configuration to provide greater access to a right lateral side of the patient.

In another aspect, the disclosure provides a positioning frame for supporting a patient being reconfigurable between a left configuration and a right configuration, the positioning frame including a first vertical support portion and a second vertical support portion being spaced apart from one another, the first vertical support portion being positioned at or adjacent a first end of the positioning frame, and the second vertical support portion being positioned at or adjacent a second end of the positioning frame; a main beam having a first end, a second end, and a length extending between the first and second end, the main beam defining an axis of rotation relative to the first vertical support portion and the second vertical support portion, the main beam including a first portion at the first end rotatably interconnected to the first vertical support portion, a second portion at the second end rotatably interconnected to the second vertical support portion, and an elongated portion extending between the first portion and the second portion, the first portion of the main beam being rotatably adjustable between a first fixed position and a second fixed position relative to a second portion attached to the first vertical support portion, and a first end of the elongated portion of the main beam being rotatably adjustable between a first fixed position and a second fixed position relative to the first portion of the main beam and a second end of the elongated portion of the main beam being rotatably adjustable between a first fixed position and a second fixed position relative to the second portion of the main between; and at least one patient support moveably attached to the elongated portion of the main beam, the at least one patient support being moveable between a first location on a first side of the elongated portion of the main beam and a second location on a second side of the elongated portion of the main beam; where, when the first portion of the main beam is in the first fixed position thereof, the first end of the elongated portion of the main beam is in the first fixed position thereof, the second end of the elongated portion of the main beam is in the first fixed position thereof, and the at least one patient support is in the first location thereof, the positioning frame is capable of supporting the patient in the left configuration to provide greater access to a left lateral side of the patient, and when the first portion of the main beam is in the second fixed position thereof, the first end of the elongated portion of the main beam is in the second fixed position thereof, the second end of the elongated portion of the main beam is in the second fixed portion thereof, and the at least one patient support is in the second position thereof, the positioning frame is capable of supporting the patient in the right configuration to provide greater access to a right lateral side of the patient.

In yet another aspect, the disclosure provides a method of reconfiguring a positioning frame between a left configuration and a right configuration, the positioning frame including providing a main beam of the positioning frame, the main beam having a first end, a second end, a length extending between the first and second end, a first portion at the first end, a second portion at the second end, and an elongated portion extending between the first portion and the second portion; supporting the main beam between a first vertical support portion and a second vertical support portion, the first vertical support portion being provided at a first end of the positioning frame and supporting the first end of the main beam, and the second vertical support portion being provided at a second end of the positioning frame and supporting the second end of the main beam; rotating the main beam about an axis of rotation by rotating the first portion of the main beam relative to a first portion attached to the first vertical support portion, and by rotating the second portion relative to a first portion attached to the second vertical support portion; and converting the positioning frame from the left configuration to the right configuration by rotatably adjusting the first portion of the main beam from a first fixed position to a second fixed position relative to a second portion attached to the first vertical support portion, rotatably adjusting a first end of the elongated portion of the main beam from a first fixed position to a second fixed position relative to the first portion of the main beam, rotatably adjusting a second end of the elongated portion of the main beam from a first fixed position to a second fixed position relative to the second portion of the main beam, and adjusting at least one patient support from a first location on a first side of the elongated portion of the main beam to a second location on a second side of the elongated portion of the main beam; where, when the first portion of the main beam is in the first fixed position thereof, the first end of the elongated portion of the main beam is in the first fixed position thereof, the second end of the elongated portion of the main beam is in the first fixed position thereof, and the at least one patient support is in the first location thereof, the positioning frame is capable of supporting the patient in the left configuration to provide greater access to a left lateral side of the patient, and when the first portion of the main beam is in the second fixed position thereof, the first end of the elongated portion of the main beam is in the second fixed position thereof, the second end of the elongated portion of the main beam is in the second fixed portion thereof, and the at least one patient support is in the second position thereof, the positioning frame is capable of supporting the patient in the right configuration to provide greater access to a right lateral side of the patient.

The details of one or more aspects of the disclosure as set forth in the accompanying drawings and the description below. Other features, objects, and advantages of the techniques described in this disclosure will be apparent from the description and drawings, and from the claims.

BRIEF DESCRIPTION OF DRAWINGS

FIG. 14 is a perspective view that illustrates a chest support lift mechanism of the torso-lift support of FIGS. 13A-13C with actuators thereof retracted;

DETAILED DESCRIPTION

Figure 1:
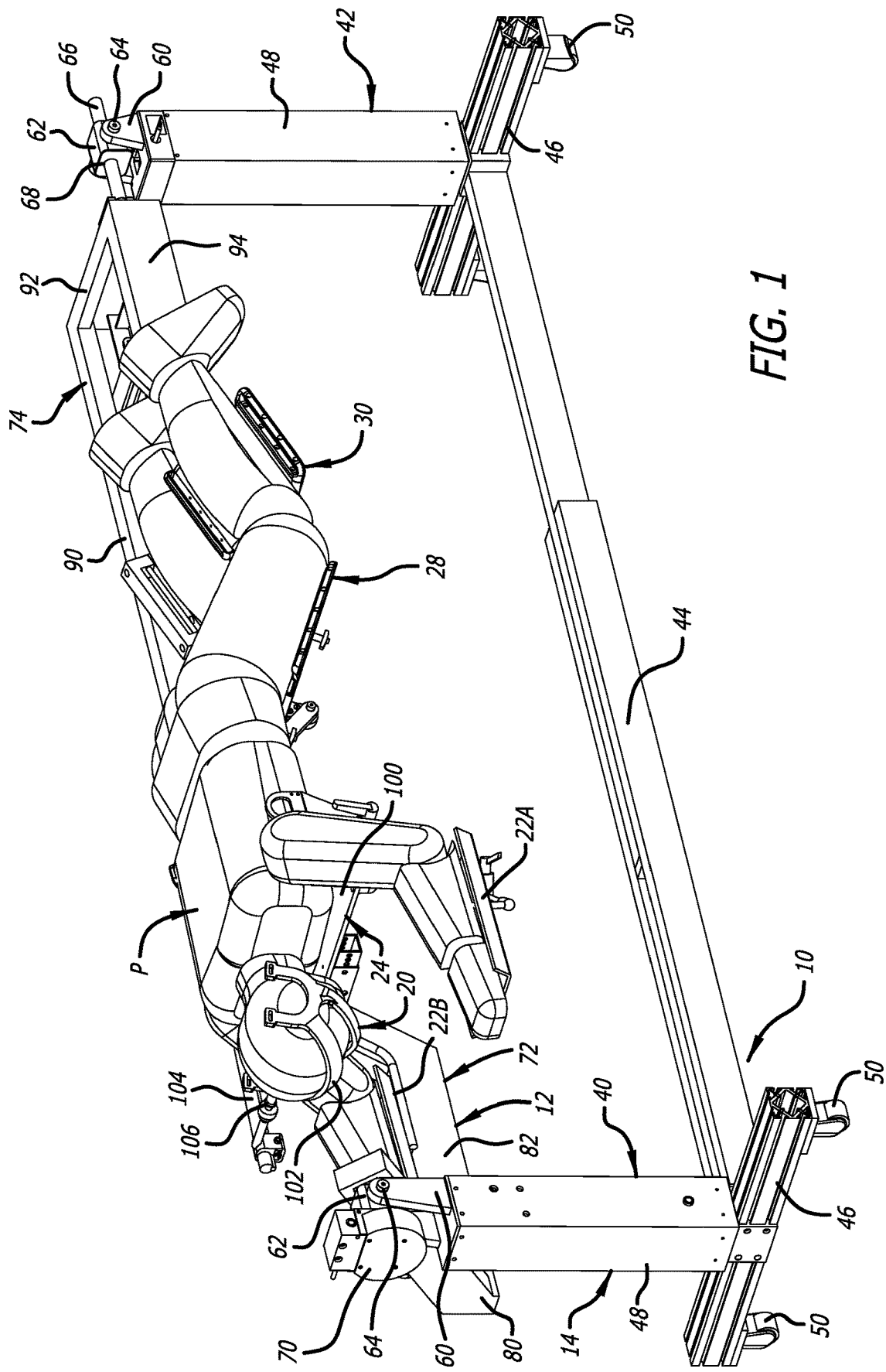
FIG. 1 is a top perspective view that illustrates a prior art surgical frame with a patient positioned thereon in a prone position.
Figure 2:
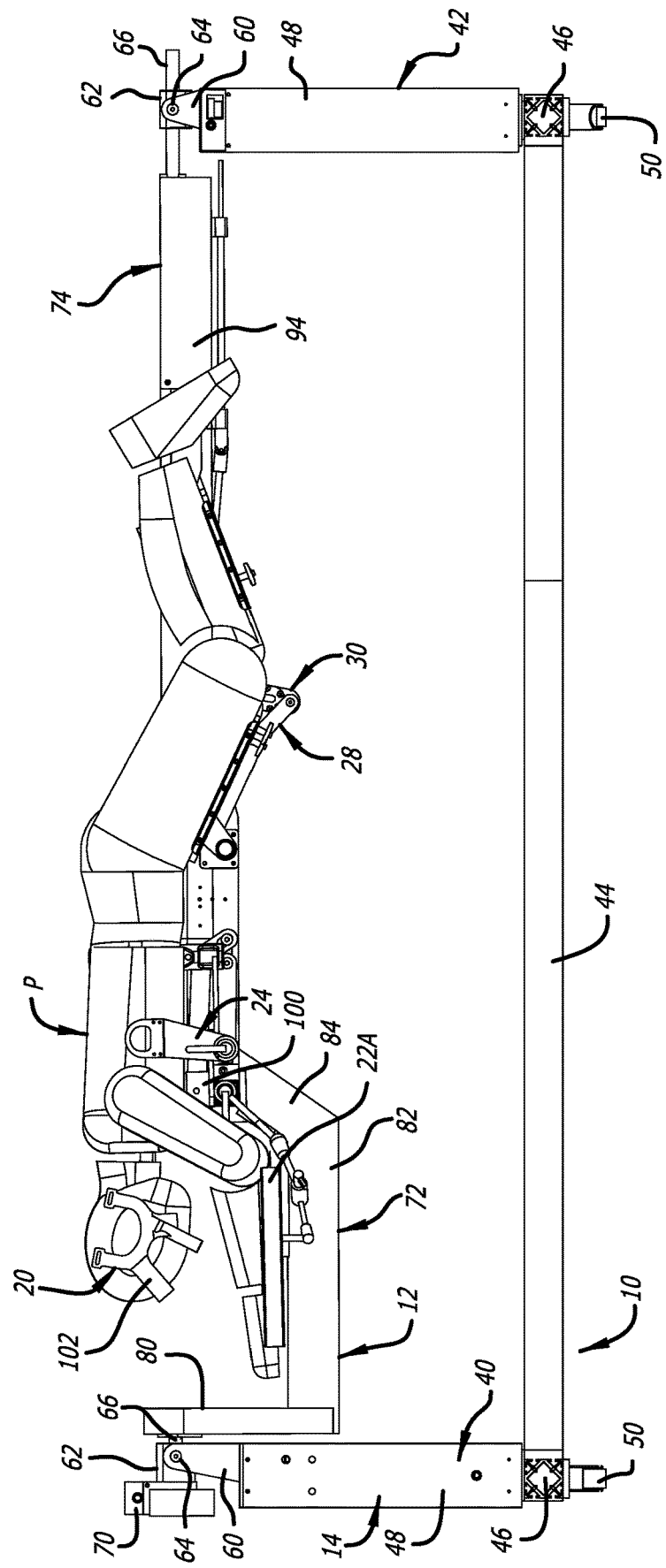
FIG. 2 is a side elevational view that illustrates the surgical frame of FIG. 1 with the patient positioned thereon in a prone position.
Figure 3:
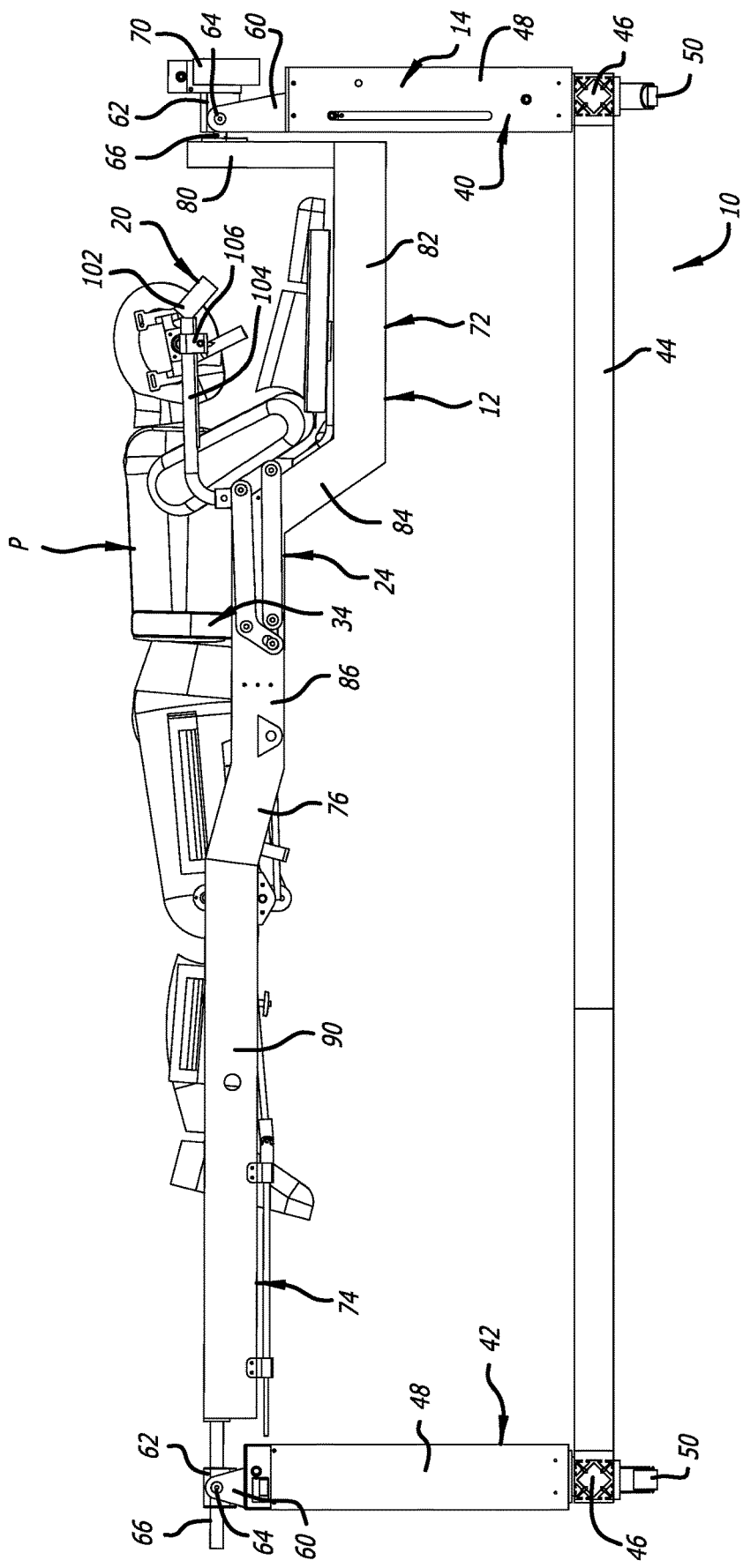
FIG. 3 is another side elevational view that illustrates the surgical frame of FIG. 1 with the patient positioned thereon in a prone position.

FIGS. 1-26 depict a prior art embodiment and components of a surgical support frame generally indicated by the numeral 10. FIGS. 1-26 were previously described in U.S. Ser. No. 15/239,256, which is hereby incorporated by reference herein in its entirety. Furthermore, FIGS. 27-30 were previously described in U.S. Ser. No. 15/639,080, which is hereby incorporated by reference herein in its entirety. U.S. Ser. No. 15/672,005 is also hereby incorporated by reference herein in its entirety.

As discussed below, the surgical frame 10 serves as an exoskeleton to support the body of the patient P as the patient's body is manipulated thereby, and, in doing so, serves to support the patient P such that the patient's spine does not experience unnecessary torsion.

The surgical frame 10 is configured to provide a relatively minimal amount of structure adjacent the patient's spine to facilitate access thereto and to improve the quality of imaging available before and during surgery. Thus, the surgeon's workspace and imaging access are thereby increased. Furthermore, radio-lucent or low magnetic susceptibility materials can be used in constructing the structural components adjacent the patient's spine in order to further enhance imaging quality.

The surgical frame 10 has a longitudinal axis and a length therealong. As depicted in FIGS. 1-5, for example, the surgical frame 10 includes an offset structural main beam 12 and a support structure 14. The offset main beam 12 is spaced from the ground by the support structure 14. As discussed below, the offset main beam 12 is used in supporting the patient P on the surgical frame 10 and various support components of the surgical frame 10 that directly contact the patient P (such as a head support 20, arm supports 22A and 22B, torso-lift supports 24 and 160, a sagittal adjustment assembly 28 including a pelvic-tilt mechanism 30 and a leg adjustment mechanism 32, and a coronal adjustment assembly 34). As discussed below, an operator such as a surgeon can control actuation of the various support components to manipulate the position of the patient's body. Soft straps (not shown) are used with these various support components to secure the patient P to the frame and to enable either manipulation or fixation of the patient P. Reusable soft pads can be used on the load-bearing areas of the various support components.

Figure 4:
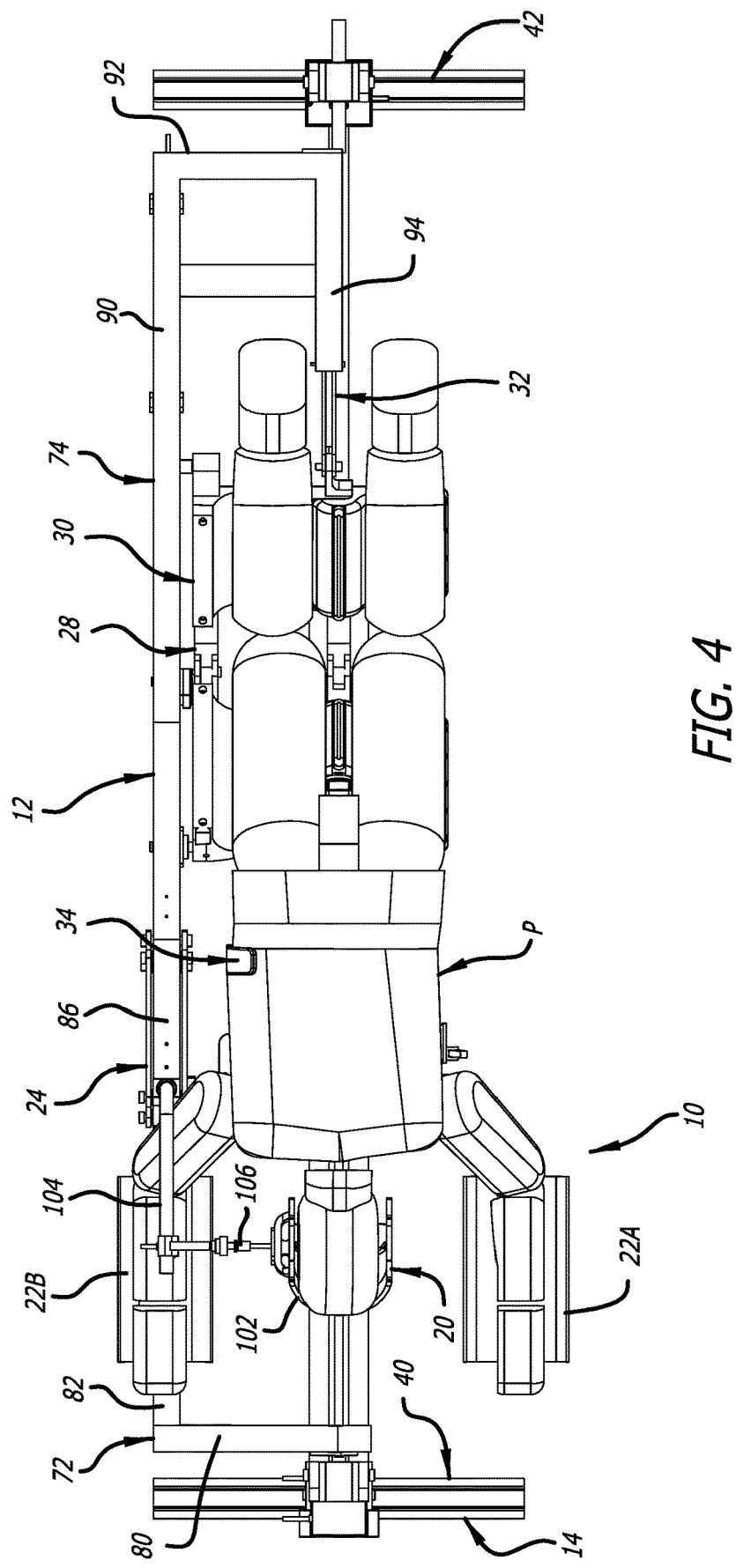
FIG. 4 is a top plan view that illustrates the surgical frame of FIG. 1 with the patient positioned thereon in a prone position.
Figure 5:
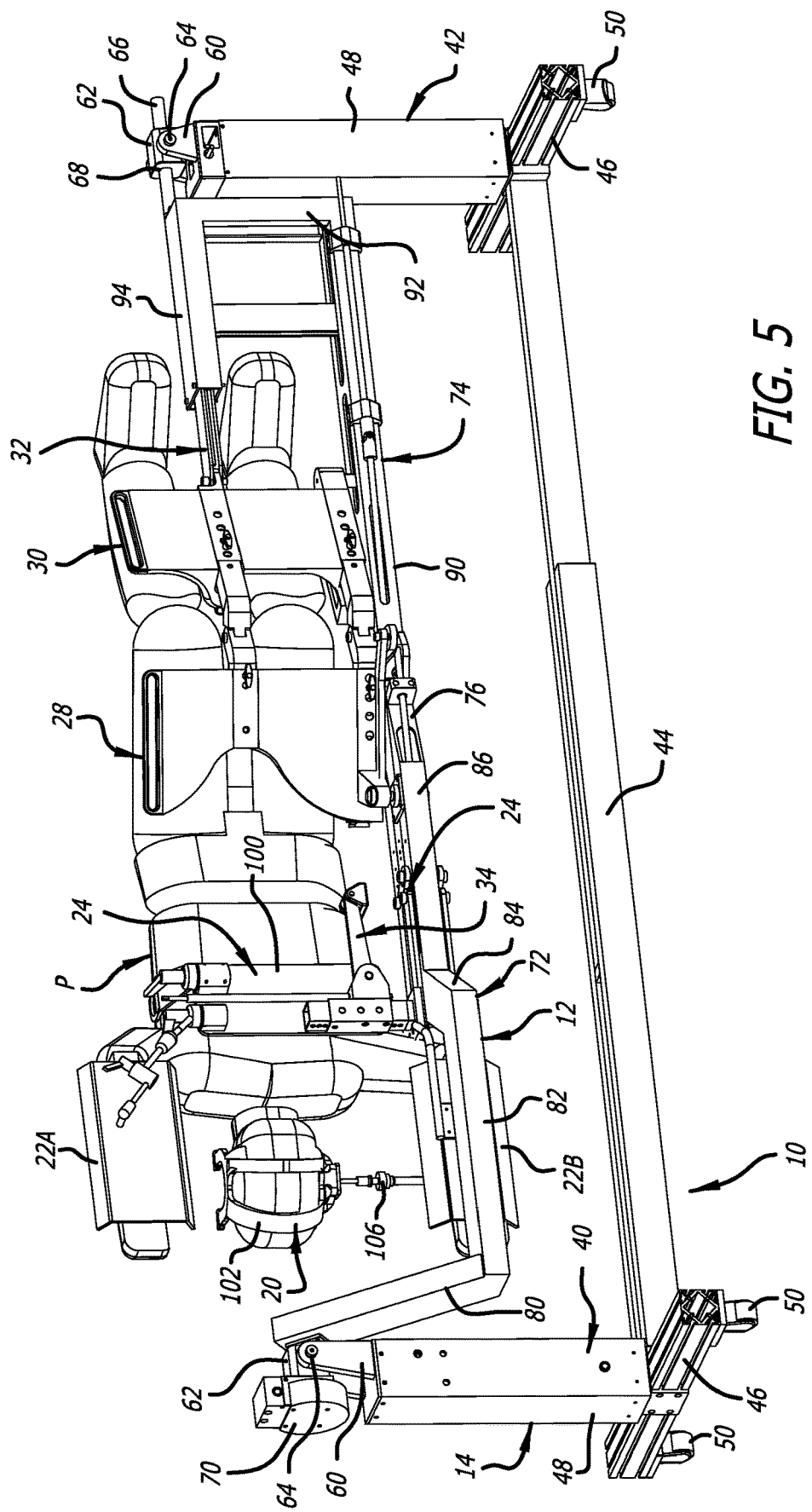
FIG. 5 is a top perspective view that illustrates the surgical frame of FIG. 1 with the patient positioned thereon in a lateral position.

The offset main beam 12 is used to facilitate rotation of the patient P. The offset main beam 12 can be rotated a full 360° before and during surgery to facilitate various positions of the patient P to afford various surgical pathways to the patient's spine depending on the surgery to be performed. For example, the offset main beam 12 can be positioned to place the patient P in a prone position (e.g., FIGS. 1-4), a lateral position (e.g., FIG. 5), and in a position 45° between the prone and lateral positions. Furthermore, the offset main beam 12 can be rotated to afford anterior, posterior, lateral, anterolateral, and posterolateral pathways to the spine. As such, the patient's body can be flipped numerous times before and during surgery without compromising sterility or safety. The various support components of the surgical frame 10 are strategically placed to further manipulate the patient's body into position before and during surgery. Such intraoperative manipulation and positioning of the patient P affords a surgeon significant access to the patient's body. To illustrate, when the offset main beam 12 is rotated to position the patient P in a lateral position, as depicted in FIG. 5, the head support 20, the arm supports 22A and 22B, the torso-lift support 24, the sagittal adjustment assembly 28, and/or the coronal adjustment assembly 34 can be articulated such that the surgical frame 10 is OLIF-capable or DLIF-capable.

As depicted in FIG. 1, for example, the support structure 14 includes a first support portion 40 and a second support portion 42 interconnected by a cross member 44. Each of the first and second support portions 40 and 42 include a horizontal portion 46 and a vertical support post 48. The horizontal portions 46 are connected to the cross member 44, and casters 50 can be attached to the horizontal portions 46 to facilitate movement of the surgical frame 10.

The vertical support posts 48 can be adjustable to facilitate expansion and contraction of the heights thereof. Expansion and contraction of the vertical support posts 48 facilitates raising and lowering, respectively, of the offset main beam 12. As such, the vertical support posts 48 can be adjusted to have equal or different heights. For example, the vertical support posts 48 can be adjusted such that the vertical support post 48 of the second support portion 42 is raised 12 inches higher than the vertical support post 48 of the first support portion 40 to place the patient P in a reverse Trendelenburg position.

Furthermore, cross member 44 can be adjustable to facilitate expansion and contraction of the length thereof. Expansion and contraction of the cross member 44 facilitates lengthening and shortening, respectively, of the distance between the first and second support portions 40 and 42.

The vertical support post 48 of the first and second support portions 40 and 42 have heights at least affording rotation of the offset main beam 12 and the patient P positioned thereon. Each of the vertical support posts 48 include a clevis 60, a support block 62 positioned in the clevis 60, and a pin 64 pinning the clevis 60 to the support block 62. The support blocks 62 are capable of pivotal movement relative to the clevises 60 to accommodate different heights of the vertical support posts 48. Furthermore, axles 66 extending outwardly from the offset main beam 12 are received in apertures 68 formed the support blocks 62. The axles 66 define an axis of rotation of the offset main beam 12, and the interaction of the axles 66 with the support blocks 62 facilitate rotation of the offset main beam 12.

Furthermore, a servomotor 70 can be interconnected with the axle 66 received in the support block 62 of the first support portion 40. The servomotor 70 can be computer controlled and/or operated by the operator of the surgical frame 10 to facilitate controlled rotation of the offset main beam 12. Thus, by controlling actuation of the servomotor 70, the offset main beam 12 and the patient P supported thereon can be rotated to afford the various surgical pathways to the patient's spine.

As depicted in FIGS. 1-5, for example, the offset main beam 12 includes a forward portion 72 and a rear portion 74. The forward portion 72 supports the head support 20, the arm supports 22A and 22B, the torso-lift support 24, and the coronal adjustment assembly 34, and the rear portion 74 supports the sagittal adjustment assembly 28. The forward and rear portions 72 and 74 are connected to one another by connection member 76 shared therebetween. The forward portion 72 includes a first portion 80, a second portion 82, a third portion 84, and a fourth portion 86. The first portion 80 extends transversely to the axis of rotation of the offset main beam 12, and the second and fourth portions 82 and 86 are aligned with the axis of rotation of the offset main beam 12. The rear portion 74 includes a first portion 90, a second portion 92, and a third portion 94. The first and third portions 90 and 94 are aligned with the axis of rotation of the offset main beam 12, and the second portion 92 extends transversely to the axis of rotation of the offset main beam 12.

The axles 66 are attached to the first portion 80 of the forward portion 72 and to the third portion 94 of the rear portion 74. The lengths of the first portion 80 of the forward portion 72 and the second portion 92 of the rear portion 74 serve in offsetting portions of the forward and rear portions 72 and 74 from the axis of rotation of the offset main beam 12. This offset affords positioning of the cranial-caudal axis of patient P approximately aligned with the axis of rotation of the offset main beam 12.

Programmable settings controlled by a computer controller (not shown) can be used to maintain an ideal patient height for a working position of the surgical frame 10 at a near-constant position through rotation cycles, for example, between the patient positions depicted in FIGS. 1 and 5. This allows for a variable axis of rotation between the first portion 40 and the second portion 42.

Figure 6:
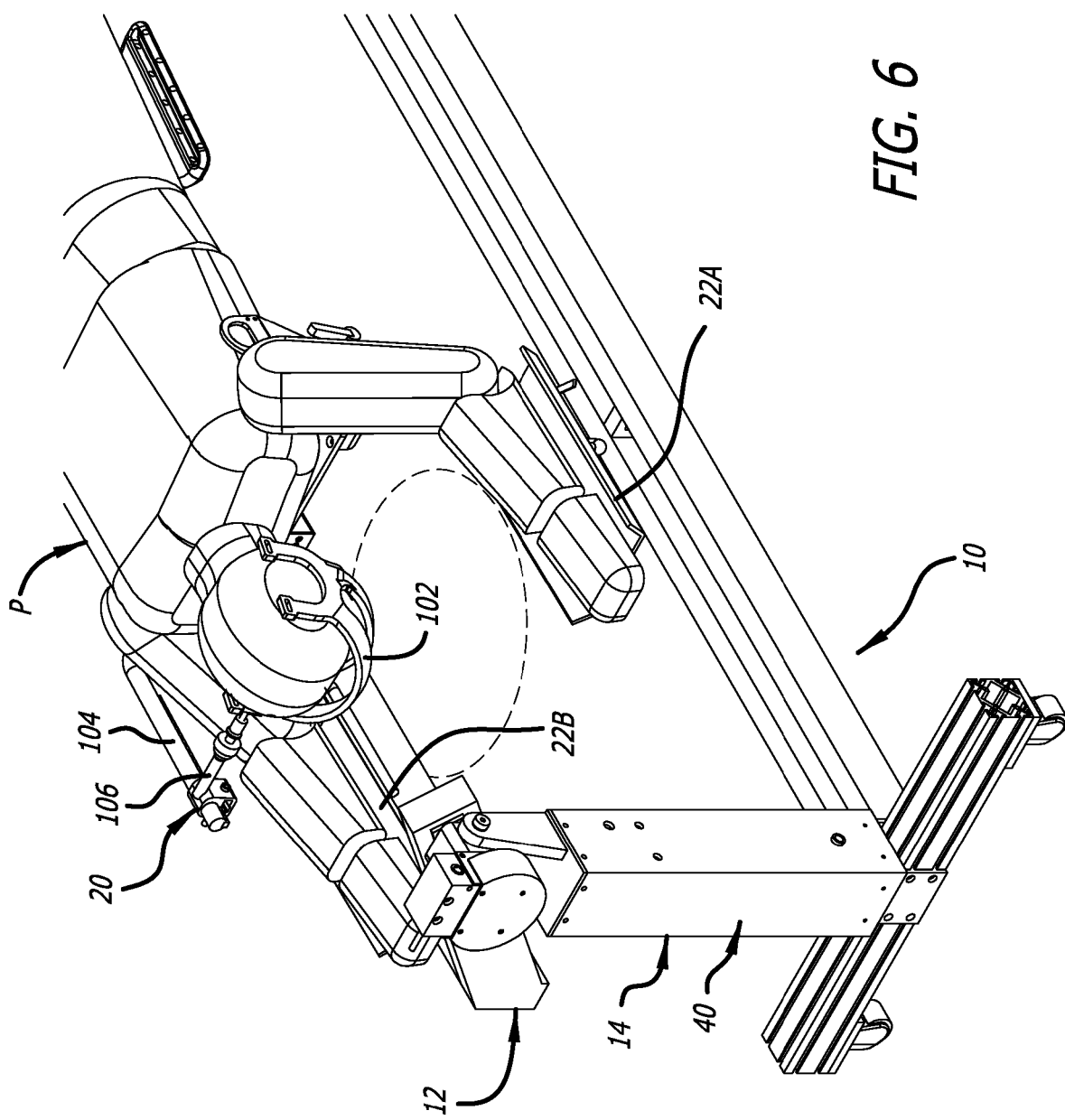
FIG. 6 is a top perspective view that illustrates portions of the surgical frame of FIG. 1 showing an area of access to the head of the patient positioned thereon in a prone position.

As depicted in FIG. 5, for example, the head support 20 is attached to a chest support plate 100 of the torso-lift support 24 to support the head of the patient P. If the torso-lift support 24 is not used, the head support 20 can be directly attached to the forward portion 72 of the offset main beam 12. As depicted in FIGS. 4 and 6, for example, the head support 20 further includes a facial support cradle 102, an axially adjustable head support beam 104, and a temple support portion 106. Soft straps (not shown) can be used to secure the patient P to the head support 20. The facial support cradle 102 includes padding across the forehead and cheeks, and provides open access to the mouth of the patient P. The head support 20 also allows for imaging access to the cervical spine. Adjustment of the head support 20 is possible via adjusting the angle and the length of the head support beam 104 and the temple support portion 106.

As depicted in FIG. 5, for example, the arm supports 22A and 22B contact the forearms and support the remainder of the arms of the patient P, with the first arm support 22A and the second arm support 22B attached to the chest support plate 100 of the torso-lift support 24. If the torso-lift support 24 is not used, the arm supports 22A and 22B can both be directly attached to the offset main beam 12. The arm supports 22A and 22B are positioned such that the arms of the patient P are spaced away from the remainder of the patient's body to provide access (FIG. 6) to at least portions of the face and neck of the patient P, thereby providing greater access to the patient.

Figure 7:
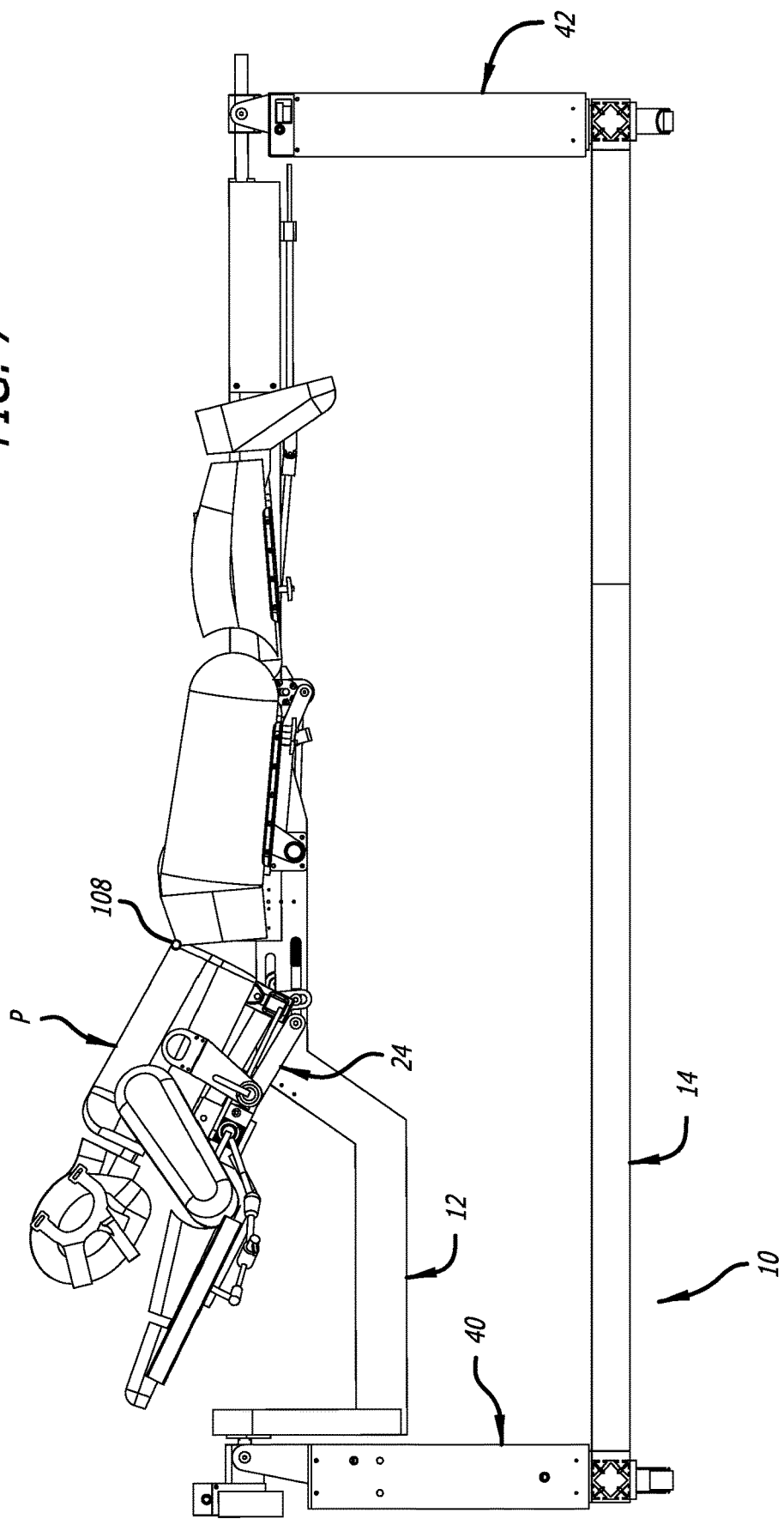
FIG. 7 is a side elevational view that illustrates the surgical frame of FIG. 1 showing a torso-lift support supporting the patient in a lifted position.
Figure 8:
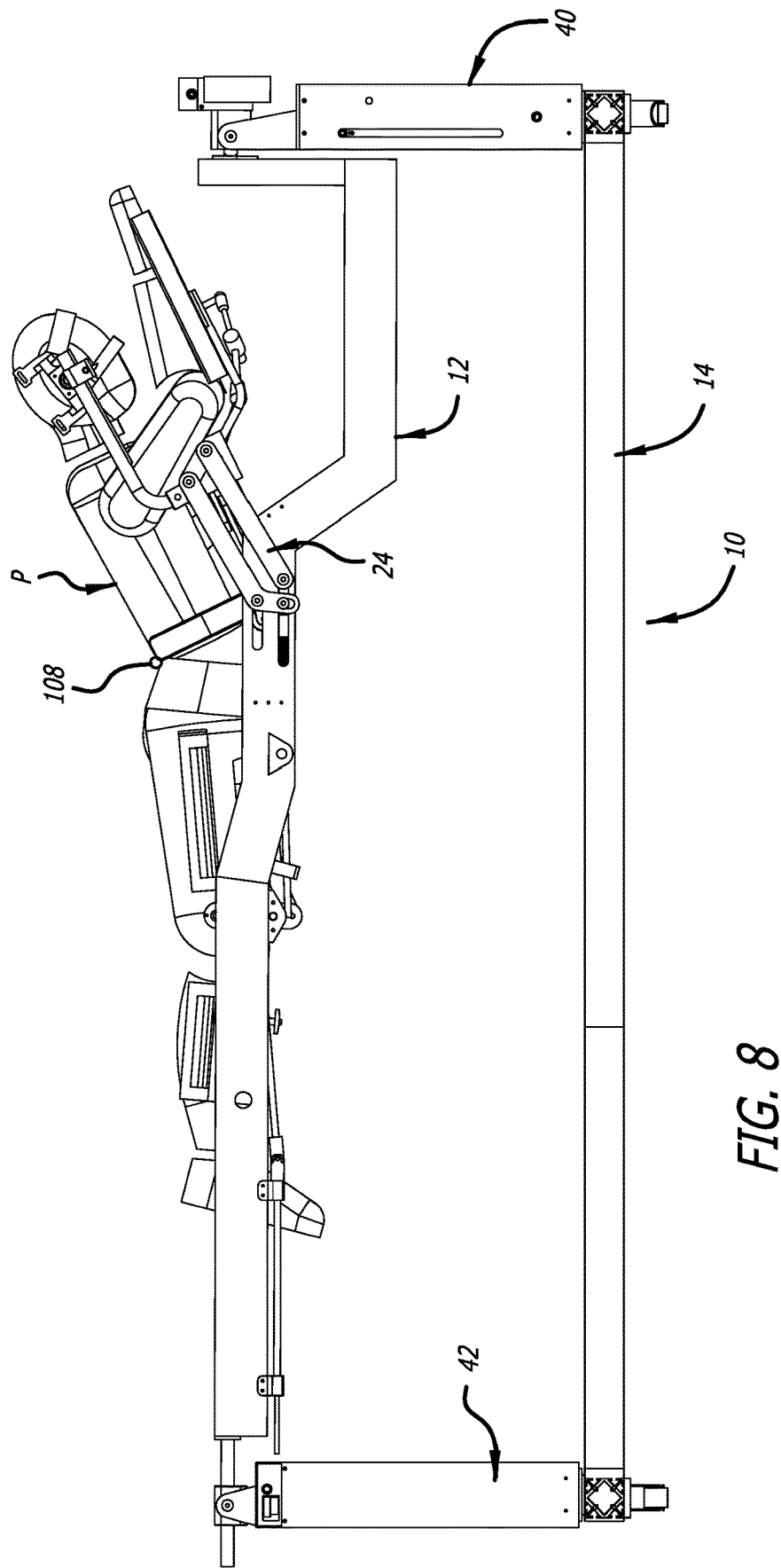
FIG. 8 is another side elevational view that illustrates the surgical frame of FIG. 1 showing the torso-lift support supporting the patient in the lifted position.
Figure 9:
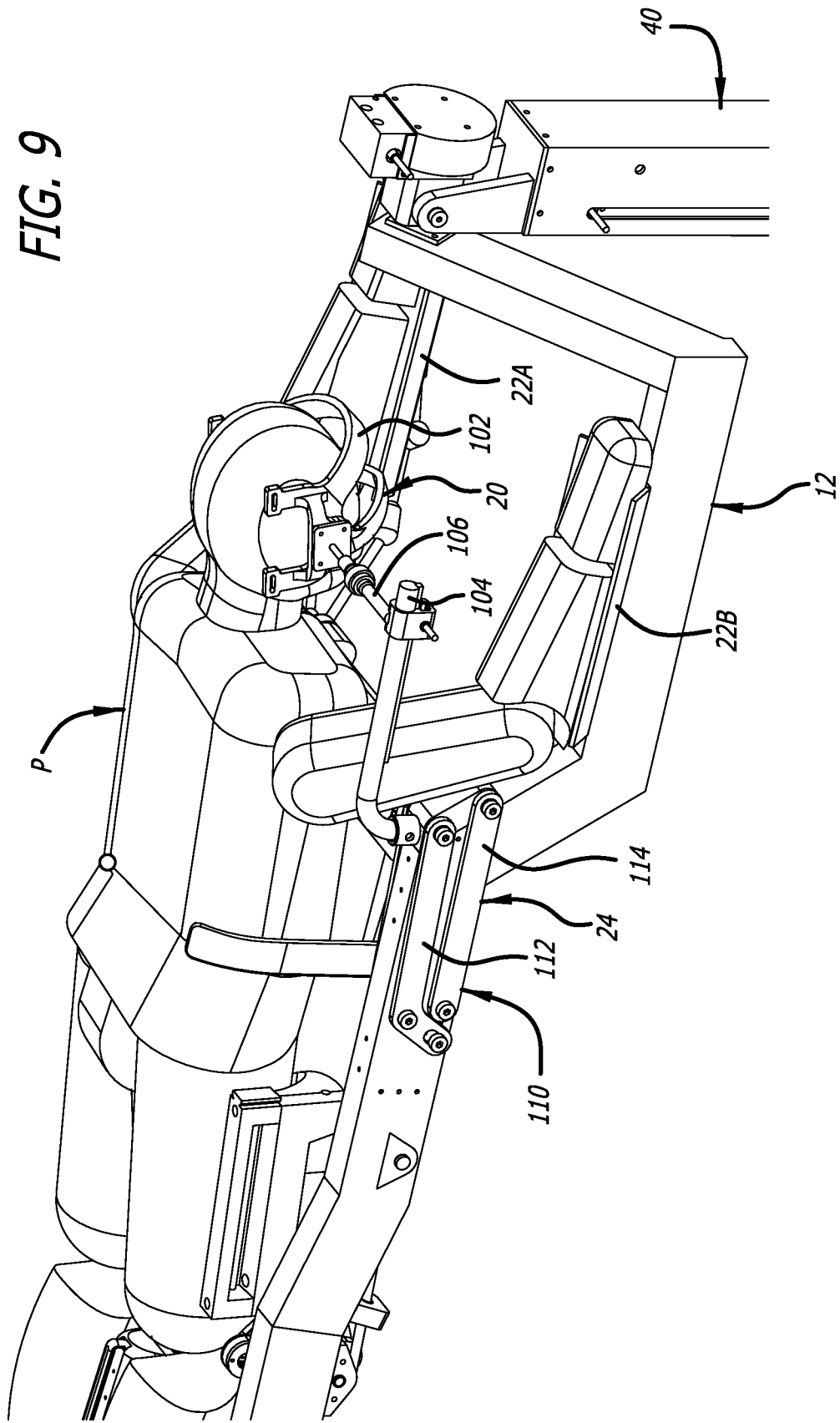
FIG. 9 is an enlarged top perspective view that illustrates portions of the surgical frame of FIG. 1 showing the torso-lift support supporting the patient in an unlifted position.

As depicted in FIGS. 7-12, for example, the surgical frame 10 includes a torso-lift capability for lifting and lowering the torso of the patient P between an uplifted position and a lifted position, which is described in detail below with respect to the torso-lift support 24. As depicted in FIGS. 7 and 8, for example, the torso-lift capability has an approximate center of rotation ("COR") 108 that is located at a position anterior to the patient's spine about the L2 of the lumbar spine, and is capable of elevating the upper body of the patient at least an additional six inches when measured at the chest support plate 100.

As depicted in FIGS. 9-12, for example, the torso-lift support 24 includes a "crawling" four-bar mechanism 110 attached to the chest support plate 100. Soft straps (not shown) can be used to secure the patient P to the chest support plate 100. The head support 20 and the arm supports 22A and 22B are attached to the chest support plate 100, thereby moving with the chest support plate 100 as the chest support plate 100 is articulated using the torso-lift support 24. The fixed COR 108 is defined at the position depicted in FIGS. 7 and 8. Appropriate placement of the COR 108 is important so that spinal cord integrity is not compromised (i.e., overly compressed or stretched) during the lift maneuver performed by the torso-lift support 24.

Figure 10:
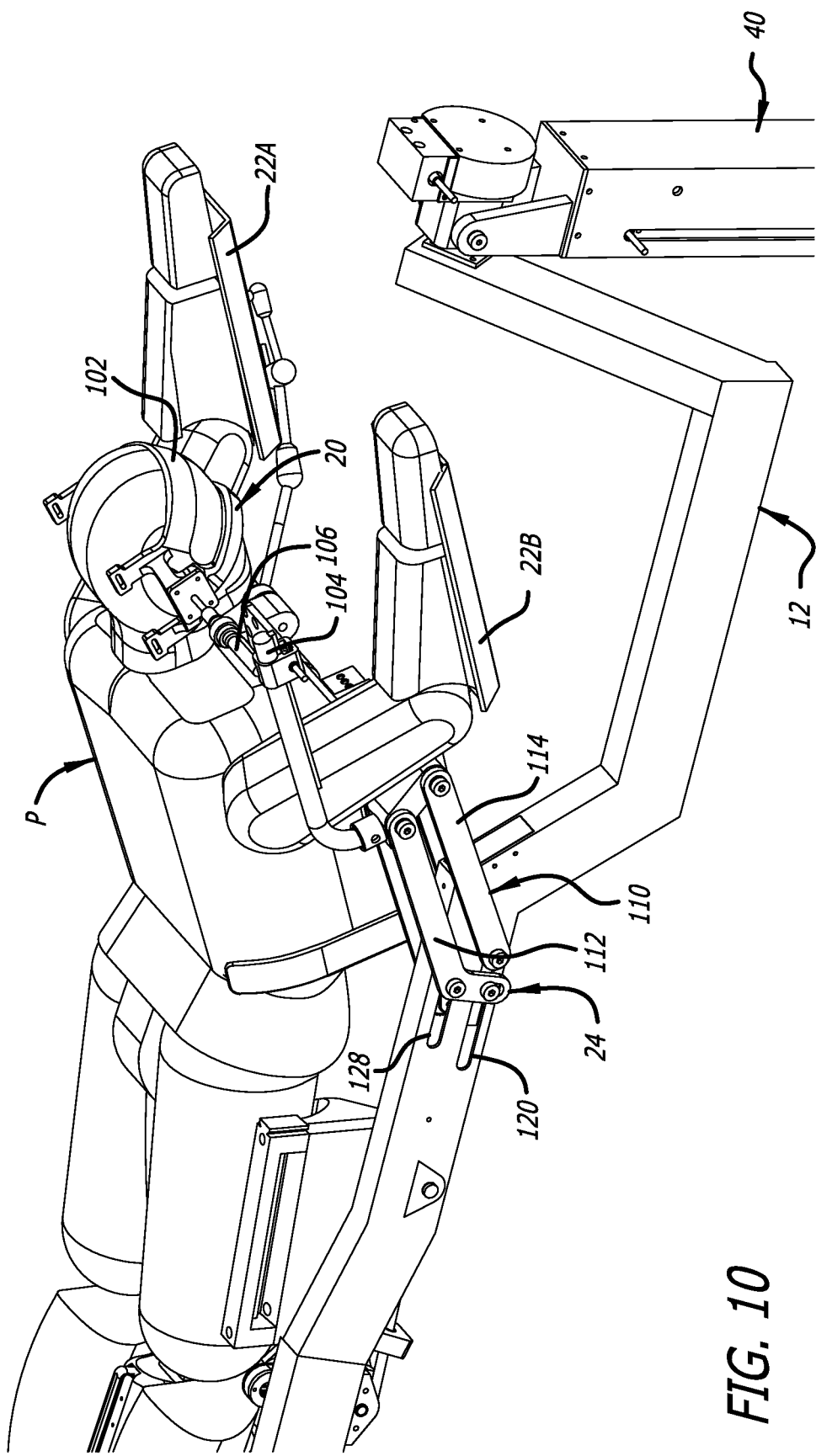
FIG. 10 is an enlarged top perspective view that illustrates portions of the surgical frame of FIG. 1 showing the torso-lift support supporting the patient in the lifted position.
Figure 11:
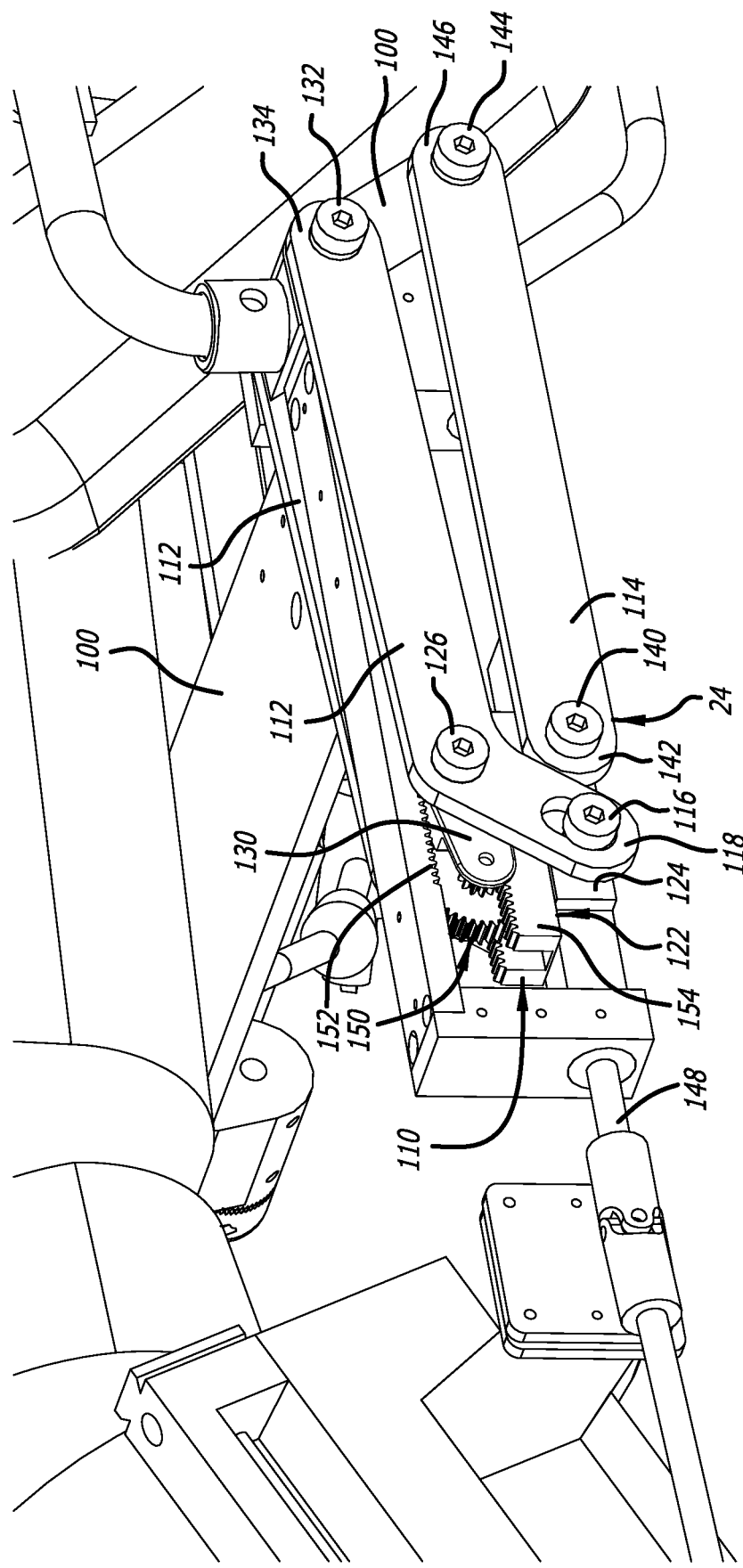
FIG. 11 is an enlarged top perspective view that illustrates componentry of the torso-lift support in the unlifted position.
Figure 12:
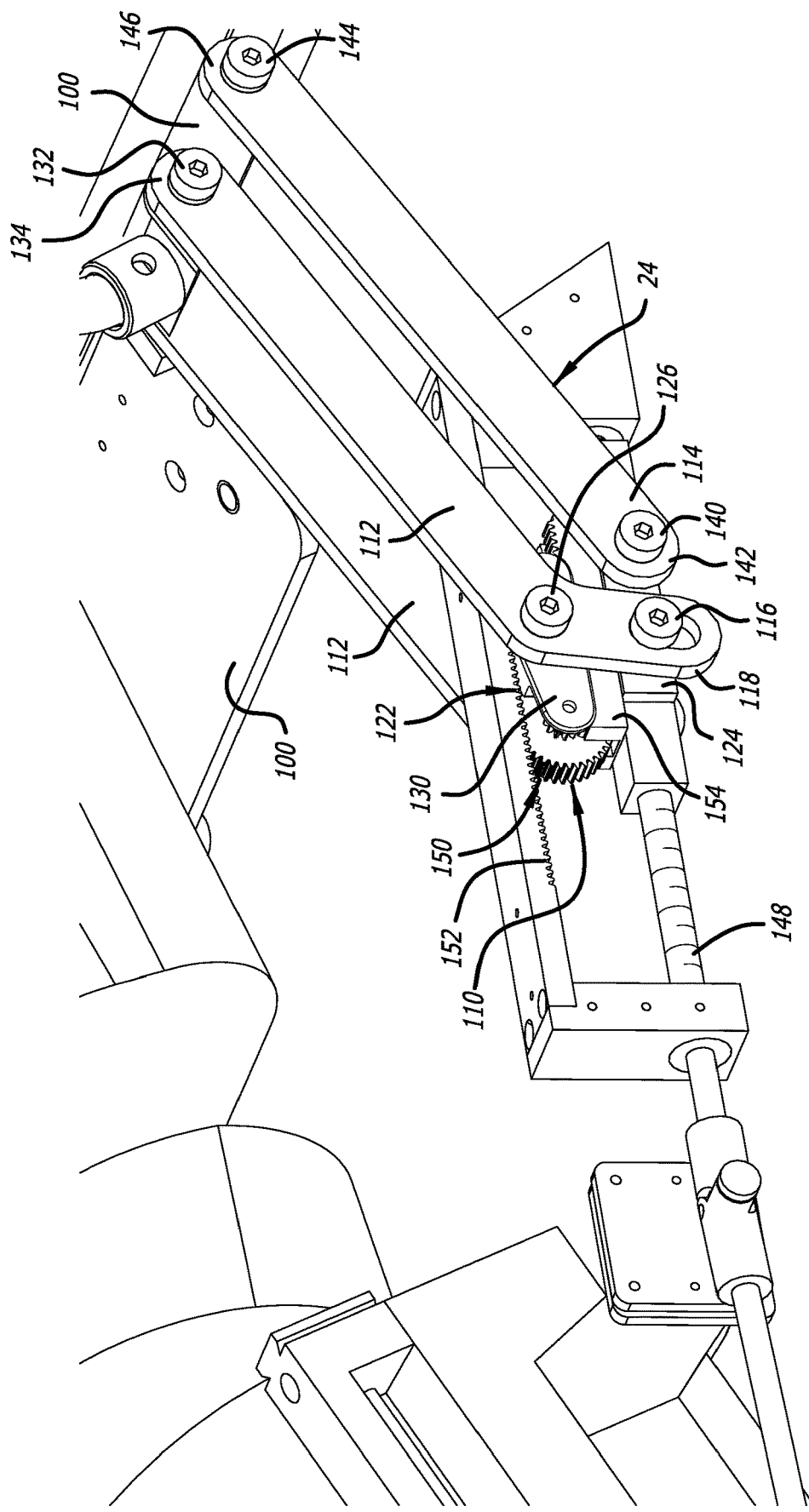
FIG. 12 is an enlarged top perspective view that illustrates the componentry of the torso-lift support in the lifted position.

As depicted in FIGS. 10-12, for example, the four-bar mechanism 110 includes first links 112 pivotally connected between offset main beam 12 and the chest support plate 100, and second links 114 pivotally connected between the offset main beam 12 and the chest support plate 100. As depicted in FIGS. 11 and 12, for example, in order to maintain the COR 108 at the desired fixed position, the first and second links 112 and 114 of the four-bar mechanism 110 crawl toward the first support portion 40 of the support structure 14, when the patient's upper body is being lifted. The first and second links 112 and 114 are arranged such that neither the surgeon's workspace nor imaging access are compromised while the patient's torso is being lifted.

As depicted in FIGS. 11 and 12, for example, each of the first links 112 define an L-shape, and includes a first pin 116 at a first end 118 thereof. The first pin 116 extends through first elongated slots 120 defined in the offset main beam 12, and the first pin 116 connects the first links 112 to a dual rack and pinion mechanism 122 via a drive nut 124 provided within the offset main beam 12, thus defining a lower pivot point thereof. Each of the first links 112 also includes a second pin 126 positioned proximate the corner of the L-shape. The second pin 126 extends through second elongated slots 128 defined in the offset main beam 12, and is linked to a carriage 130 of rack and pinion mechanism 122. Each of the first links 112 also includes a third pin 132 at a second end 134 that is pivotally attached to chest support plate 100, thus defining an upper pivot point thereof.

As depicted in FIGS. 11 and 12, for example, each of the second links 114 includes a first pin 140 at a first end 142 thereof. The first pin 140 extends through the first elongated slot 120 defined in the offset main beam 12, and the first pin 140 connects the second links 114 to the drive nut 124 of the rack and pinion mechanism 122, thus defining a lower pivot point thereof. Each of the second links 114 also includes a second pin 144 at a second end 146 that is pivotally connected to the chest support plate 100, thus defining an upper pivot point thereof.

As depicted in FIGS. 11 and 12, the rack and pinion mechanism 122 includes a drive screw 148 engaging the drive nut 124. Coupled gears 150 are attached to the carriage 130. The larger of the gears 150 engage an upper rack 152 (fixed within the offset main beam 12), and the smaller of the gears 150 engage a lower rack 154. The carriage 130 is defined as a gear assembly that floats between the two racks 152 and 154.

As depicted in FIGS. 11 and 12, the rack and pinion mechanism 122 converts rotation of the drive screw 148 into linear translation of the first and second links 112 and 114 in the first and second elongated slots 120 and 128 toward the first portion 40 of the support structure 14. As the drive nut 124 translates along drive screw 148 (via rotation of the drive screw 148), the carriage 130 translates towards the first portion 40 with less travel due to the different gear sizes of the coupled gears 150. The difference in travel, influenced by different gear ratios, causes the first links 112 pivotally attached thereto to lift the chest support plate 100. Lowering of the chest support plate 100 is accomplished by performing this operation in reverse. The second links 114 are "idler" links (attached to the drive nut 124 and the chest support plate 100) that controls the tilt of the chest support plate 100 as it is being lifted and lowered. All components associated with lifting while tilting the chest plate predetermine where COR 108 resides. Furthermore, a servomotor (not shown) interconnected with the drive screw 148 can be computer controlled and/or operated by the operator of the surgical frame 10 to facilitate controlled lifting and lowering of the chest support plate 100. A safety feature can be provided, enabling the operator to read and limit a lifting and lowering force applied by the torso-lift support 24 in order to prevent injury to the patient P. Moreover, the torso-lift support 24 can also include safety stops (not shown) to prevent over-extension or compression of the patient P, and sensors (not shown) programmed to send patient position feedback to the safety stops.

Figure 13A:
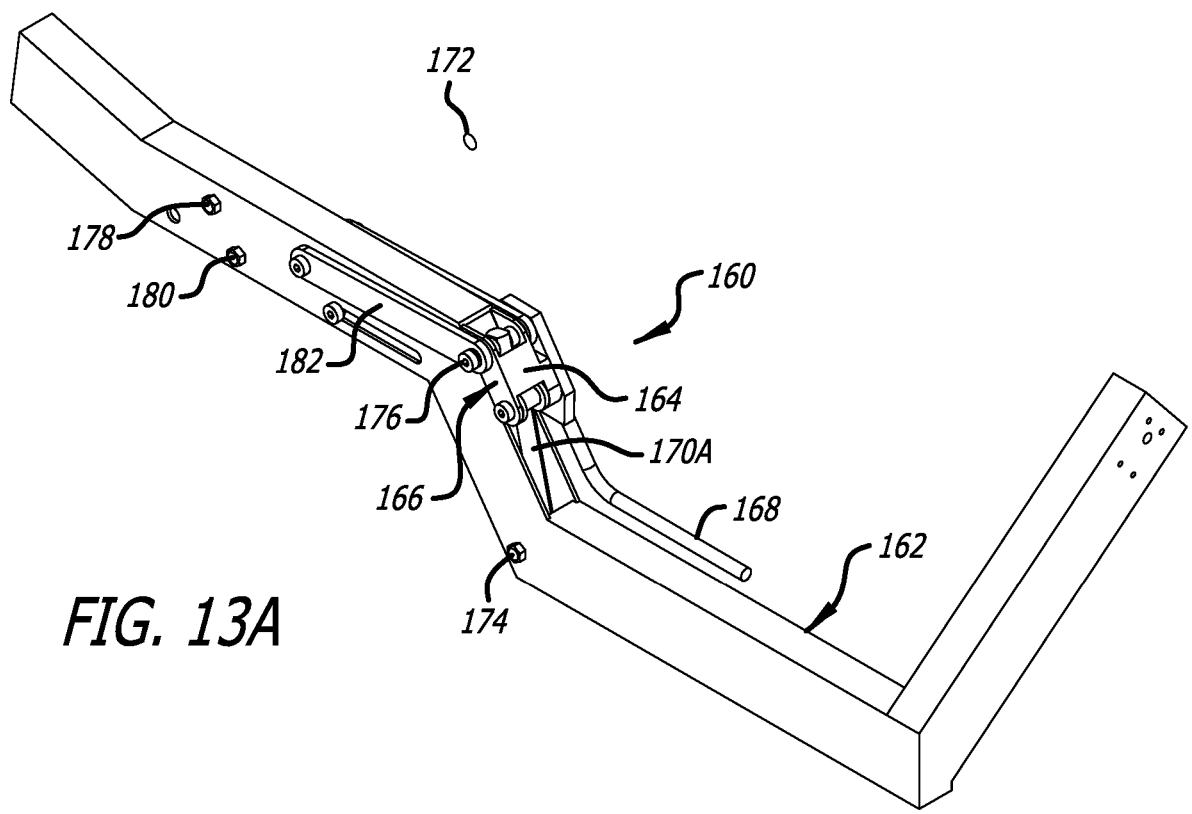
FIG. 13A is a perspective view that illustrates an embodiment of a structural offset main beam for use with another embodiment of a torso-lift support showing the torso-lift support in a retracted position.

An alternative preferred embodiment of a torso-lift support is generally indicated by the numeral 160 in FIGS. 13A-15. As depicted in FIGS. 13A-13C, an alternate offset main beam 162 is utilized with the torso-lift support 160. Furthermore, the torso-lift support 160 has a support plate 164 pivotally linked to the offset main beam 162 by a chest support lift mechanism 166. An arm support rod/plate 168 is connected to the support plate 164, and the second arm support 22B. The support plate 164 is attached to the chest support plate 100, and the chest support lift mechanism 166 includes various actuators 170A, 170B, and 170C used to facilitate positioning and repositioning of the support plate 164 (and hence, the chest support plate 100).

Figure 13B:
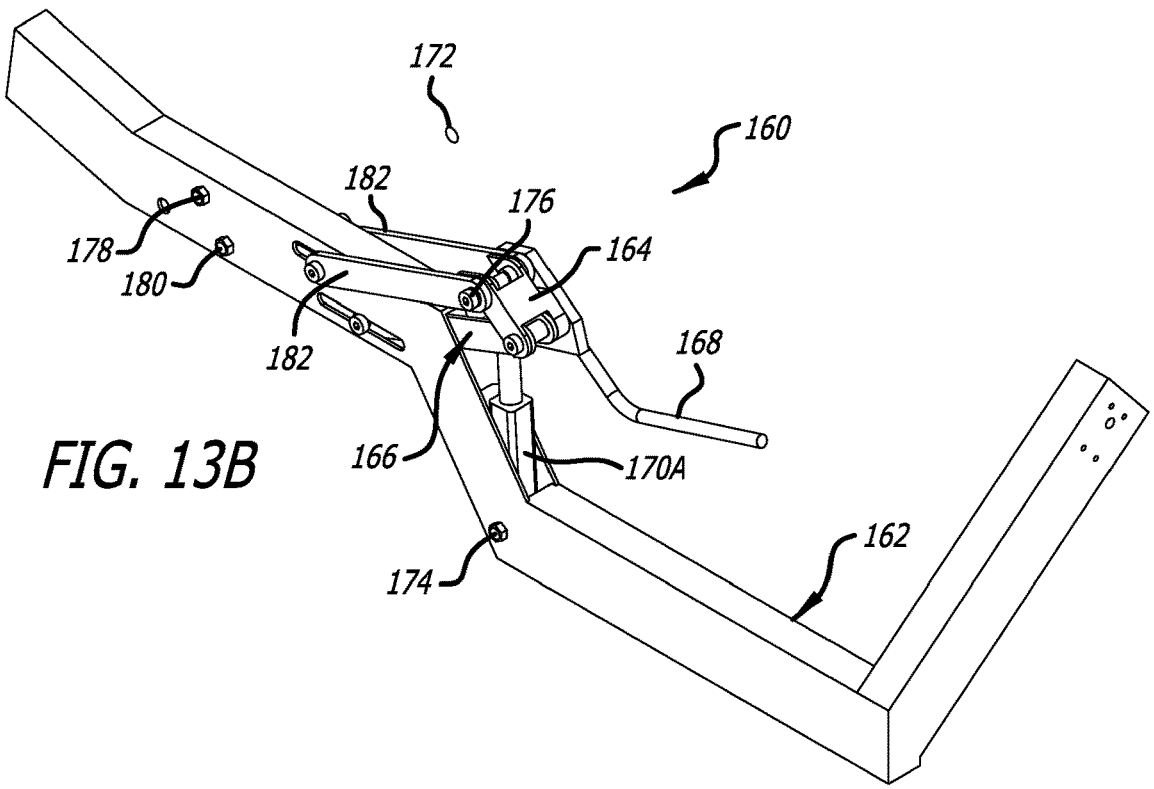
FIG. 13B is a perspective view similar to FIG. 13A that illustrates the torso-lift support at half travel.
Figure 13C:
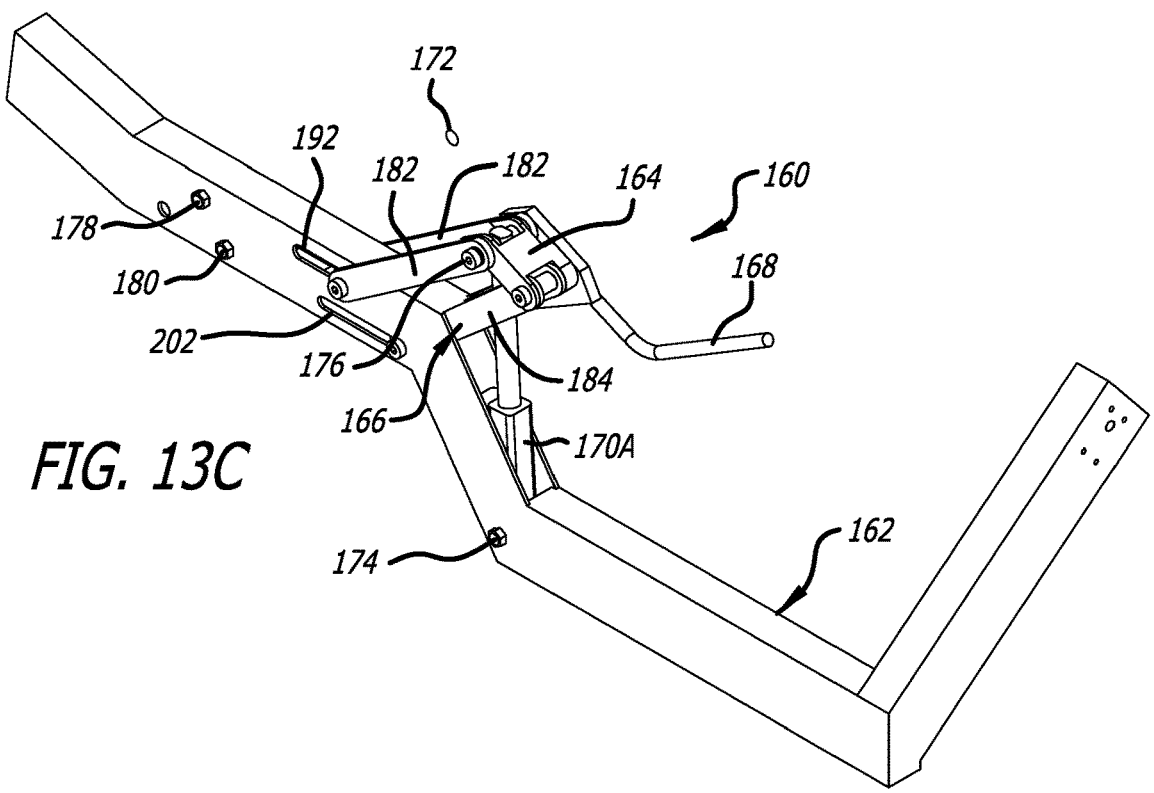
FIG. 13C is a perspective view similar to FIGS. 13A and 13B that illustrates the torso-lift support at full travel.

As discussed below, the torso-lift support 160 depicted in FIGS. 13A-15 enables a COR 172 thereof to be programmably altered such that the COR 172 can be a fixed COR or a variable COR. As their names suggest, the fixed COR stays in the same position as the torso-lift support 160 is actuated, and the variable COR moves between a first position and a second position as the torso-lift support 160 is actuated between its initial position and final position at full travel thereof. Appropriate placement of the COR 172 is important so that spinal cord integrity is not compromised (i.e., overly compressed or stretched). Thus, the support plate 164 (and hence, the chest support plate 100) follows a path coinciding with a predetermined COR 172 (either fixed or variable). FIG. 13A depicts the torso-lift support 160 retracted, FIG. 13B depicts the torso-lift support 160 at half travel, and FIG. 13C depicts the torso-lift support 160 at full travel.

Figure 15:
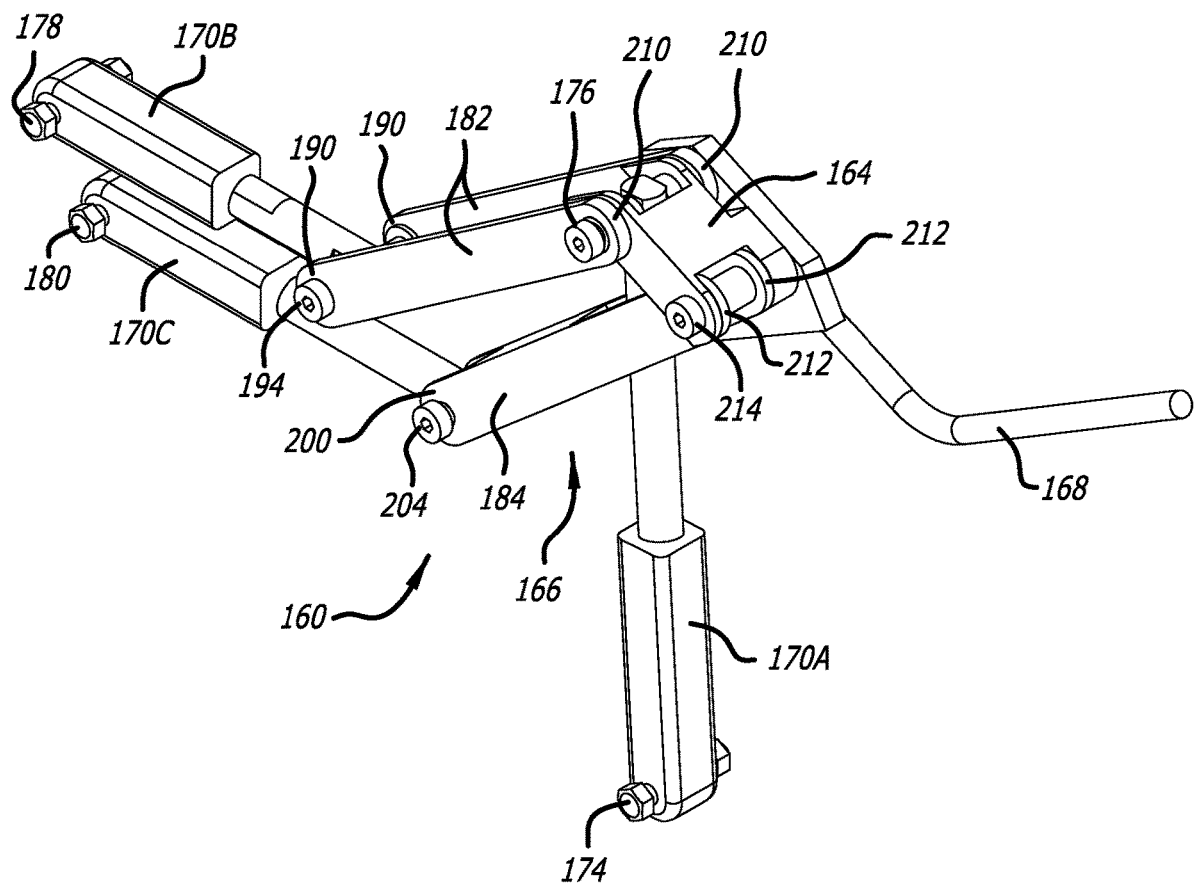
FIG. 15 is another perspective view that illustrates a chest support lift mechanism of the torso-lift support of FIGS. 13A-13C with the actuators thereof extended.

As discussed above, the chest support lift mechanism 166 includes the actuators 170A, 170B, and 170C to position and reposition the support plate 164 (and hence, the chest support plate 100). As depicted in FIGS. 14 and 15, for example, the first actuator 170A, the second actuator 1706, and the third actuator 170C are provided. Each of the actuators 170A, 170B, and 170C are interconnected with the offset main beam 12 and the support plate 164, and each of the actuators 170A, 170B, and 170C are moveable between a retracted and extended position. As depicted in FIGS. 13A-13C, the first actuator 170A is pinned to the offset main beam 162 using a pin 174 and pinned to the support plate 164 using a pin 176. Furthermore, the second and third actuators 170B and 170C are received within the offset main beam 162. The second actuator 170B is interconnected with the offset main beam 162 using a pin 178, and the third actuator 170C is interconnected with the offset main beam 162 using a pin 180.

The second actuator 170B is interconnected with the support plate 164 via first links 182, and the third actuator 170C is interconnected with the support plate 164 via second links 184. First ends 190 of the first links 182 are pinned to the second actuator 170B and elongated slots 192 formed in the offset main beam 162 using a pin 194, and first ends 200 of the second links 184 are pinned to the third actuator 170C and elongated slots 202 formed in the offset main beam 162 using a pin 204. The pins 194 and 204 are moveable within the elongated slots 192 and 202. Furthermore, second ends 210 of the first links 182 are pinned to the support plate 164 using the pin 176, and second ends 212 of the second links 184 are pinned to the support plate 164 using a pin 214. To limit interference therebetween, as depicted in FIGS. 13A-13C, the first links 182 are provided on the exterior of the offset main beam 162, and, depending on the position thereof, the second links 184 are positioned on the interior of the offset main beam 162.

Actuation of the actuators 170A, 170B, and 170C facilitates movement of the support plate 164. Furthermore, the amount of actuation of the actuators 170A, 170B, and 170C can be varied to affect different positions of the support plate 164. As such, by varying the amount of actuation of the actuators 170A, 170B, and 170C, the COR 172 thereof can be controlled. As discussed above, the COR 172 can be predetermined, and can be either fixed or varied. Furthermore, the actuation of the actuators 170A, 170B, and 170C can be computer controlled and/or operated by the operator of the surgical frame 10, such that the COR 172 can be programmed by the operator. As such, an algorithm can be used to determine the rates of extension of the actuators 170A, 170B, and 170C to control the COR 172, and the computer controls can handle implementation of the algorithm to provide the predetermined COR. A safety feature can be provided, enabling the operator to read and limit a lifting force applied by the actuators 170A, 170B, and 170C in order to prevent injury to the patient P. Moreover, the torso-lift support 160 can also include safety stops (not shown) to prevent over-extension or compression of the patient P, and sensors (not shown) programmed to send patient position feedback to the safety stops.

FIGS. 16-23 depict portions of the sagittal adjustment assembly 28. The sagittal adjustment assembly 28 can be used to distract or compress the patient's lumbar spine during or after lifting or lowering of the patient's torso by the torso-lift supports. The sagittal adjustment assembly 28 supports and manipulates the lower portion of the patient's body. In doing so, the sagittal adjustment assembly 28 is configured to make adjustments in the sagittal plane of the patient's body, including tilting the pelvis, controlling the position of the upper and lower legs, and lordosing the lumbar spine.

Figure 16:
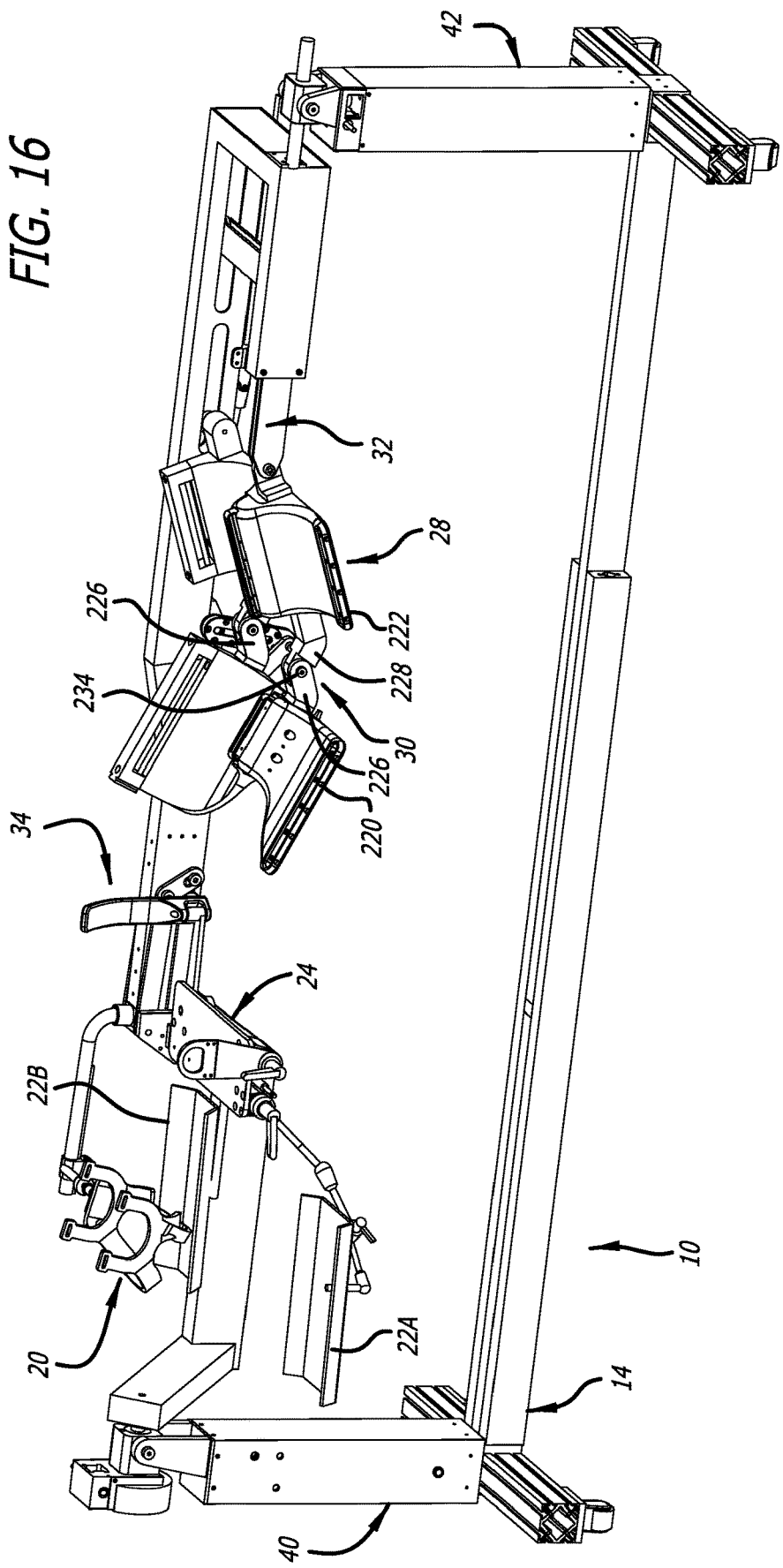
FIG. 16 is a top perspective view that illustrates the surgical frame of FIG. 5.
Figure 17:
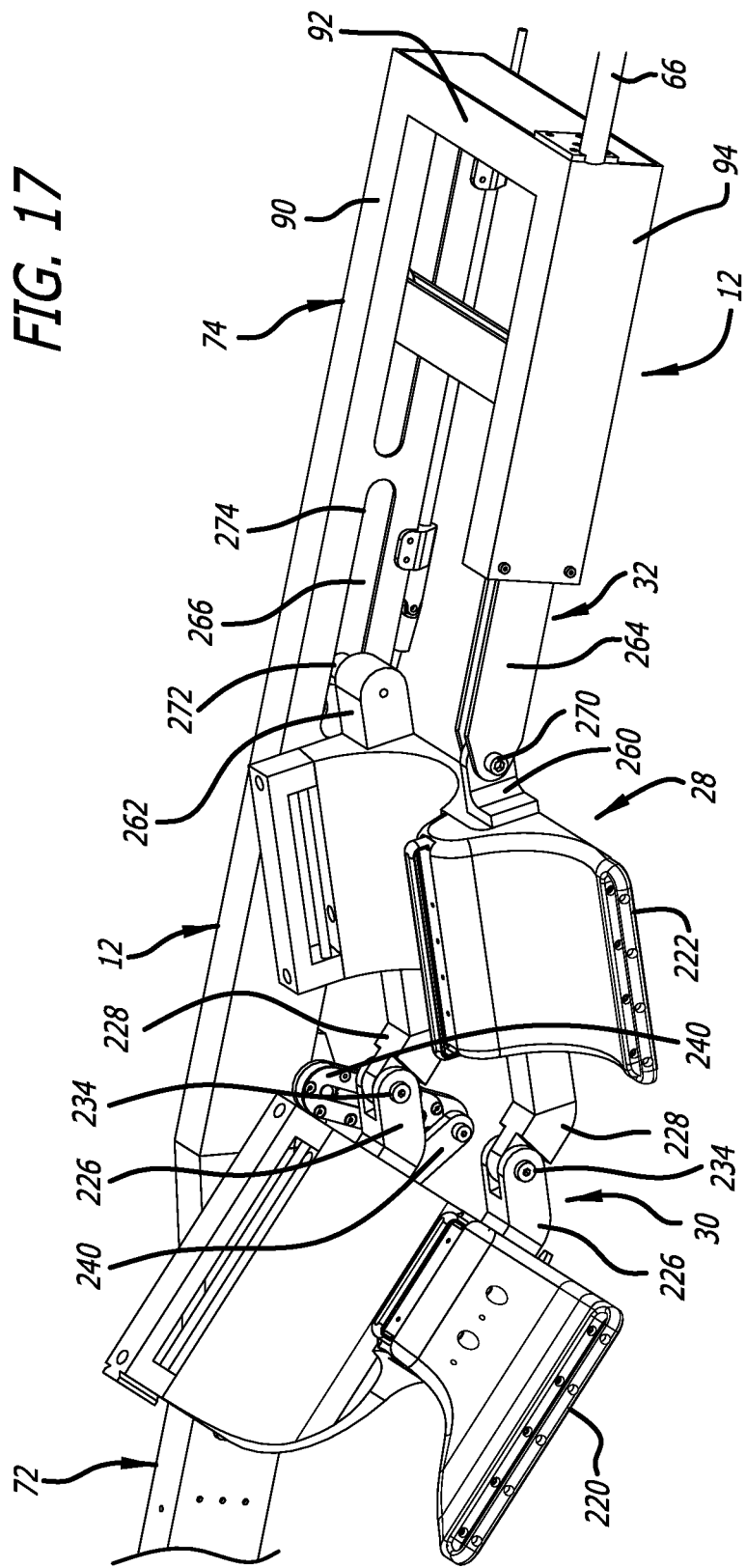
FIG. 17 is an enlarged top perspective view that illustrates portions of the surgical frame of FIG. 1 showing a sagittal adjustment assembly including a pelvic-tilt mechanism and leg adjustment mechanism.

As depicted in FIGS. 16 and 17, for example, the sagittal adjustment assembly 28 includes the pelvic-tilt mechanism 30 for supporting the thighs and lower legs of the patient P.

The pelvic-tilt mechanism 30 includes a thigh cradle 220 configured to support the patient's thighs, and a lower leg cradle 222 configured to support the patient's shins. Different sizes of thigh and lower leg cradles can be used to accommodate different sizes of patients, i.e., smaller thigh and lower leg cradles can be used with smaller patients, and larger thigh and lower leg cradles can be used with larger patients. Soft straps (not shown) can be used to secure the patient P to the thigh cradle 220 and the lower leg cradle 222. The thigh cradle 220 and the lower leg cradle 222 are moveable and pivotal with respect to one another and to the offset main beam 12. To facilitate rotation of the patient's hips, the thigh cradle 220 and the lower leg cradle 222 can be positioned anterior and inferior to the patient's hips.

Figure 18:
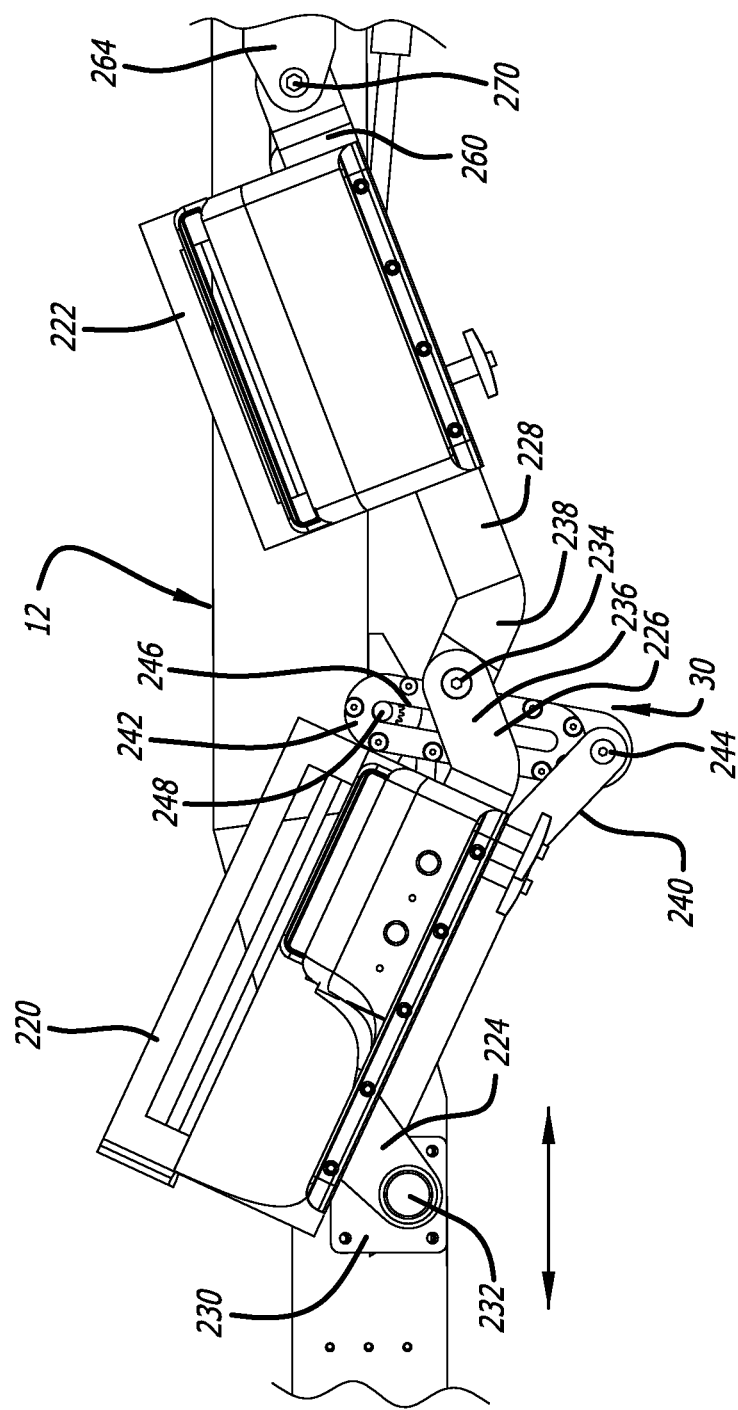
FIG. 18 is an enlarged side elevational view that illustrates portions of the surgical frame of FIG. 1 showing the pelvic-tilt mechanism.
Figure 25:
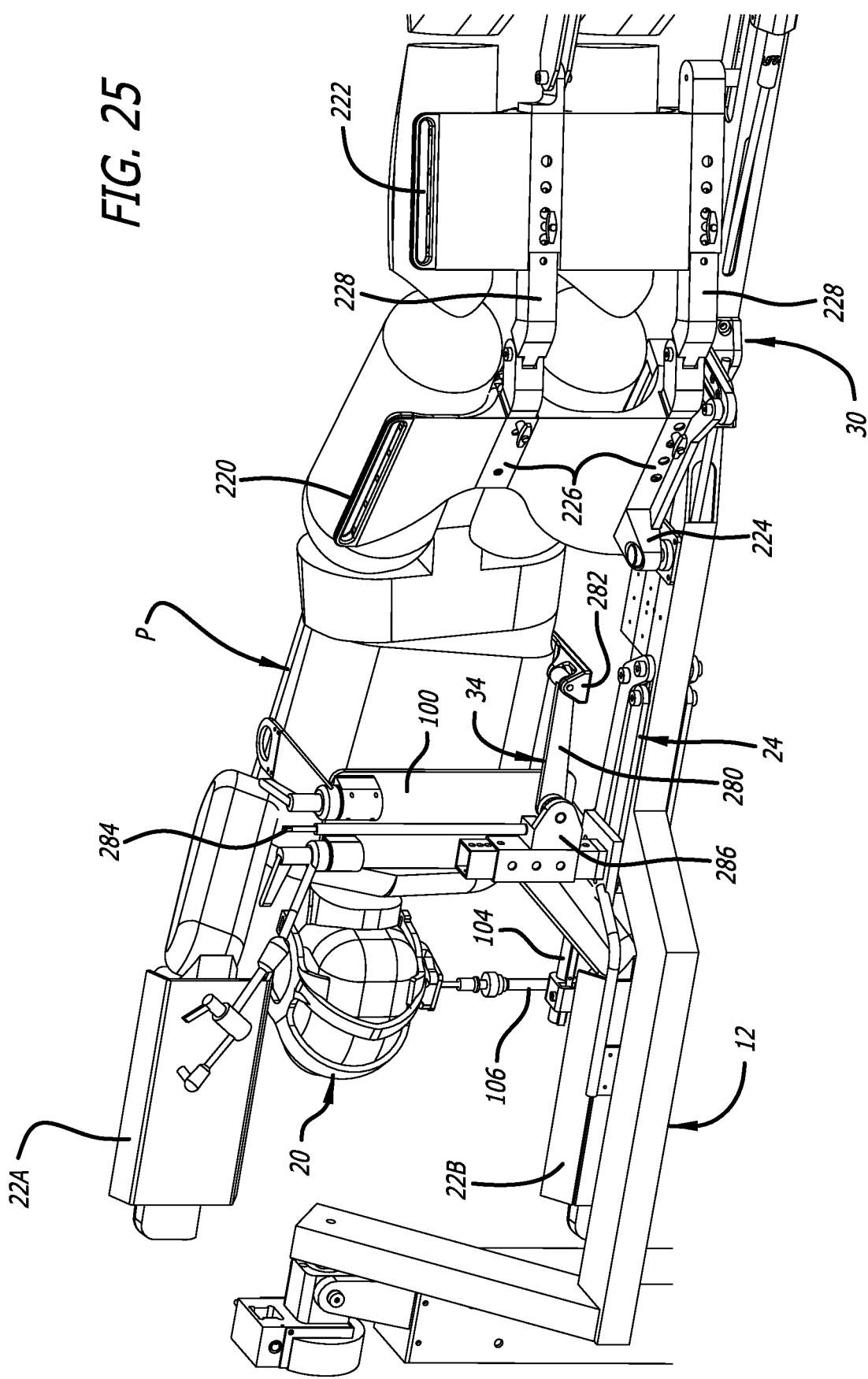
FIG. 25 is a top perspective view that illustrates portions of the surgical frame of FIG. 1 showing operation of the coronal adjustment assembly.

As depicted in FIGS. 18 and 25, for example, a first support strut 224 and second support struts 226 are attached to the thigh cradle 220. Furthermore, third support struts 228 are attached to the lower leg cradle 222. The first support strut 224 is pivotally attached to the offset main beam 12 via a support plate 230 and a pin 232, and the second support struts 226 are pivotally attached to the third support struts 228 via pins 234. The pins 234 extend through angled end portions 236 and 238 of the second and third support struts 226 and 228, respectively. Furthermore, the lengths of second and third support struts 226 and 228 are adjustable to facilitate expansion and contraction of the lengths thereof.

To accommodate patients with different torso lengths, the position of the thigh cradle 220 can be adjustable by moving the support plate 230 along the offset main beam 12. Furthermore, to accommodate patients with different thigh and lower leg lengths, the lengths of the second and third support struts 226 and 228 can be adjusted.

Figure 19:
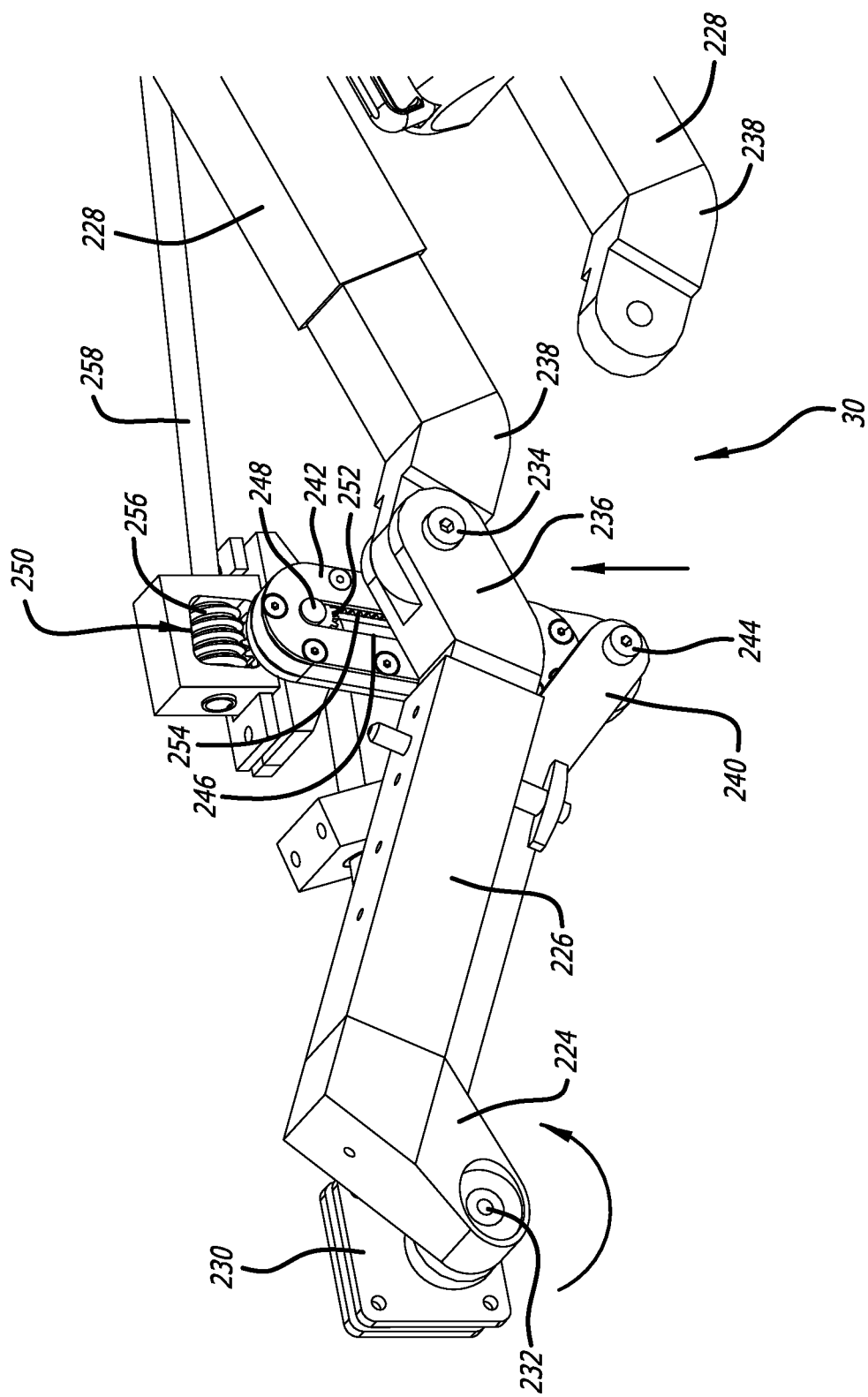
FIG. 19 is an enlarged perspective view that illustrates componentry of the pelvic-tilt mechanism.
Figure 20:
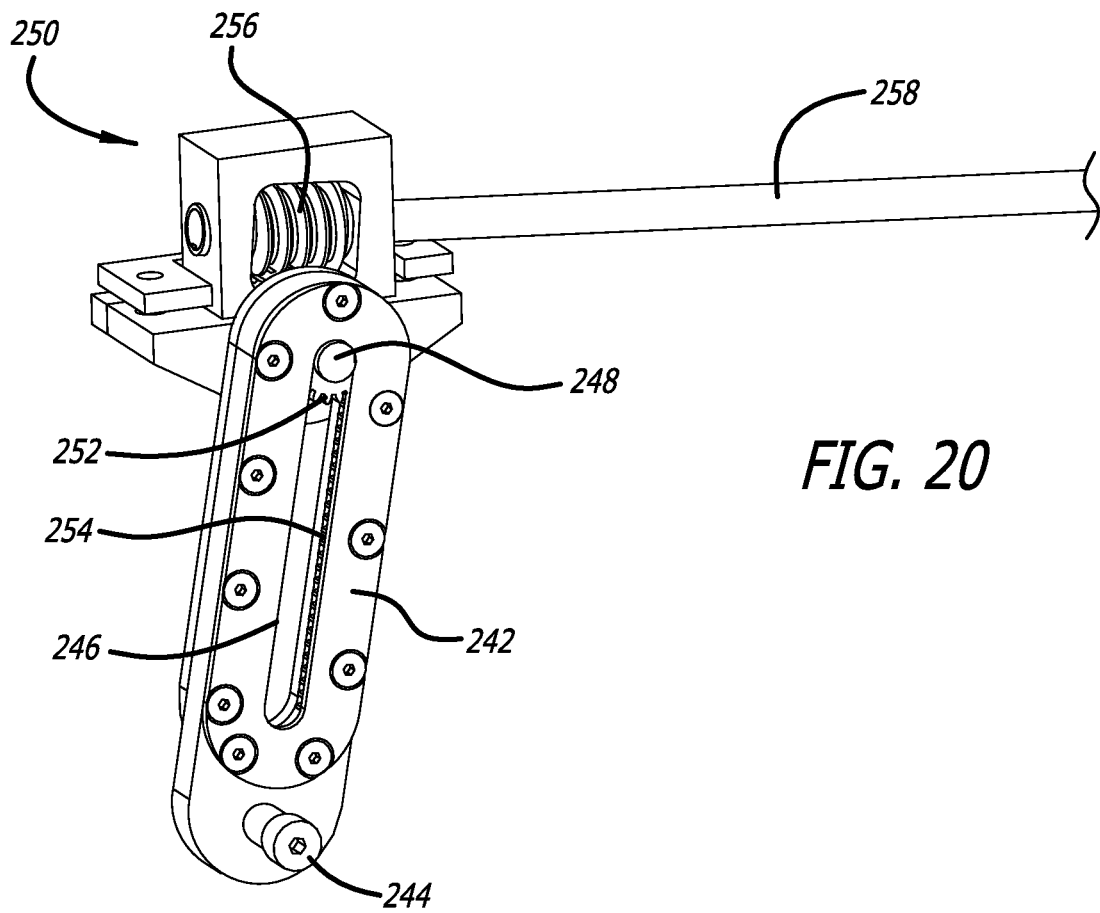
FIG. 20 is an enlarged perspective view that illustrates a captured rack and a worm gear assembly of the componentry of the pelvic-tilt mechanism.
Figure 21:
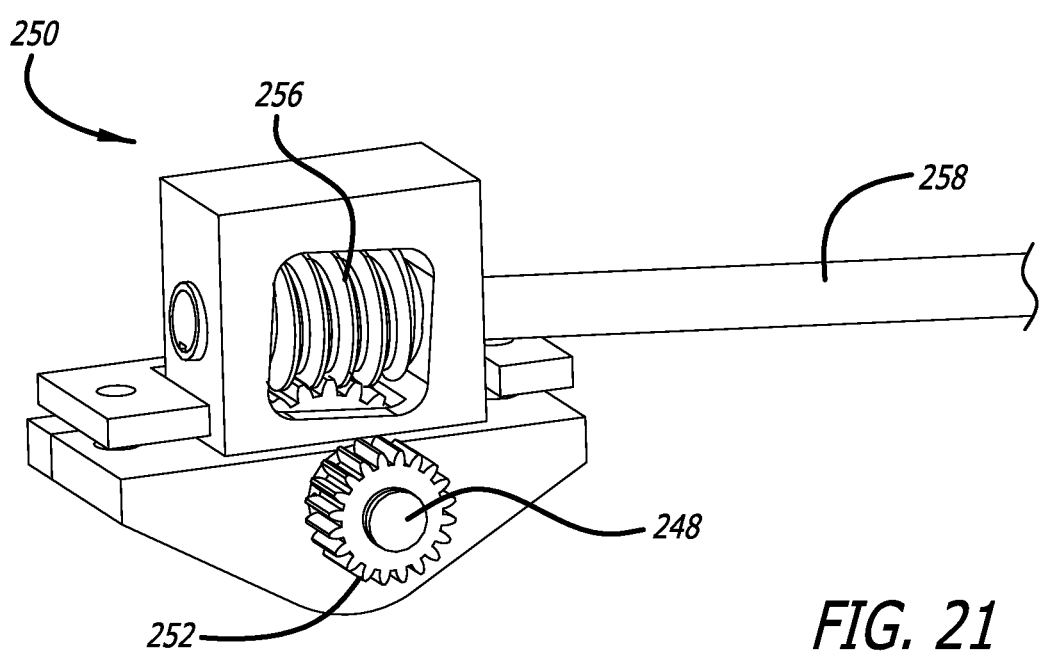
FIG. 21 is an enlarged perspective view that illustrates the worm gear assembly of FIG. 20.

To control the pivotal angle between the second and third support struts 226 and 228 (and hence, the pivotal angle between the thigh cradle 220 and lower leg cradle 222), a link 240 is pivotally connected to a captured rack 242 via a pin 244. The captured rack 242 includes an elongated slot 246, through which is inserted a worm gear shaft 248 of a worm gear assembly 250. The worm gear shaft 248 is attached to a gear 252 provided on the interior of the captured rack 242. The gear 252 contacts teeth 254 provided inside the captured rack 242, and rotation of the gear 252 (via contact with the teeth 254) causes motion of the captured rack 242 upwardly and downwardly. The worm gear assembly 250, as depicted in FIGS. 19-21, for example, includes worm gears 256 which engage a drive shaft 258, and which are connected to the worm gear shaft 248.

The worm gear assembly 250 also is configured to function as a brake, which prevents unintentional movement of the sagittal adjustment assembly 28. Rotation of the drive shaft 258 causes rotation of the worm gears 256, thereby causing reciprocal vertical motion of the captured rack 242. The vertical reciprocal motion of the captured rack 242 causes corresponding motion of the link 240, which in turn pivots the second and third support struts 226 and 228 to correspondingly pivot the thigh cradle 220 and lower leg cradle 222. A servomotor (not shown) interconnected with the drive shaft 258 can be computer controlled and/or operated by the operator of the surgical frame 10 to facilitate controlled reciprocal motion of the captured rack 242.

The sagittal adjustment assembly 28 also includes the leg adjustment mechanism 32 facilitating articulation of the thigh cradle 220 and the lower leg cradle 222 with respect to one another. In doing so, the leg adjustment mechanism 32 accommodates the lengthening and shortening of the patient's legs during bending thereof. As depicted in FIG. 17, for example, the leg adjustment mechanism 32 includes a first bracket 260 and a second bracket 262 attached to the lower leg cradle 222. The first bracket 260 is attached to a first carriage portion 264, and the second bracket 262 is attached to a second carriage portion 266 via pins 270 and 272, respectively. The first carriage portion 264 is slidable within third portion 94 of the rear portion 74 of the offset main beam 12, and the second carriage portion 266 is slidable within the first portion 90 of the rear portion 74 of the offset main beam 12. An elongated slot 274 is provided in the first portion 90 to facilitate engagement of the second bracket 262 and the second carriage portion 266 via the pin 272. As the thigh cradle 220 and the lower leg cradle 222 articulate with respect to one another (and the patient's legs bend accordingly), the first carriage 264 and the second carriage 266 can move accordingly to accommodate such movement.

Figure 22:
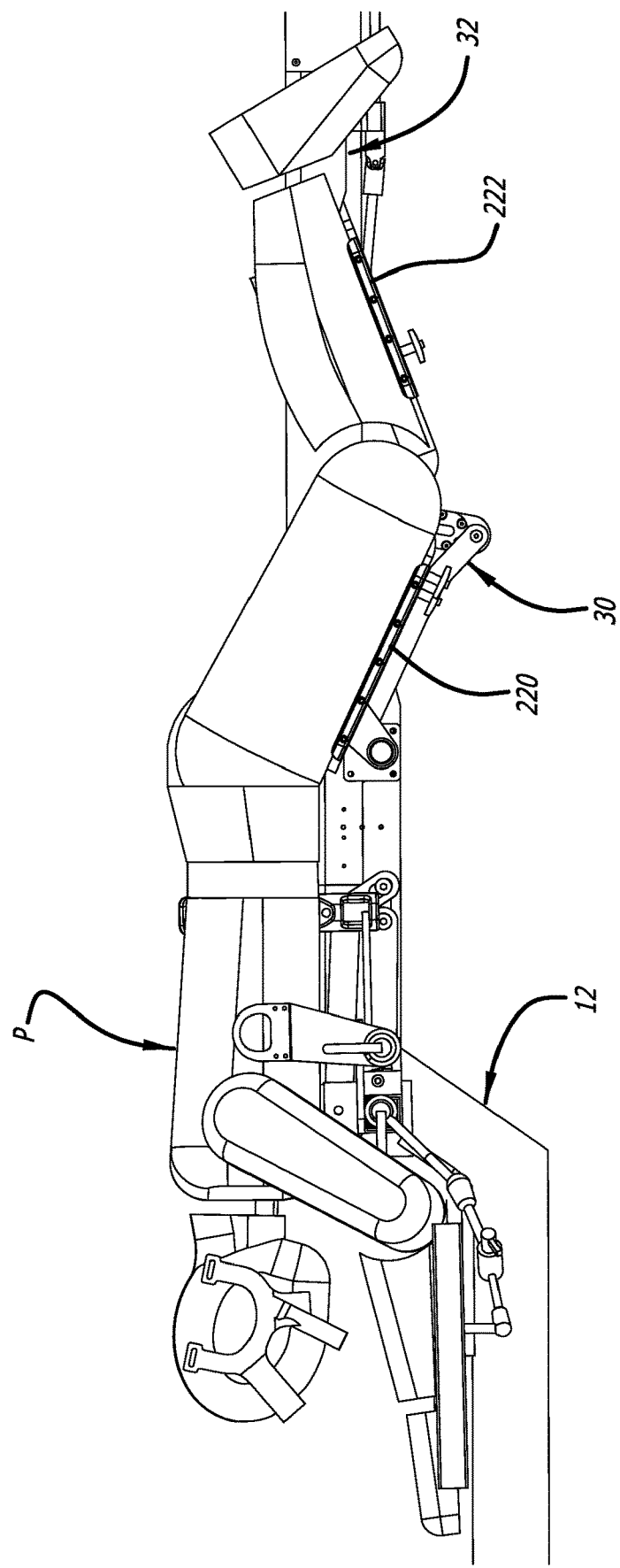
FIG. 22 is a side elevational view that illustrates portions of the surgical frame of FIG. 1 showing the patient positioned thereon and the pelvic-tilt mechanism of the sagittal adjustment assembly in the flexed position.
Figure 23:
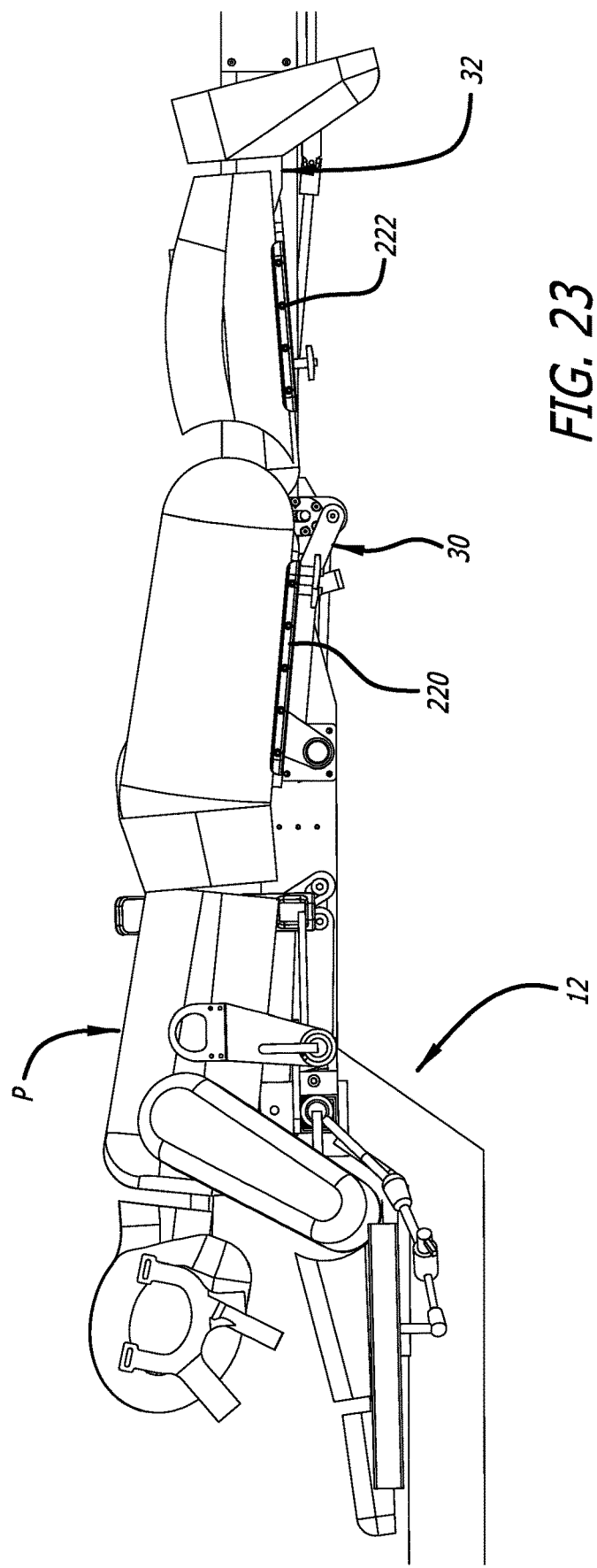
FIG. 23 is another side elevational view that illustrates portions of the surgical frame of FIG. 1 showing the patient positioned thereon and the pelvic-tilt mechanism of the sagittal adjustment assembly in the fully extended position.

The pelvic-tilt mechanism 30 is movable between a flexed position and a fully extended position. As depicted in FIG. 22, in the flexed position, the lumbar spine is hypo-lordosed. This opens the posterior boundaries of the lumbar vertebral bodies and allows for easier placement of any interbody devices. The lumbar spine stretches slightly in this position. As depicted in FIG. 23, in the extended position, the lumbar spine is lordosed. This compresses the lumbar spine. When posterior fixation devices, such as rods and screws, are placed, optimal sagittal alignment can be achieved. During sagittal alignment, little to negligible angle change occurs between the thighs and the pelvis. The pelvic-tilt mechanism 30 also can hyper-extend the hips as a means of lordosing the spine, in addition to tilting the pelvis. One of ordinary skill will recognize, however, that straightening the patient's legs does not lordose the spine. Leg straightening is a consequence of rotating the pelvis while maintaining a fixed angle between the pelvis and the thighs.

The sagittal adjustment assembly 28, having the configuration described above, further includes an ability to compress and distract the spine dynamically while in the lordosed or flexed positions. The sagittal adjustment assembly 28 also includes safety stops (not shown) to prevent over-extension or compression of the patient, and sensors (not shown) programmed to send patient position feedback to the safety stops.

Figure 24:
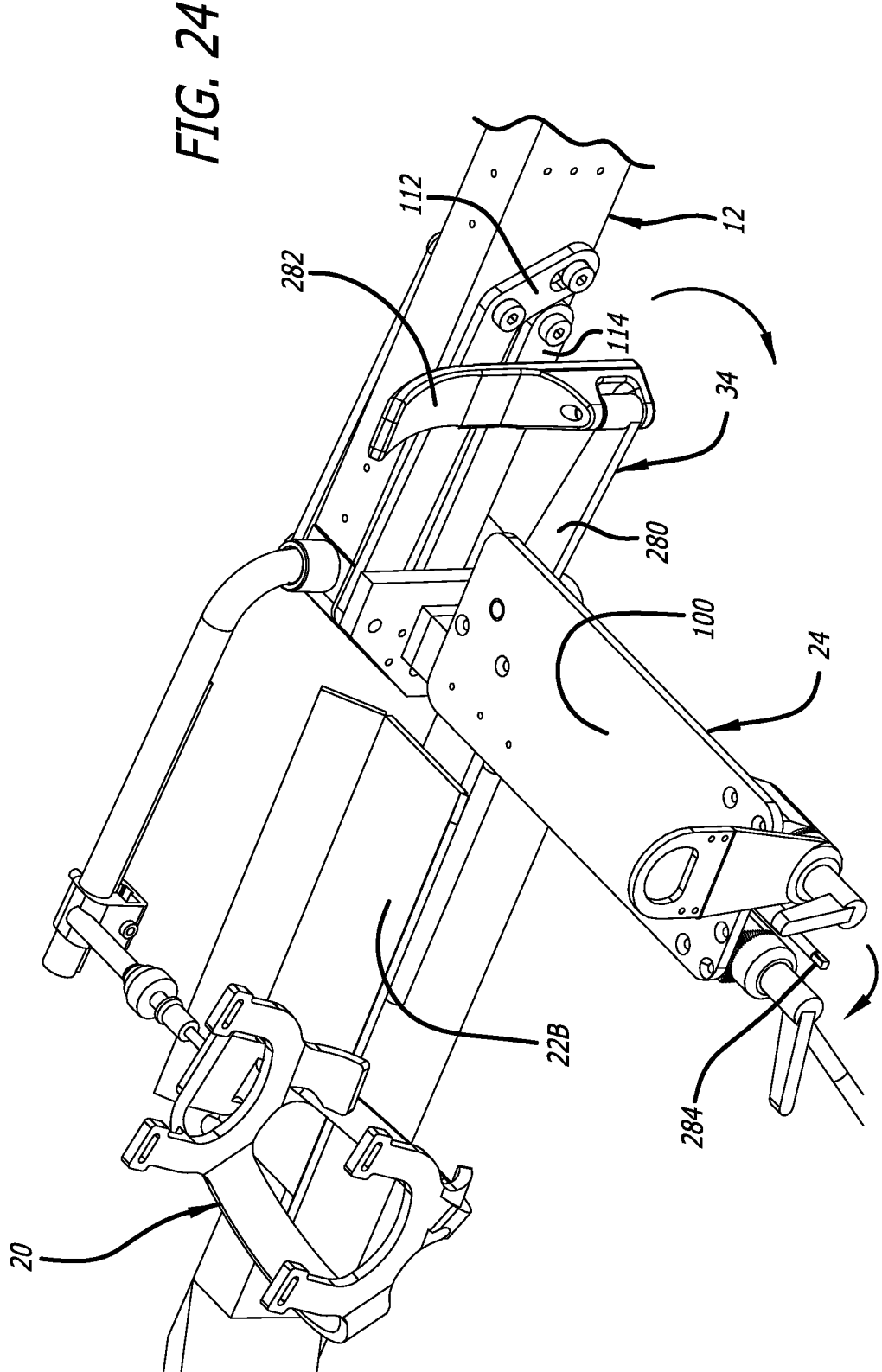
FIG. 24 is an enlarged top perspective view that illustrates portions of the surgical frame of FIG. 1 showing a coronal adjustment assembly.
Figure 26:
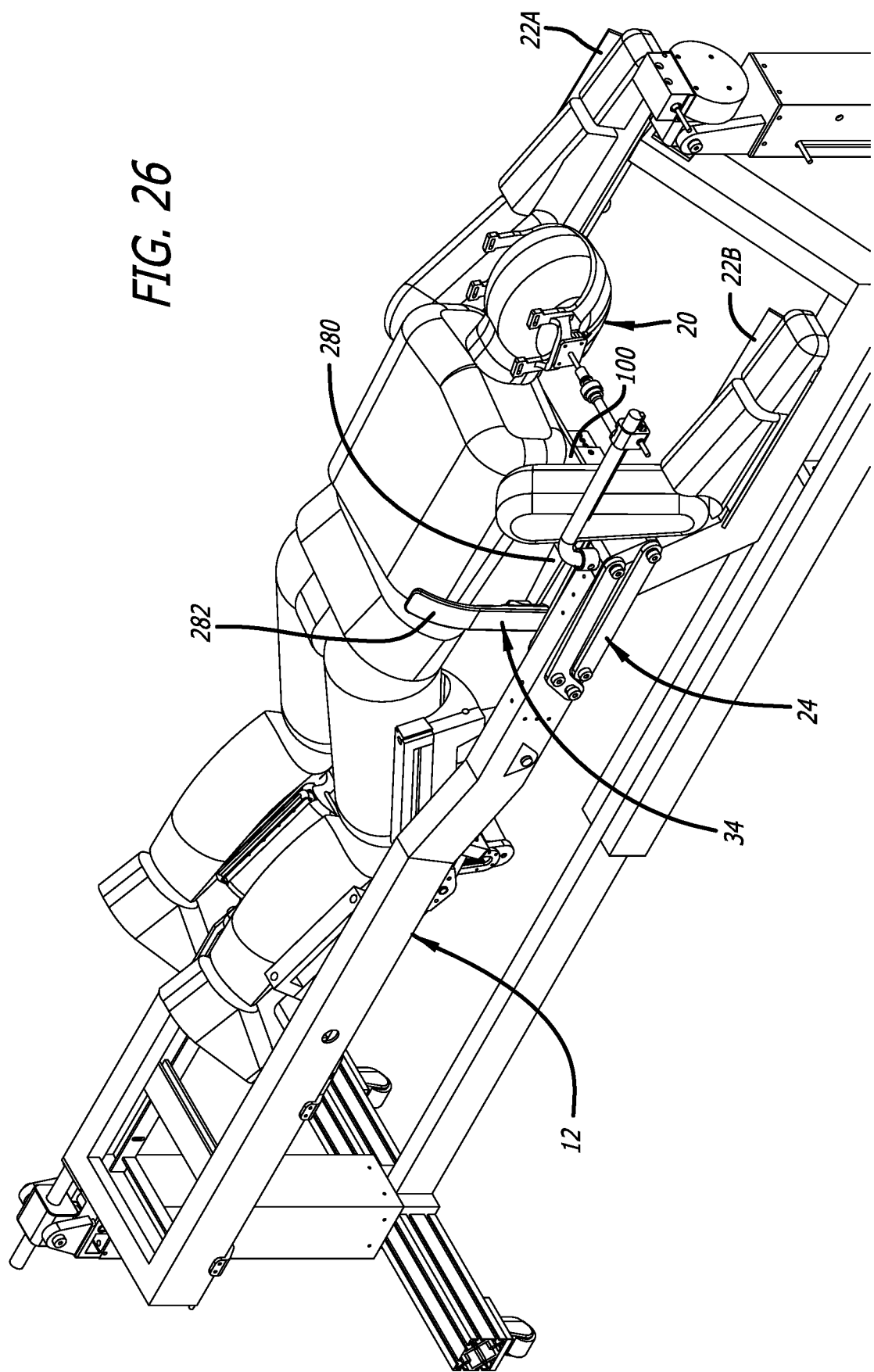
FIG. 26 is a top perspective view that illustrates a portion of the surgical frame of FIG. 1 showing operation of the coronal adjustment assembly.
Figure 27:
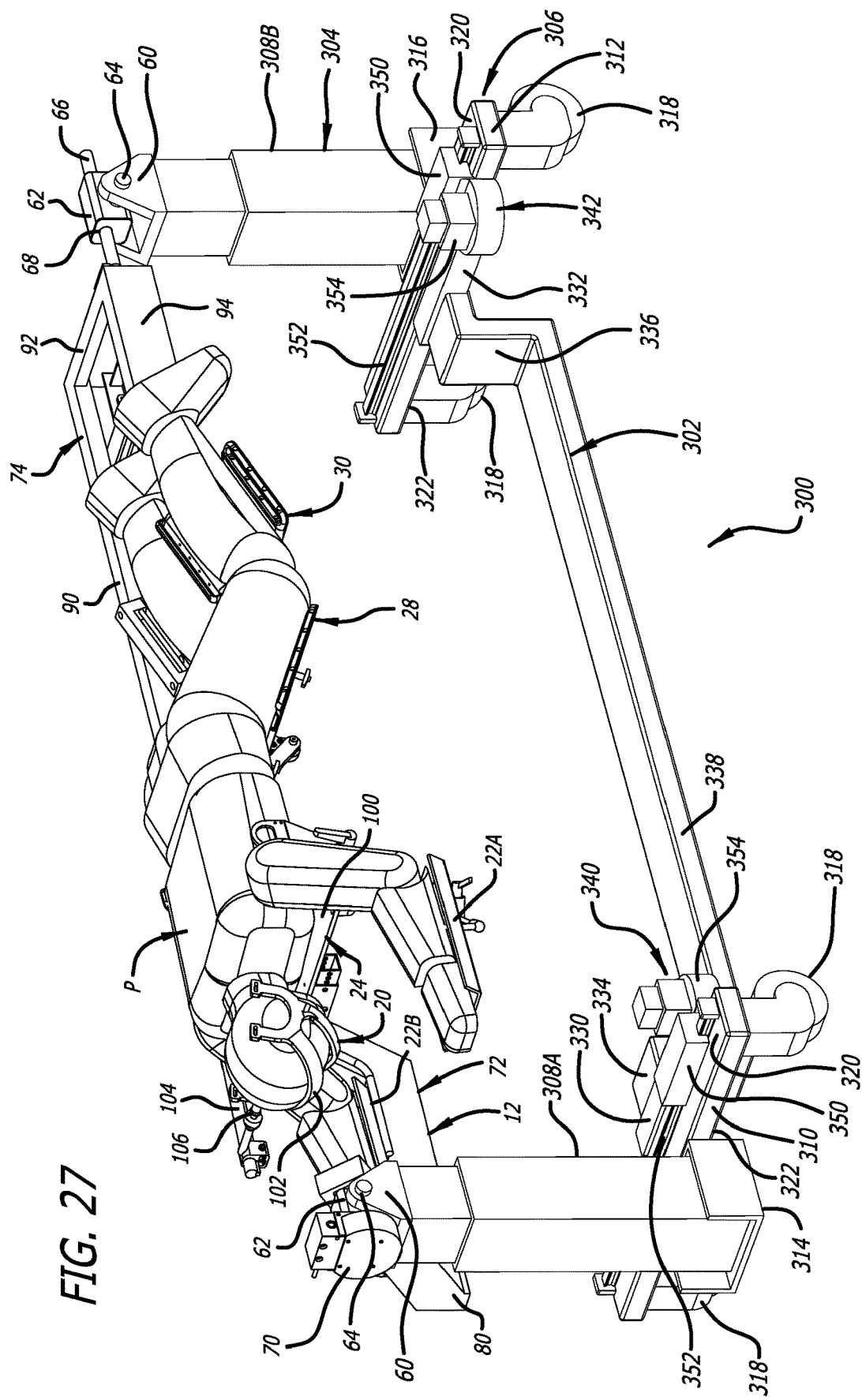
FIG. 27 is a top perspective view that illustrates a surgical frame with the patient positioned thereon in a prone position showing a translating beam thereof in a first position.

As depicted in FIGS. 24-26, for example, the coronal adjustment assembly 34 is configured to support and manipulate the patient's torso, and further to correct a spinal deformity, including but not limited to a scoliotic spine. As depicted in FIGS. 24-26, for example, the coronal adjustment assembly 34 includes a lever 280 linked to an arcuate radio-lucent paddle 282. As depicted in FIGS. 24 and 25, for example, a rotatable shaft 284 is linked to the lever 280 via a transmission 286, and the rotatable shaft 284 projects from an end of the chest support plate 100. Rotation of the rotatable shaft 284 is translated by the transmission 286 into rotation of the lever 280, causing the paddle 282, which is linked to the lever 280, to swing in an arc. Furthermore, a servomotor (not shown) interconnected with the rotatable shaft 284 can be computer controlled and/or operated by the operator of the surgical frame 10 to facilitate controlled rotation of the lever 280.

As depicted in FIG. 24, for example, adjustments can be made to the position of the paddle 282 to manipulate the torso and straighten the spine. As depicted in FIG. 25, when the offset main beam 12 is positioned such that the patient P is positioned in a lateral position, the coronal adjustment assembly 34 supports the patient's torso. As further depicted in FIG. 26, when the offset main beam 12 is positioned such that the patient P is positioned in a prone position, the coronal adjustment assembly 34 can move the torso laterally, to correct a deformity, including but not limited to a scoliotic spine. When the patient is strapped in via straps (not shown) at the chest and legs, the torso is relatively free to move and can be manipulated. Initially, the paddle 282 is moved by the lever 280 away from the offset main beam 12. After the paddle 282 has been moved away from the offset main beam 12, the torso can be pulled with a strap towards the offset main beam 12. The coronal adjustment assembly 34 also includes safety stops (not shown) to prevent over-extension or compression of the patient, and sensors (not shown) programmed to send patient position feedback to the safety stops.

A preferred embodiment of a surgical frame incorporating a translating beam is generally indicated by the numeral 300 in FIGS. 27-30. Like the surgical frame 10, the surgical frame 300 serves as an exoskeleton to support the body of the patient P as the patient's body is manipulated thereby. In doing so, the surgical frame 300 serves to support the patient P such that the patient's spine does not experience unnecessary stress/torsion.

The surgical frame 300 includes translating beam 302 that is generally indicated by the numeral 302 in FIGS. 27-30. The translating beam 302 is capable of translating motion affording it to be positioned and repositioned with respect to portions of the remainder of the surgical frame 300. As discussed below, the positioning and repositioning of the translating beam 302, for example, affords greater access to a patient receiving area A defined by the surgical frame 300, and affords greater access to the patient P by a surgeon and/or a surgical assistant (generally indicated by the letter S in FIG. 30) via access to either of the lateral sides $L_1$ and $L_2$ (FIG. 30) of the surgical frame 300.

As discussed below, by affording greater access to the patient receiving area A, the surgical frame 300 affords transfer of the patient P from and to a surgical table/gurney. Using the surgical frame 300, the surgical table/gurney can be conventional, and there is no need to lift the surgical table/gurney over portions of the surgical frame 300 to afford transfer of the patient P thereto.

The surgical frame 300 is configured to provide a relatively minimal amount of structure adjacent the patient's spine to facilitate access thereto and to improve the quality of imaging available before, during, and even after surgery. Thus, the workspace of a surgeon and/or a surgical assistant and imaging access are thereby increased. The workspace, as discussed below, can be further increased by positioning and repositioning the translating beam 302. Furthermore, radio-lucent or low magnetic susceptibility materials can be used in constructing the structural components adjacent the patient's spine in order to further enhance imaging quality.

The surgical frame 300, as depicted in FIGS. 27-30, is similar to the surgical frame 10 except that surgical frame 300 includes a support structure 304 having a support platform 306 incorporating the translating beam 302. The surgical frame 300 incorporates the offset main beam 12 and the features associated therewith from the surgical table 300. As such, the element numbering used to describe the surgical frame 10 is also applicable to portions of the surgical frame 300.

Rather than including the cross member 44, and the horizontal portions 46 and the vertical portions 48 of the first and second support portions 40 and 42, the support structure 304 includes the support platform 306, a first vertical support post 308A, and a second vertical support post 308B. As depicted in FIGS. 27-30, the support platform 306 extends from adjacent one longitudinal end to adjacent the other longitudinal end of the surgical frame 300, and the support platform 306 supports the first vertical support post 308A at the one longitudinal end and supports the second vertical support post 308B at the other longitudinal end.

As depicted in FIGS. 27-30, the support platform 306 (in addition to the translating beam 302) includes a first end member 310, a second end member 312, a first support bracket 314, and a second support bracket 316. Casters 318 are attached to the first and second end members 310 and 312. The first end member 310 and the second end member 312 each include an upper surface 320 and a lower surface 322. The casters 318 can be attached to the lower surface of each of the first and second end members 310 and 312 at each end thereof, and the casters 318 can be spaced apart from one another to afford stable movement of the surgical frame 300. Furthermore, the first support bracket 314 supports the first vertical support post 308A, and the second support bracket 316 supports the vertical second support post 308B.

The translating beam 302 is interconnected with the first and second end members 310 and 312 of the support platform 306, and as depicted in FIGS. 27-30, the translating beam 302 is capable of movement with respect to the first and second end members 310 and 312. The translating beam 302 includes a first end member 330, a second end member 332, a first L-shaped member 334, a second L-shaped member 336, and a cross member 338. The first L-shaped member 334 is attached to the first end member 330 and the cross member 338, and the second L-shaped member 336 is attached to the second end member 332 and the cross member 338. Portions of the first and second L-shaped members 334 and 336 extend downwardly relative to the first and second end members 330 and 332 such that the cross member 338 is positioned vertically below the first and second end member 330 and 332. The vertical position of the cross member 338 relative to the remainder of the surgical frame 300 lowers the center of gravity of the surgical frame 300, and in doing so, serves in adding to the stability of the surgical frame 300.

The translating beam 302, as discussed above, is capable of being positioned and repositioned with respect to portions of the remainder of the surgical frame 300. To that end, the support platform 306 includes a first translation mechanism 340 and a second translation mechanism 342. The first translation mechanism 340 facilitates attachment between the first end members 310 and 330, and the second translation mechanism 342 facilitates attachment between the second end members 312 and 332. The first and second translation mechanism 340 and 342 also facilitate movement of the translating beam 302 relative to the first end member 310 and the second end member 312.

The first and second translation mechanisms 340 and 342 can each include a transmission 350 and a track 352 for facilitating movement of the translating beam 302. The tracks 352 are provided on the upper surface 320 of the first and second end members 310 and 312, and the transmissions 350 are interoperable with the tracks 352. The first and second transmission mechanisms 340 and 342 can each include an electrical motor 354 or a hand crank (not shown) for driving the transmissions 350. Furthermore, the transmissions 350 can include, for example, gears or wheels driven thereby for contacting the tracks 352. The interoperability of the transmissions 350, the tracks 352, and the motors 354 or hand cranks form a drive train for moving the translating beam 302. The movement afforded by the first and second translation mechanism 340 and 342 allows the translating beam 302 to be positioned and repositioned relative to the remainder of the surgical frame 300.

The surgical frame 300 can be configured such that operation of the first and second translation mechanism 340 and 342 can be controlled by an operator such as a surgeon and/or a surgical assistant. As such, movement of the translating beam 302 can be effectuated by controlled automation. Furthermore, the surgical frame 300 can be configured such that movement of the translating beam 302 automatically coincides with the rotation of the offset main beam 12. By tying the position of the translating beam 302 to the rotational position of the offset main beam 12, the center of gravity of the surgical frame 300 can be maintained in positions advantageous to the stability thereof.

During use of the surgical frame 300, access to the patient receiving area A and the patient P can be increased or decreased by moving the translating beam 302 between the lateral sides $L_1$ and $L_2$ of the surgical frame 300. Affording greater access to the patient receiving area A facilitates transfer of the patient P between the surgical table/gurney and the surgical frame 300. Furthermore, affording greater access to the patient P facilitates ease of access by a surgeon and/or a surgical assistant to the surgical site on the patient P.

Figure 28:
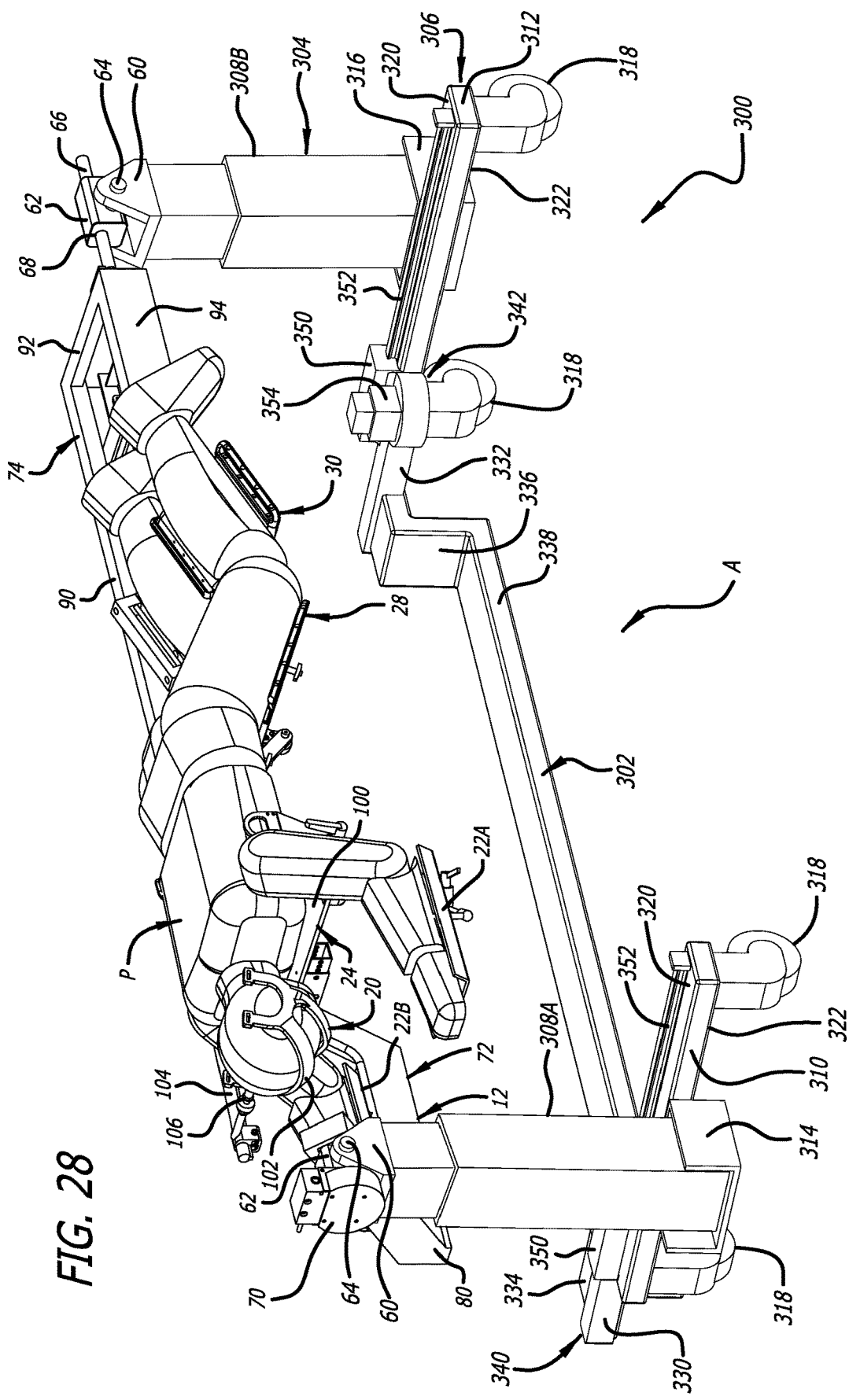
FIG. 28 is another top perspective view that illustrates the surgical frame of FIG. 27 with the patient in a prone position showing the translating beam thereof in a second position.
Figure 29:
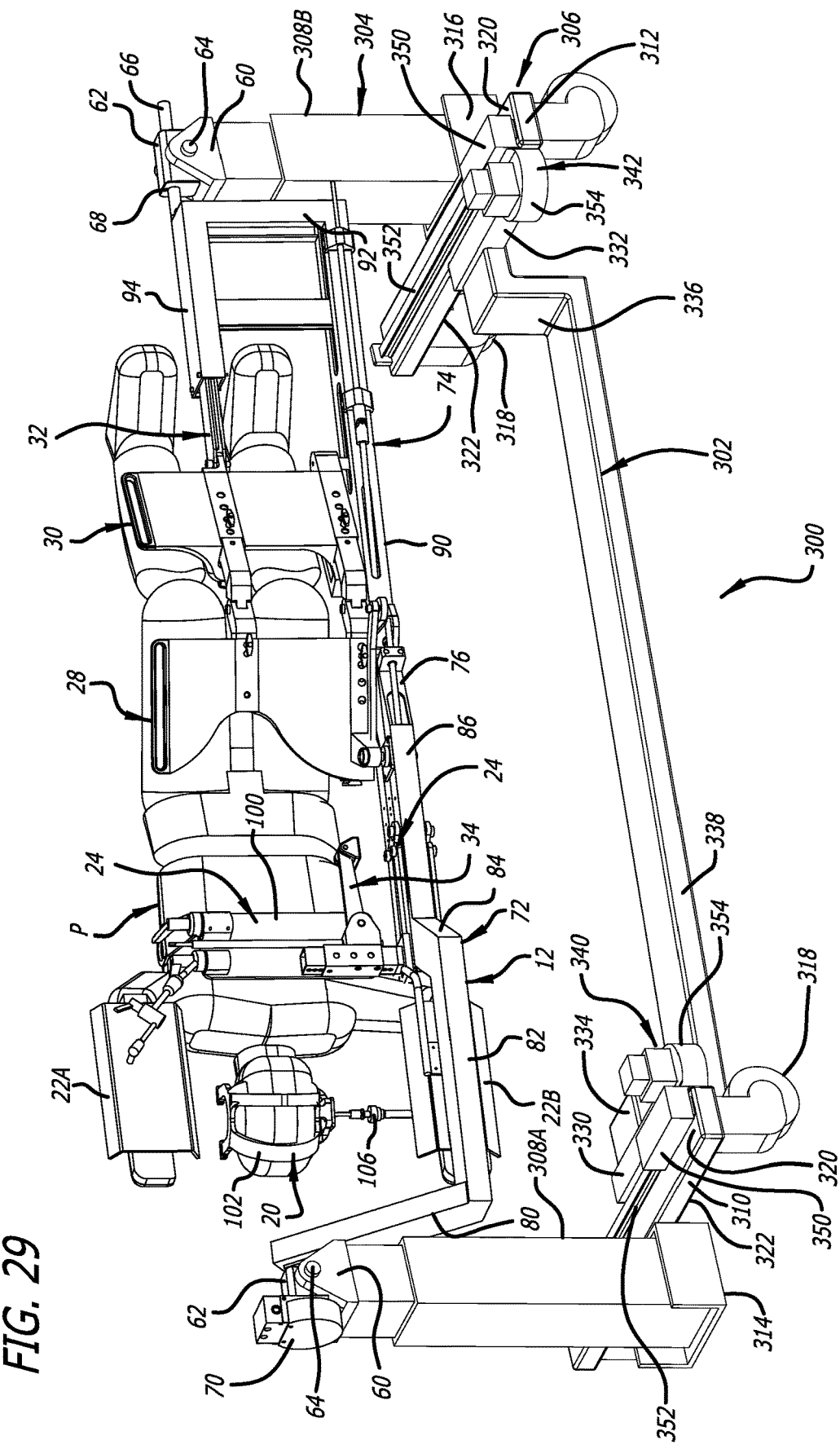
FIG. 29 is yet another top perspective view that illustrates the surgical frame of FIG. 27 with the patient in a lateral position showing the translating beam thereof in a third position.
Figure 30:
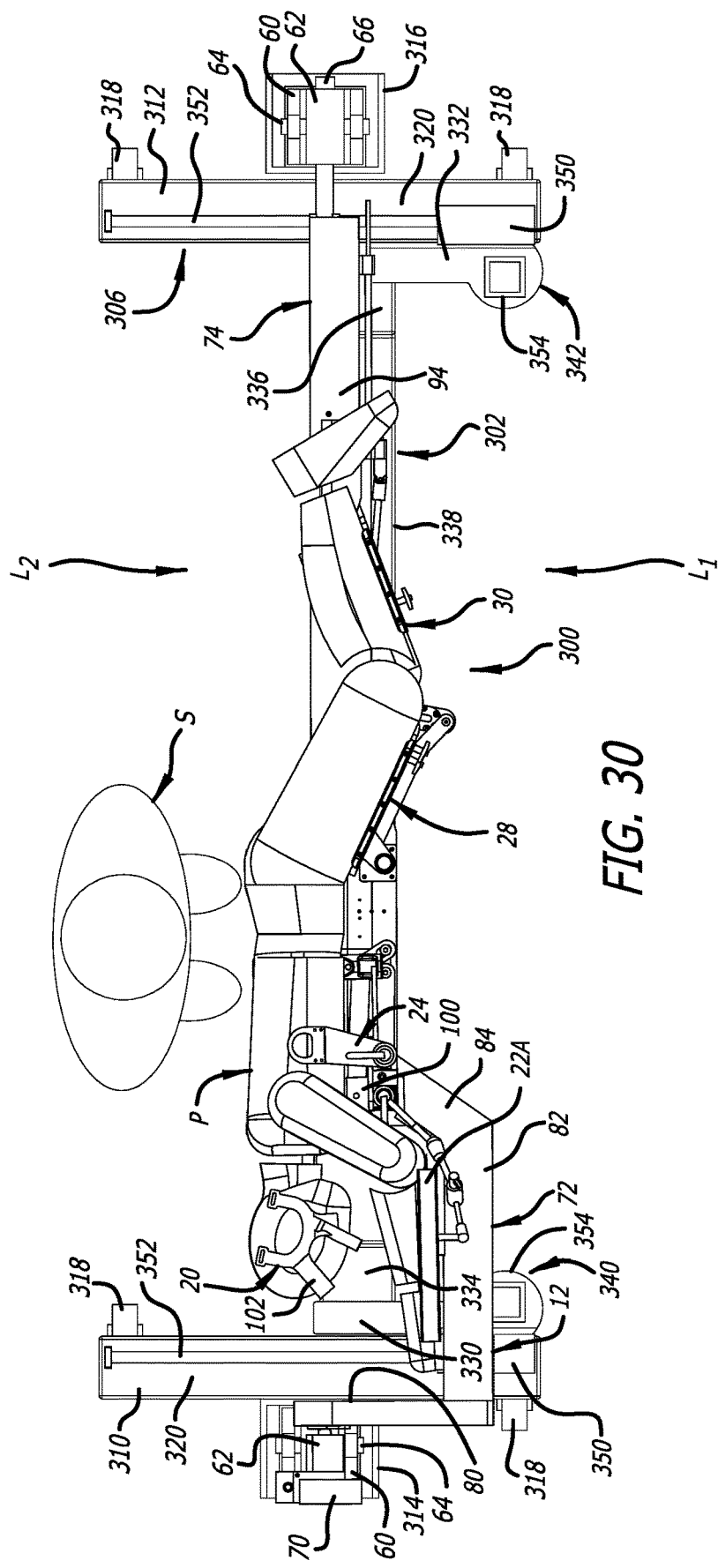
FIG. 30 is top plan view that illustrates the surgical frame of FIG. 27 with the patient in a lateral position showing the translating beam thereof in the third position.

The translating beam 302 is moveable using the first and second translation mechanisms 340 and 342 between a first terminal position (FIG. 28) and a second terminal position (FIGS. 29 and 30). The translating beam 302 is positionable at various positions (FIG. 27) between the first and second terminal positions. When the translating beam 302 is in the first terminal position, as depicted in FIG. 28, the translating beam 302 and its cross member 338 are positioned on the lateral side $L_1$ of the surgical frame 300. Furthermore, when the translating beam 302 is in the second terminal position, as depicted in FIGS. 29 and 30, the translating beam 302 and its cross member 338 are positioned in the middle of the surgical frame 300.

With the translating beam 302 and its cross member 338 moved to be positioned at the lateral side $L_1$, the surgical table/gurney and the patient P positioned thereon can be positioned under the offset main beam 12 in the patient receiving area A to facilitate transfer of the patient P to or from the offset main beam 12. As such, the position of the translating beam 302 at the lateral side $L_1$ enlarges the patient receiving area A so that the surgical table/gurney can be received therein to allow such transfer to or from the offset main beam 12.

Furthermore, with the translating beam 302 and its cross member 338 moved to be in the middle of the surgical frame 300 (FIGS. 29 and 30), a surgeon and/or a surgical assistant can have access to the patient P from either of the lateral sides $L_1$ or $L_2$. As such, the position of the translating beam 302 in the middle of the surgical frame 300 allows a surgeon and/or a surgical assistant to get close to the patient P supported by the surgical frame 300. As depicted in FIG. 30, for example, a surgeon and/or a surgical assistant can get close to the patient P from the lateral side $L_2$ without interference from the translating beam 302 and its cross member 338. The position of the translating beam 302 can be selected to accommodate access by both a surgeon and/or a surgical assistant by avoiding contact thereof with the feet and legs of a surgeon and/or a surgical assistant.

The position of the translating beam 302 and its cross member 338 can also be changed according to the rotational position of the offset main beam 12. To illustrate, the offset main beam 12 can be rotated a full 360° before, during, and even after surgery to facilitate various positions of the patient to afford various surgical pathways to the patient's spine depending on the surgery to be performed. For example, the offset main beam 12 can be positioned by the surgical frame 300 to place the patient P in a prone position (e.g., FIGS. 27 and 28), lateral positions (e.g., FIGS. 29 and 30), and in a position 45° between the prone and lateral positions. The translating beam 302 can be positioned to accommodate the rotational position of the offset main beam 12 to aid in the stability of the surgical frame 300. For example, when the patient P is in the prone position, the translating beam 302 can preferably be moved to the center of the surgical frame 300 underneath the patient P. Furthermore, when the patient P is in one of the lateral positions, the translating beam 302 can be moved toward one of the corresponding lateral sides $L_1$ and $L_2$ of the surgical frame 300 to position underneath the patient P. Such positioning of the translating beam 302 can serve to increase the stability of the surgical frame 300.

Preferred embodiments of surgical positioning frames incorporating adjustable left-right main beams are generally indicated by the numeral 400 in FIGS. 31-58 and the numeral 600 in FIGS. 59-74. Like the surgical frames 10 and 300, the surgical frames 400 and 600 each serve as an exoskeleton to support the body of the patent P as the patient's body is manipulated thereby. In doing so, the surgical frames 400 and 600 serve to support the patient P such that the patient's spine does not experience unnecessary stress.

Figure 31:
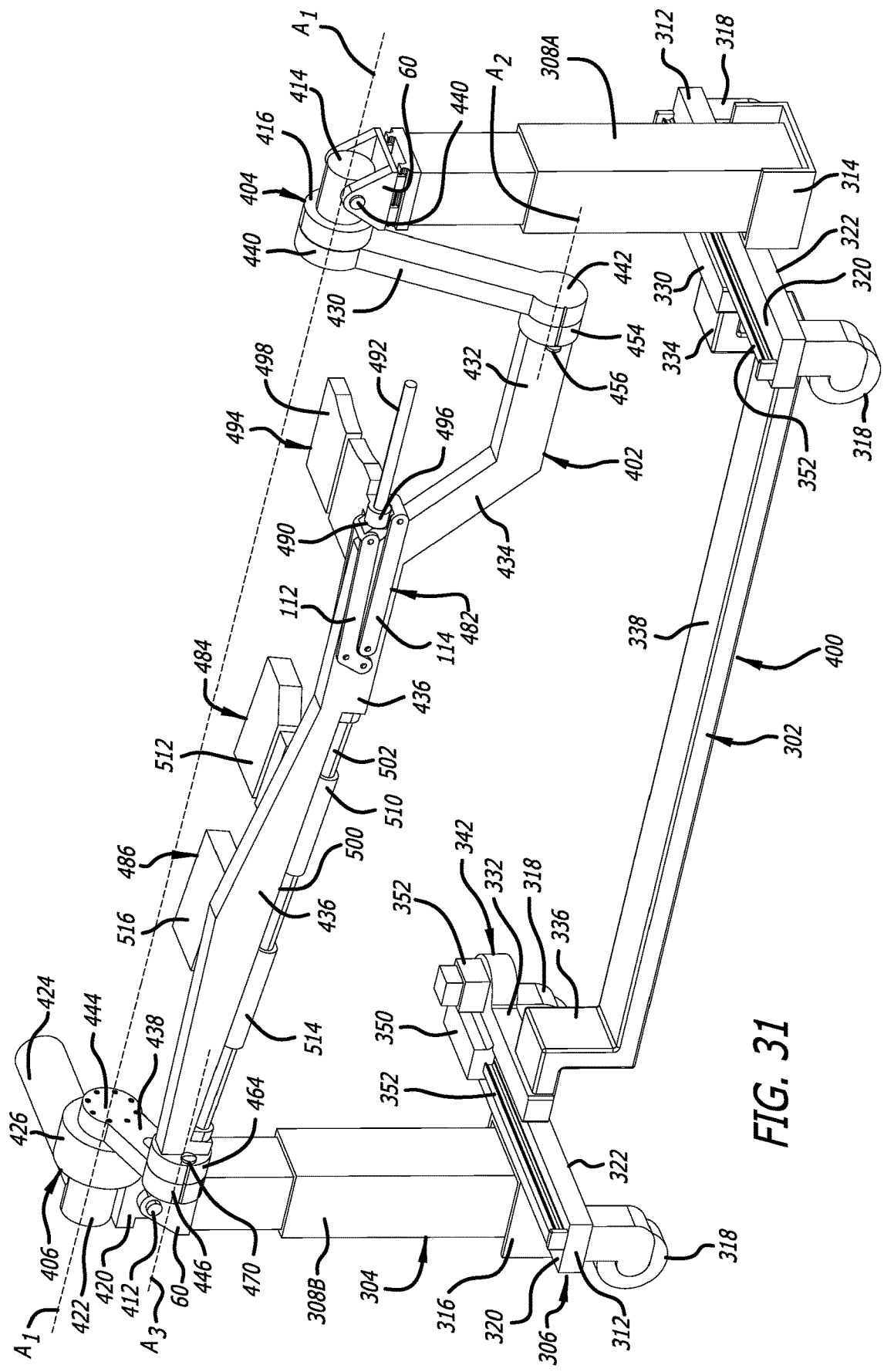
FIG. 31 is a top first side perspective view that illustrates a first embodiment of a surgical table being reconfigurable between a left configuration and a right configuration, where the surgical table is depicted in the left configuration.
Figure 32:
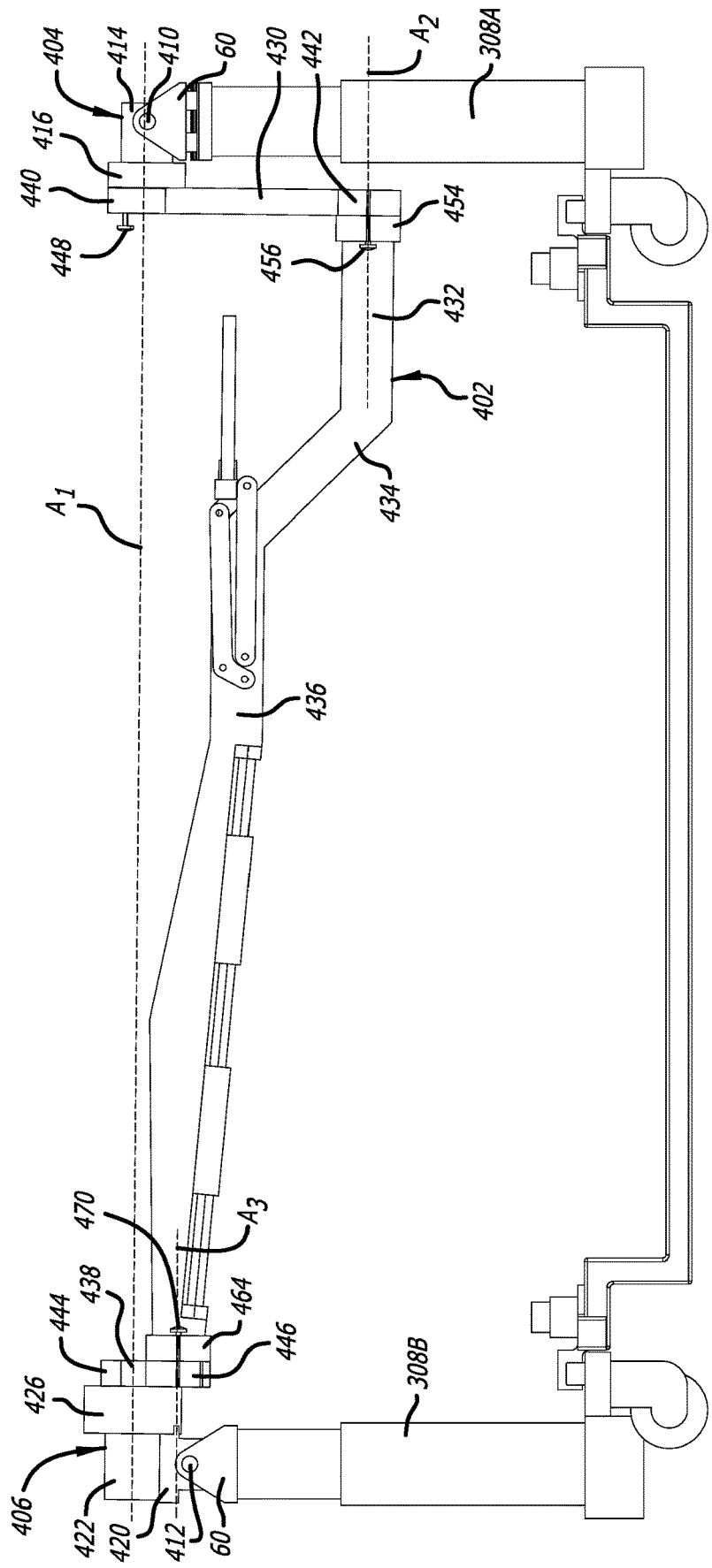
FIG. 32 is a first side elevational view that illustrates the surgical table of FIG. 31 in the left configuration.

As depicted in FIGS. 31 and 32, for example, the surgical frame 400, like the surgical frame 300, includes the support structure 304 having the support platform 306 incorporating the translating beam 302. The support structure 304 of the surgical frame 400, like the surgical frame 300, also includes the first vertical support post 308A and the second vertical support post 308B. As such, the element numbering used to describe the surgical frame 300 is also applicable to portions of the surgical frame 400.

Unlike the surgical frame 300, the surgical frame 400 includes an adjustable left-right main beam 402. The main beam 402 can be converted between a left configuration and a right configuration. The left configuration affords positioning of substantial portions of the main beam 402 adjacent the right side of the patient P to provide access to the left side of the patient. Furthermore, the right configuration affords positioning of substantial portions of the main beam 402 adjacent the left side of the patient P to provide access to the right side of the patient. The conversion between the left and right configurations allows the surgical frame 400 to be adapted to provide access to a surgical site on the left side or the right side of the patient P and/or be adapted to the preference of a surgeon.

The main beam 402 is supported at a first end by the first vertical support post 308A, the clevis 60, and a first coupler 404, and is supported at a second end by the second vertical support post 308B, the clevis 60, and a second coupler 406. The coupler 404 is pivotally attached to the clevis 60 at the first end via a pin 410, and the coupler 406 is pivotally attached to the clevis 60 at the second end via a pin 412.

Figure 33:
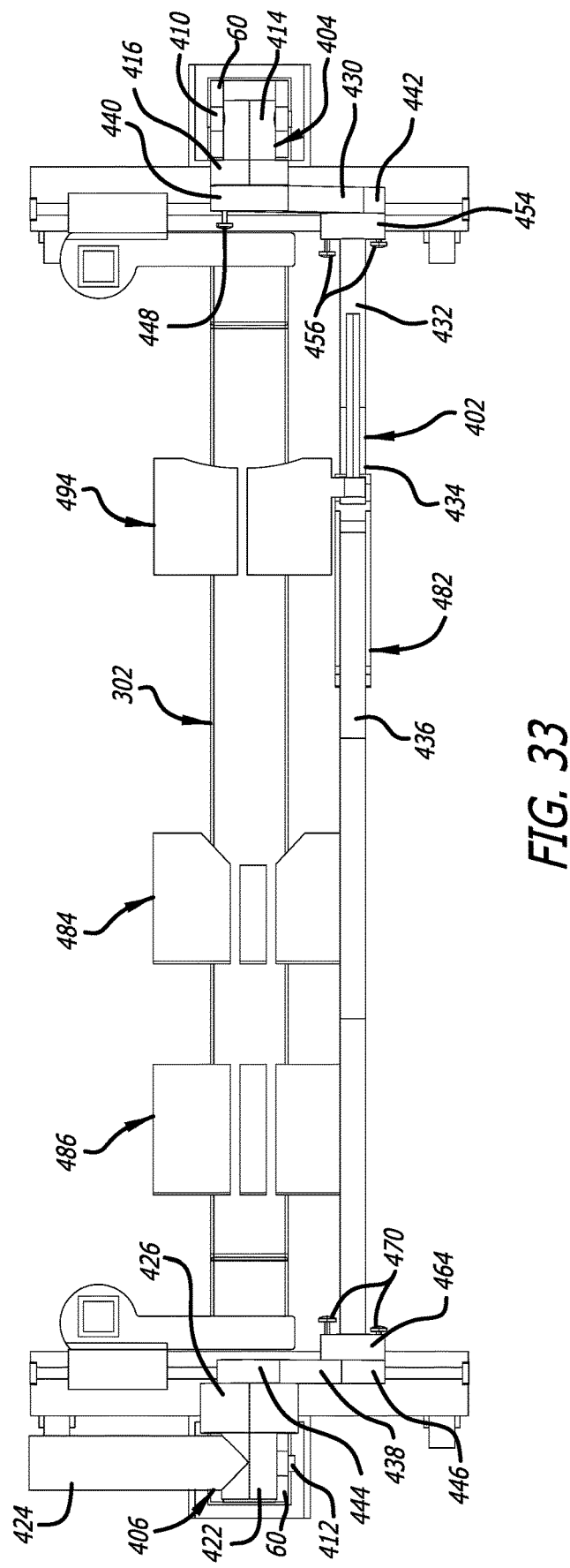
FIG. 33 is a top plan view that illustrates the surgical table of FIG. 31 in the left configuration.
Figure 34:
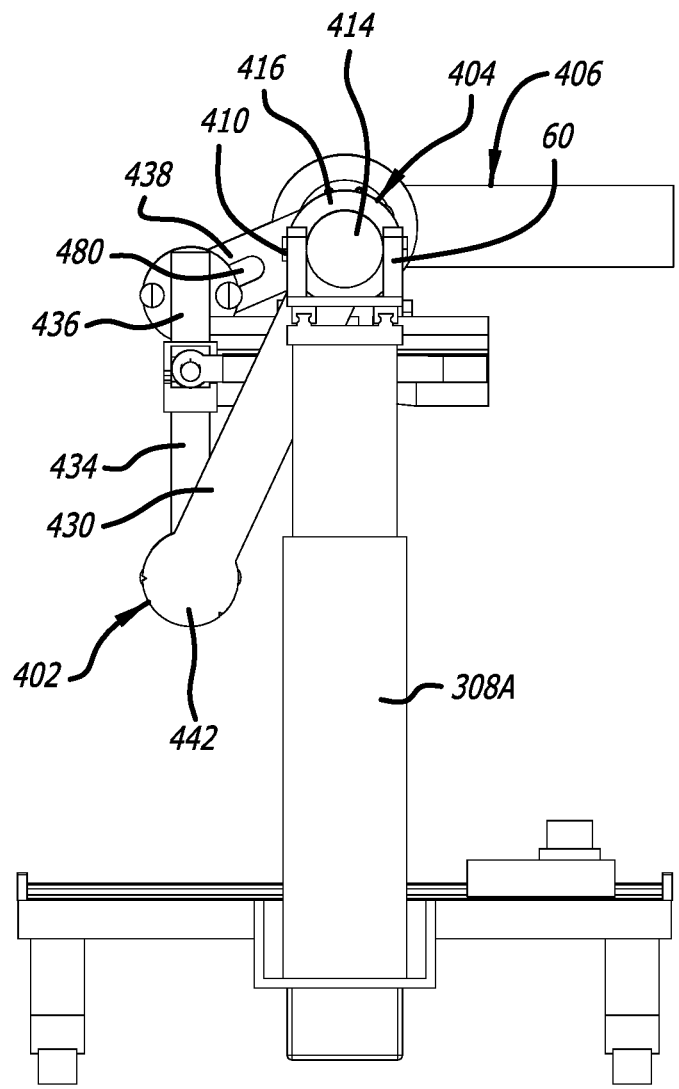
FIG. 34 is a first end elevational view that illustrates the surgical table of FIG. 31 in the left configuration.

As depicted in at least FIGS. 31-33, the first coupler 404 includes a body portion 414 that is pinned to the clevis 60 with the pin 410, and a head portion 416 that is rotatable with respect to the body portion 414. Furthermore, the second coupler 406 includes a base portion 420 that is pinned to the clevis 60 with the pin 412, a body portion 422 that includes a transmission (not shown), a motor 424 that drives the transmission in the body portion 422, and a head portion 426 that is rotatable with respect to the body portion 422 and driven rotationally by the transmission via the motor 424. The head portion 416 is engageable to a portion of the main beam 402 and the head portion 426 is engageable to another portion of the main beam 402, and the rotatability of the head portions 416 and 426 define an axis of rotation $A_1$ (FIGS. 31 and 32) of the main beam 402. The main beam 402 can be rotated using the motor 424 and the transmission interconnected with the motor 424. As such, the first coupler 404 and the second coupler 406 facilitate rotation of the main beam 402 and the patient P supported thereby.

Figure 35:
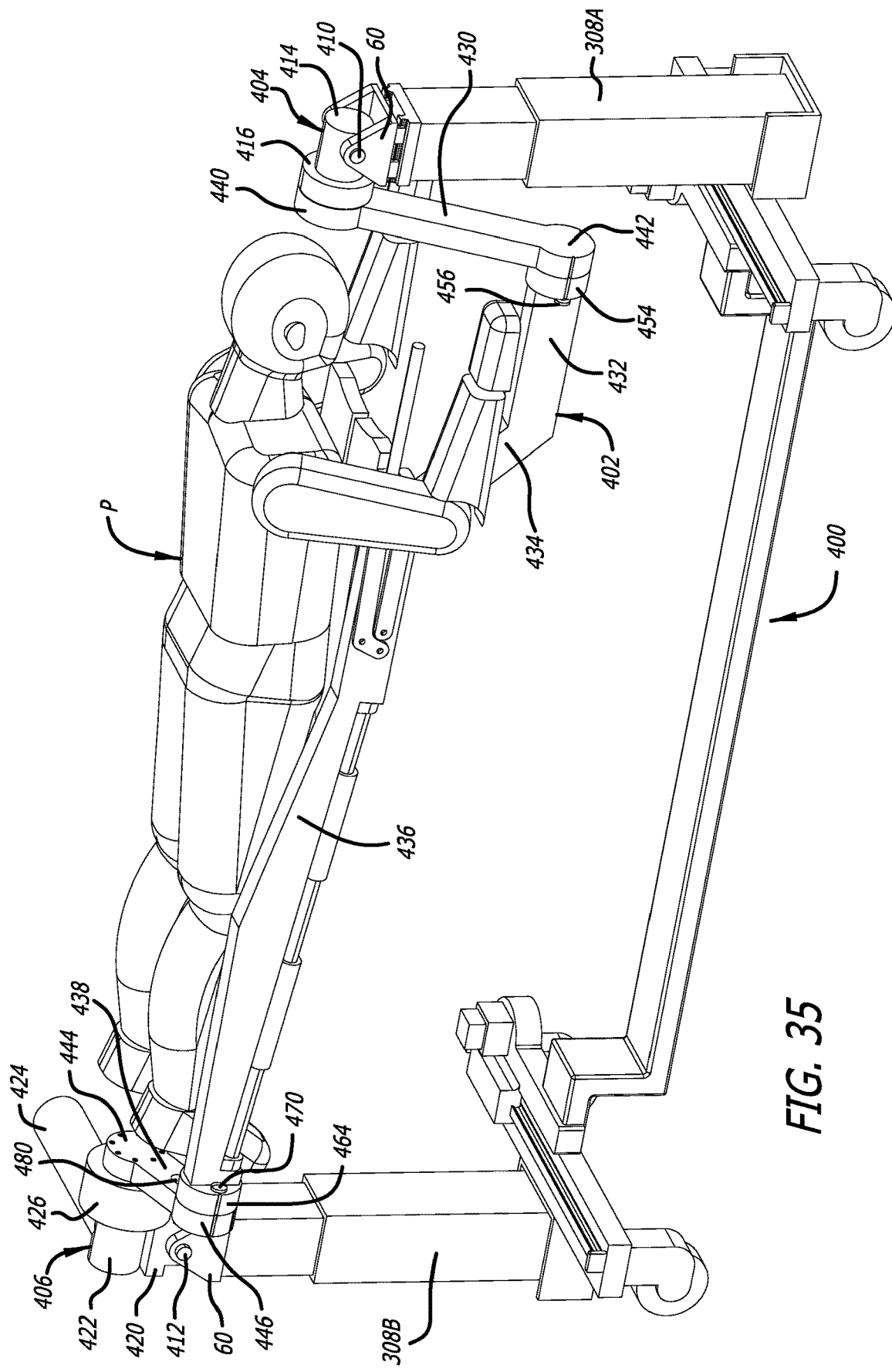
FIG. 35 is a top first side perspective view that illustrates the surgical table of FIG. 31 in the left configuration with a patient being supported on a main beam thereof in a prone position.
Figure 36:
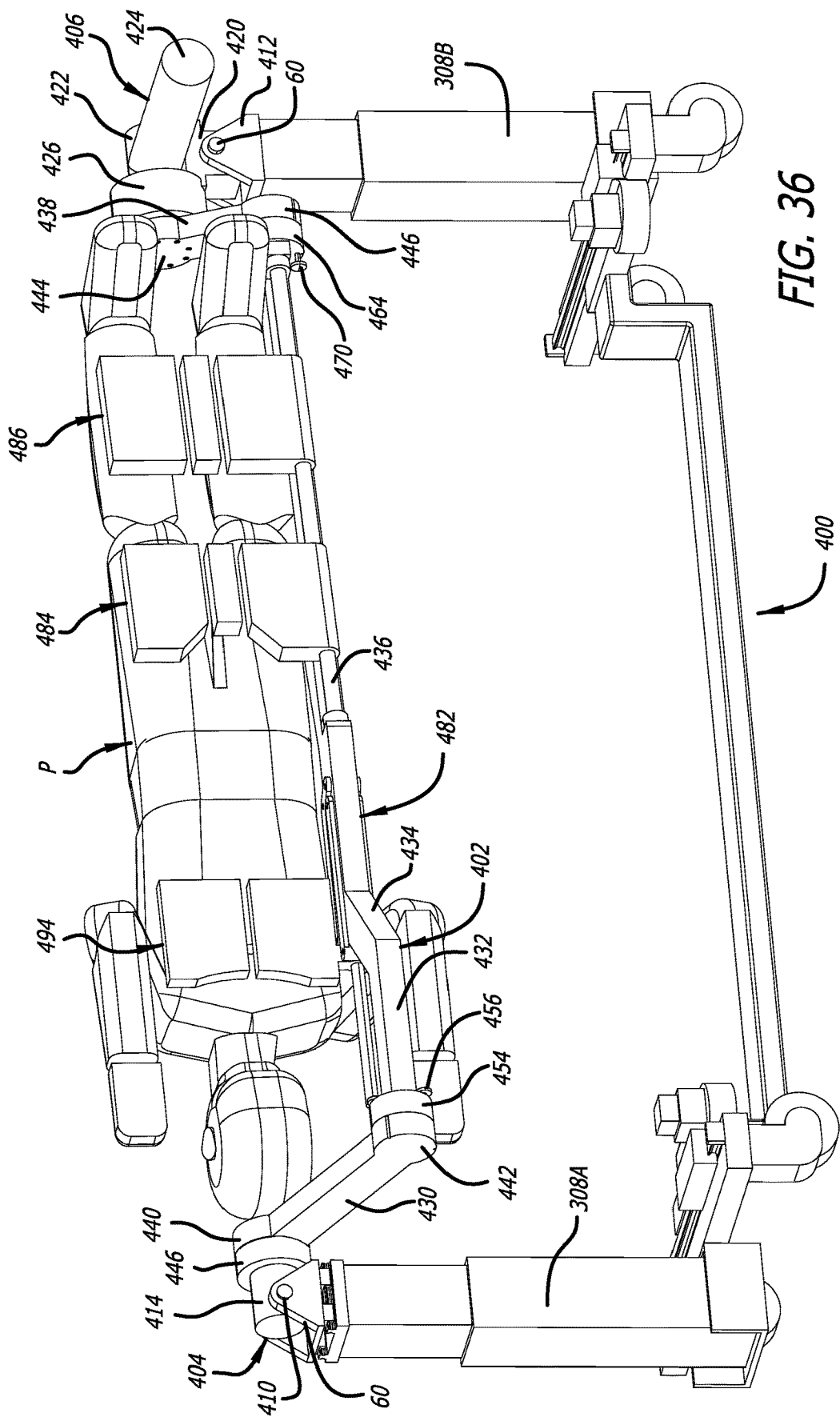
FIG. 36 is a top second side perspective view that illustrates the surgical table of FIG. 31 in the left configuration with a patient being supported thereon in a lateral position.
Figure 37:
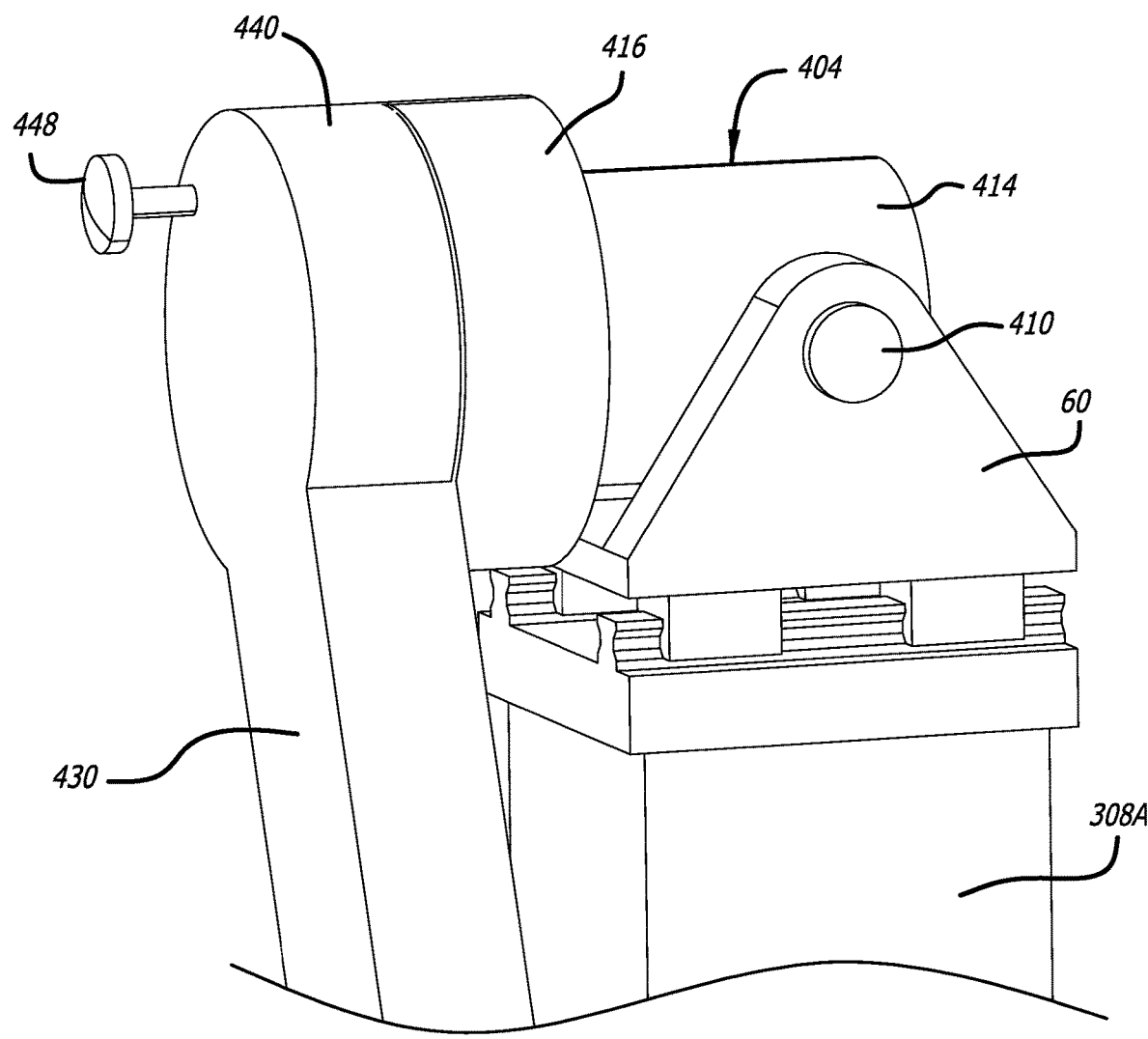
FIG. 37 is an enlarged top first side perspective view that illustrates an upper portion of the surgical table of FIG. 31 in the left configuration at and adjacent the first end thereof.
Figure 38:
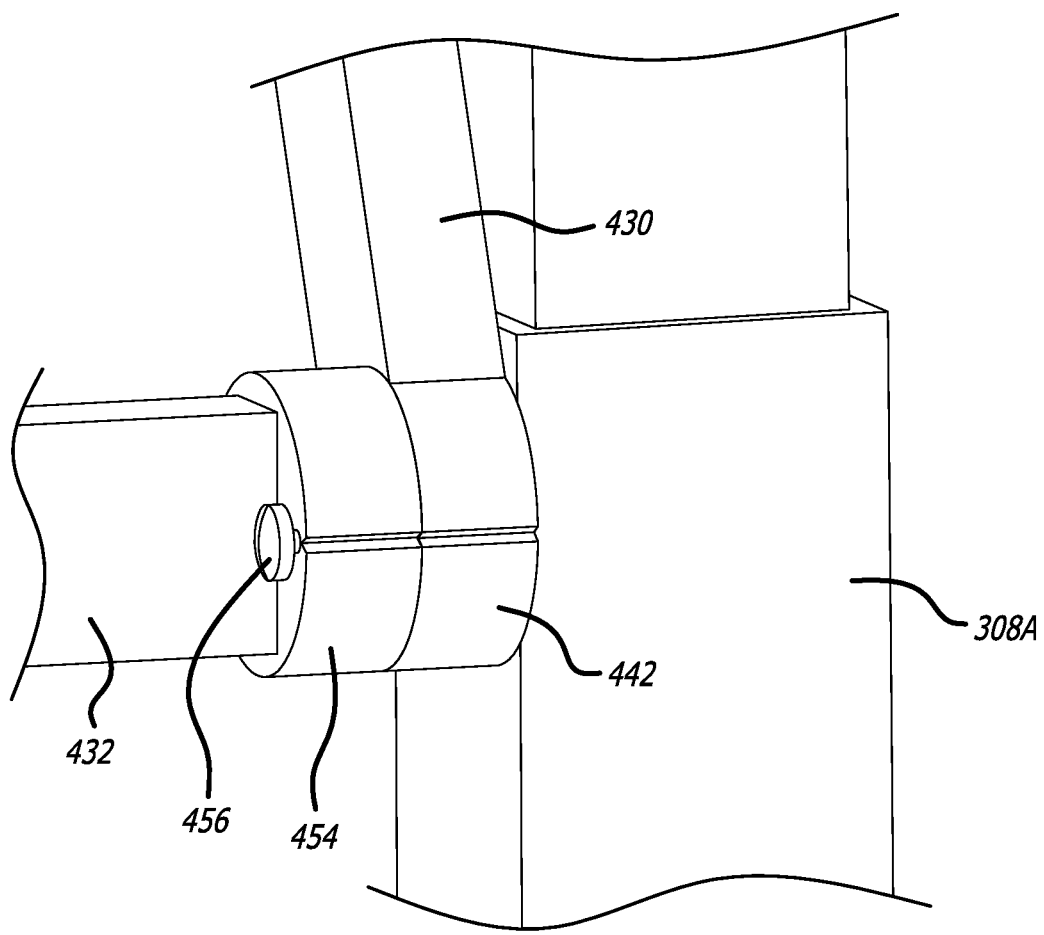
FIG. 38 is an enlarged top first side perspective view that illustrates a middle portion of the surgical table of FIG. 31 in the left configuration at and adjacent the first end thereof.
Figure 39:
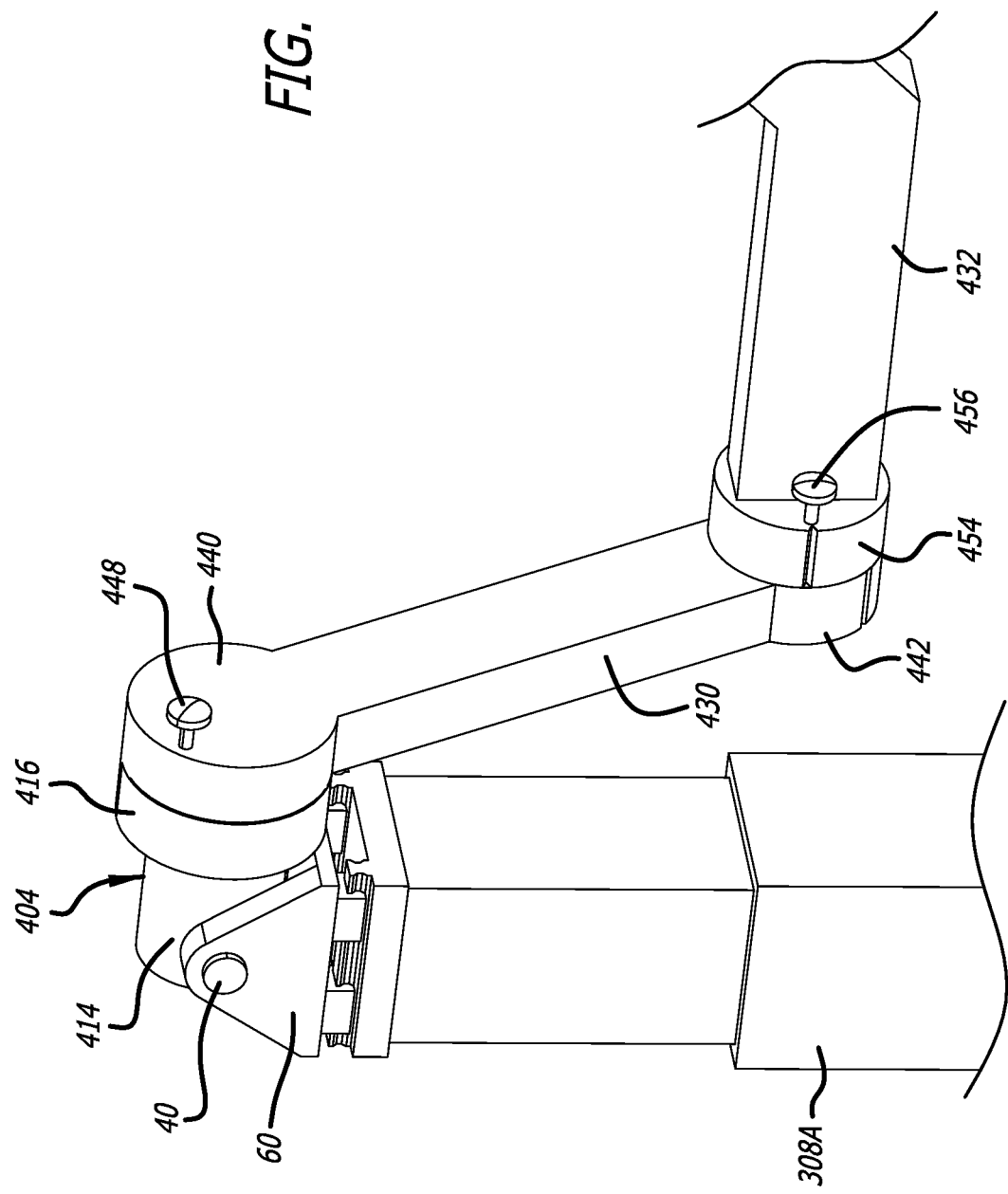
FIG. 39 is an enlarged top second side perspective view that illustrates an upper portion and a middle portion of the surgical table of FIG. 31 in the left configuration at and adjacent the first end thereof.
Figure 40:
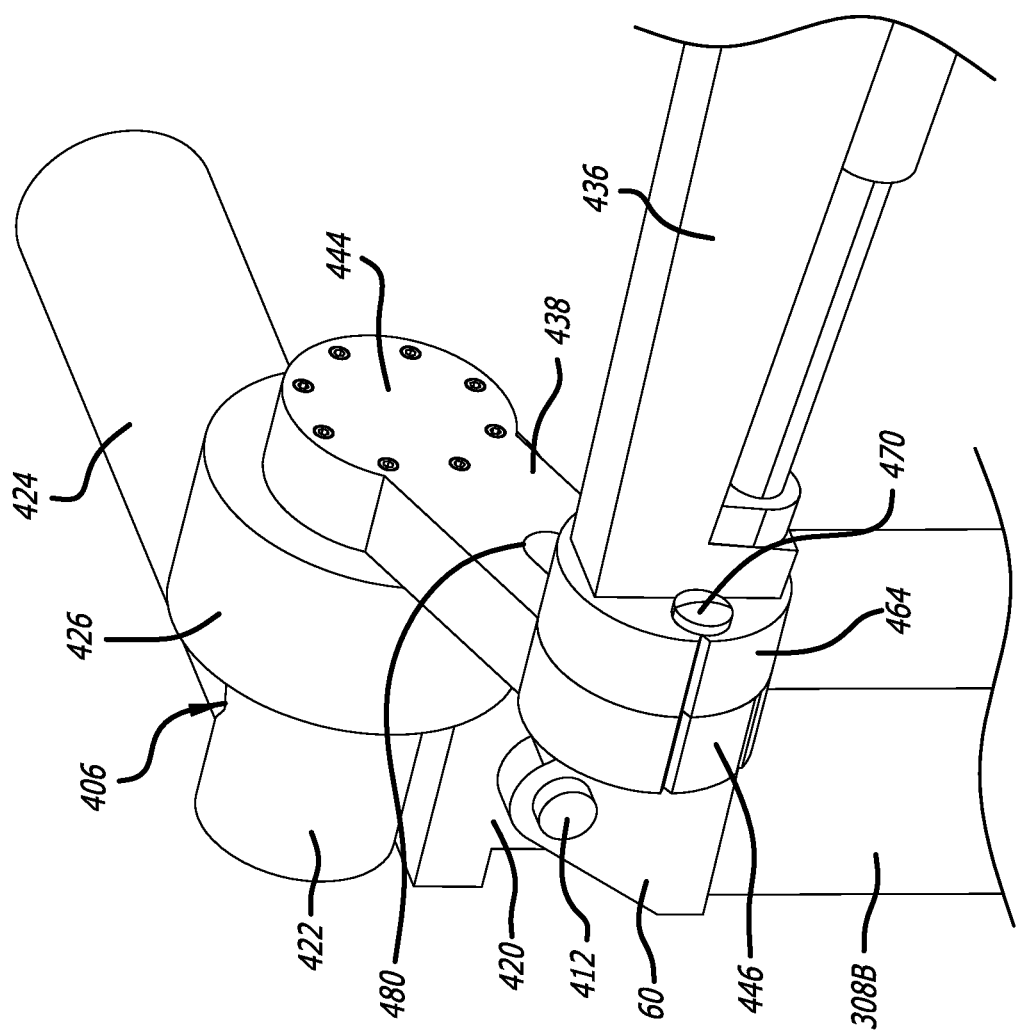
FIG. 40 is an enlarged top first side perspective view that illustrates an upper portion of the surgical table of FIG. 31 in the left configuration at and adjacent a second end thereof.
Figure 41:
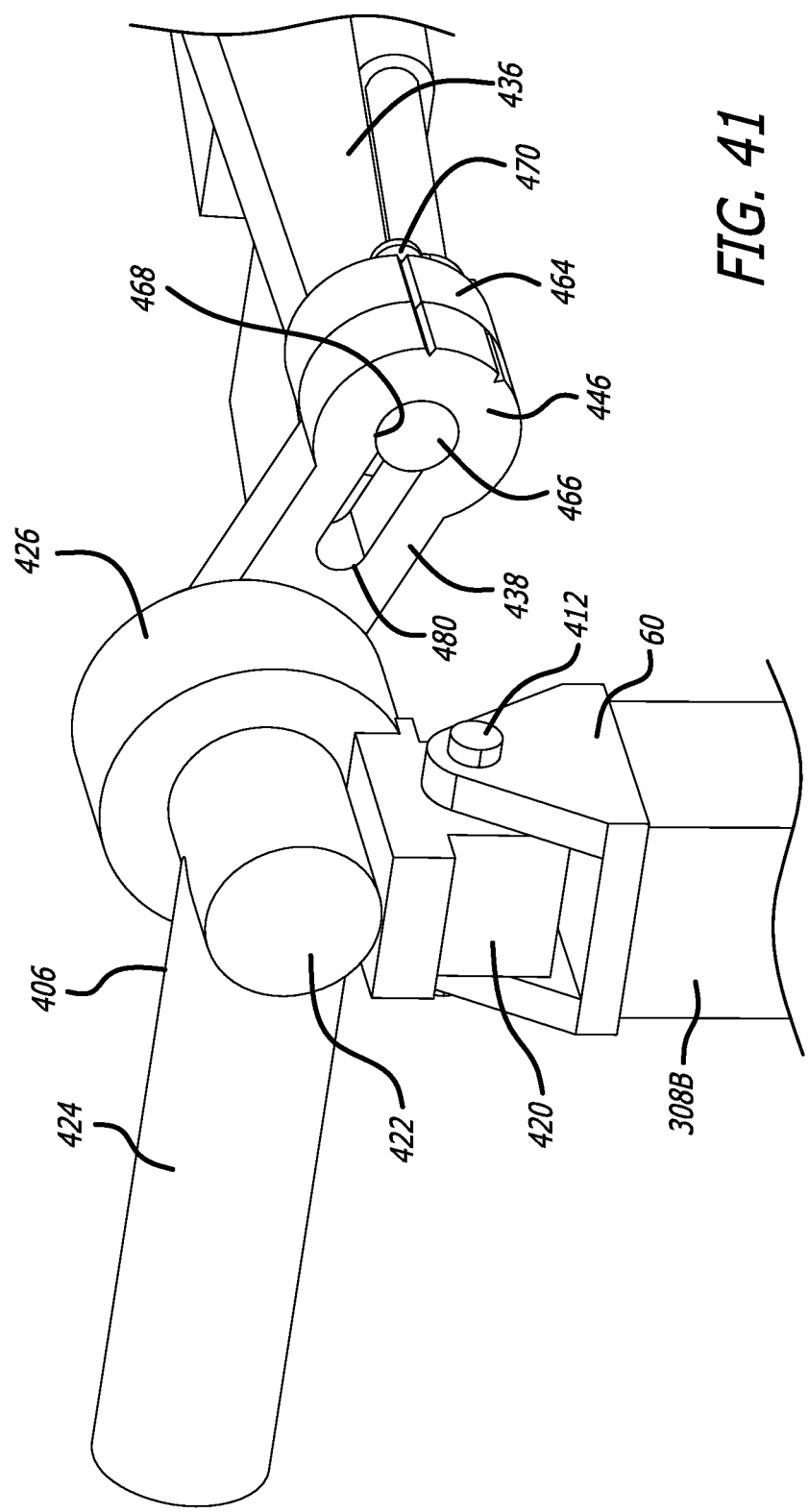
FIG. 41 is an enlarged top first side perspective view that illustrates an upper portion of the surgical table of FIG. 31 in the left configuration at and adjacent the second end thereof.
Figure 42:
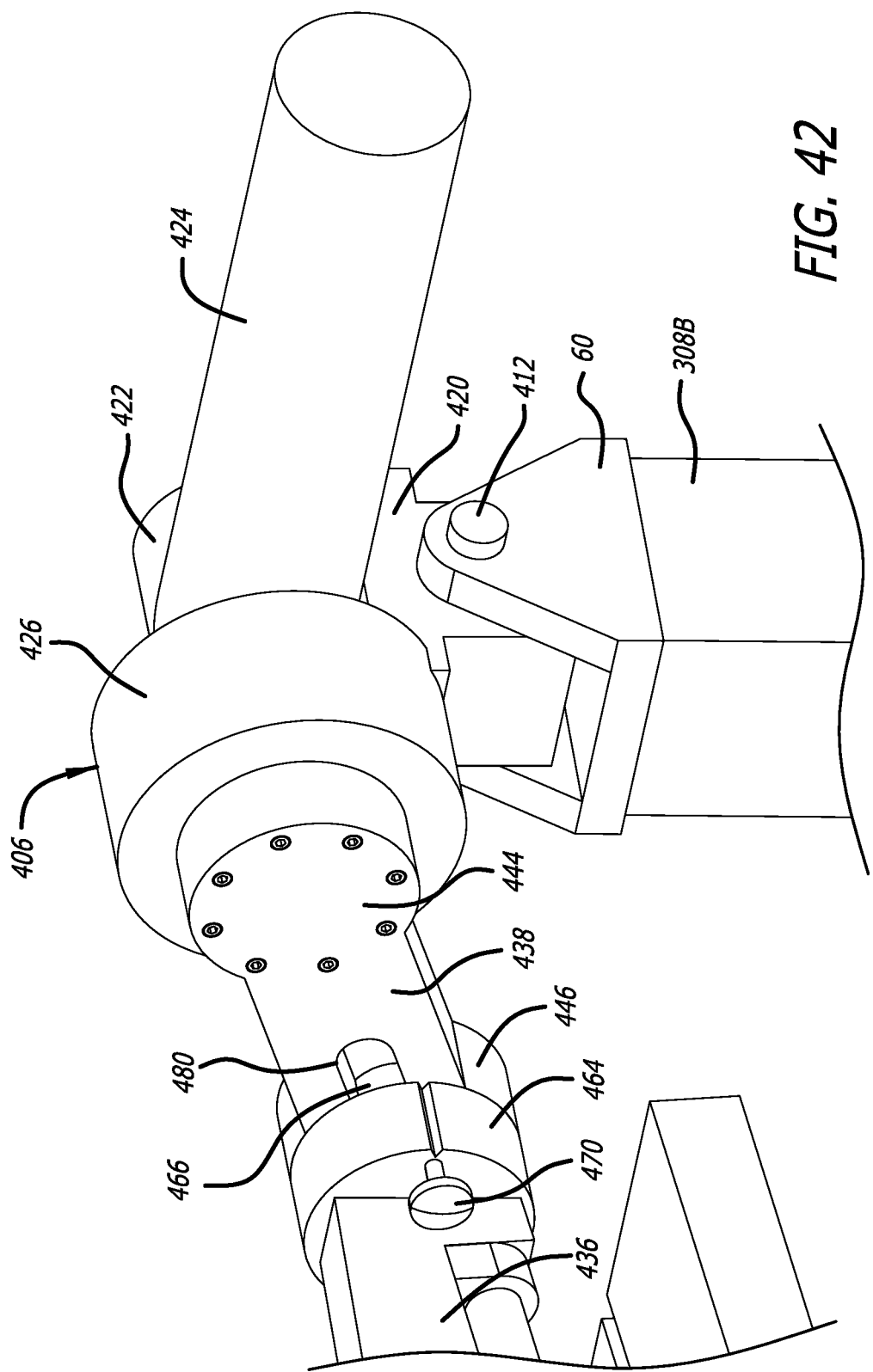
FIG. 42 is an enlarged top second side perspective view that illustrates an upper portion of the surgical table of FIG. 31 in the left configuration at and adjacent the second end thereof.

As depicted in at least FIGS. 31-33, the main beam 402 includes a first portion 430, a second portion 432, a third portion 434, a fourth portion 436, and a fifth portion 438. The first portion 430 is attached to the head portion 416, the fifth portion 438 is attached to the head portion 426, and the second portion 432, the third portion 434, and the fourth portion 436 can be formed as a elongated beam portion that extends between the first portion 430 and the fifth portion 438. As depicted in at least FIGS. 31 and 32, the first portion 430 and the fifth portion 438 extend transversely to the axis of rotation $A_1$ and space the second portion 432, the third portion 434, and the fourth portion 436 apart from the axis of rotation $A_1$ of the main beam 402. As discussed above with respect to the surgical frame 10 and as depicted in FIGS. 35 and 36, this offset affords positioning of the cranial-caudal axis of patient P approximately aligned with the axis of rotation $A_1$ of the offset main beam 402. Furthermore, the second portion 432 and the fourth portion 436 at the very least extend substantially parallel to the axis of rotation $A_1$, and the third portion 434 transitions between the second portion 432 and the fourth portion 436. As discussed below, the fourth portion 436 includes support apparatus to facilitate supporting the patient P on the main beam 402.

The second portion 432, the third portion 434, and the fourth portion 436 can be unitarily formed with another. Furthermore, the second portion 432 and the fourth portion 436 are attached to the first portion 430 and the fifth portion 438, respectively, to afford the reconfiguration of the main beam 402 between the left configuration and the right configuration. The left configuration of the main beam 402 is depicted in FIGS. 31-42, and the right configuration of the main beam 402 is depicted in FIGS. 52-56.

The first portion 430 includes a first end portion 440 and an opposite second end portion 442, and the fifth portion 438 includes a first end portion 444 and a second end portion 446. The first end portion 440 is attached to the head portion 416, and the second end portion 442 is attached to the second portion 432. Furthermore, the first end portion 444 is attached to the head portion 426, and the second end portion 446 is attached to the fourth portion 436. Rotation of the main beam 402 is possible because the head portion 416, and hence, the first portion 430 of the main beam 402 attached thereto are rotatable relative to the body portion 414, and because the head portion 426, and hence, the fifth portion 438 of the main beam 402 attached thereto are rotatable relative to the body portion 422. To facilitate conversion between the left configuration and the right configuration, the attachment of the first end portion 440 to the head portion 416, the attachment of the second end portion 442 to the second portion 432, the attachment of the second end portion 446 to the fourth portion 436 are adjustable.

The first portion 430 is rotatably adjustable about an axis of rotation between a first fixed position and a second fixed position relative to the head portion 416 to facilitate the left configuration and the right configuration, respectively, of the main beam 402. For example, one of the head portion 416 and the first end portion 440 of the first portion 430 can include an axle (not shown) that can be received in an aperture (not shown) formed in the other of the head portion 416 and the first end portion 440. As such, the first portion 430 can be rotatable relative to the head portion 416 between the first fixed position and the second fixed position, and a pin 448 can be received through portions of the head portion 416 and the first end portion 440 to facilitate fixation in the first fixed portion and the second fixed position. Furthermore, indicia can be provided on the head portion 416 and the first end portion 440 indicating the first fixed position corresponding to the left configuration, and indicia can be provided on the head portion 416 and the first end portion 440 indicating the second fixed positon corresponding to the right configuration.

The second portion 432 is rotatably adjustable between a first fixed position and a second fixed position relative to the first portion 430 to facilitate the left configuration and the right configuration, respectively, of the main beam 402. For example, one of the second end portion 442 of the first portion 430 and a first end portion 454 of the second portion 432 can include an axle (not shown) that can be received in an aperture (not shown) formed in the other of the second end portion 442 of the first portion 430 and the first end portion 454 of the second portion 432. As such, the second portion 432 (as well as at least the third portion 434 and the fourth portion 436 attached thereto) can be rotatable relative to the first portion 430 between the first fixed position and the second fixed position, and pins 456 can be received through portions of the second end portion 442 and the first end portion 454 to facilitate fixation in the first fixed position and the second fixed position. Furthermore, indicia can be provided on the second end portion 442 and the first end portion 454 indicating the first fixed position corresponding to the left configuration, and indicia can be provided on the second end portion 442 and the first end portion 454 indicating the second fixed position corresponding to the right configuration.

The fourth portion 436 is adjustable between a first fixed position and a second fixed position relative to the fifth portion 438 to facilitate the left configuration and the right configuration, respectively, of the main beam 402. For example, one of the second end portion 446 of the fifth portion 438 and a first end portion 464 of the fourth portion 436 can include an axle (not shown) that can be received in an aperture (not shown) formed in the other of the second end portion 446 of the fifth portion 438 and the first end portion 464 of the fourth portion 436. As depicted in at least FIG. 41, the first end portion 464 of the fourth portion 436 includes an axle 466, and the second end portion 446 of the fifth portion 438 includes an aperture 468 for receiving the axle 466. As such, the fourth portion 436 (as well as at least the second portion 432 and the third portion 434 attached thereto) can be rotatable relative to the fifth portion 438 between the first fixed position and the second fixed position, and pins 470 can be received through portions of the second end portion 446 and the first end portion 464 to facilitate fixation in the first fixed position and the second fixed position. Furthermore, indicia can be provided on the second end portion 446 and the first end portion 464 indicating the first fixed position corresponding to the left configuration, and indicia can be provided on the second end portion 446 and the first end portion 464 indicating the second fixed position corresponding to the right configuration.

Figure 47:
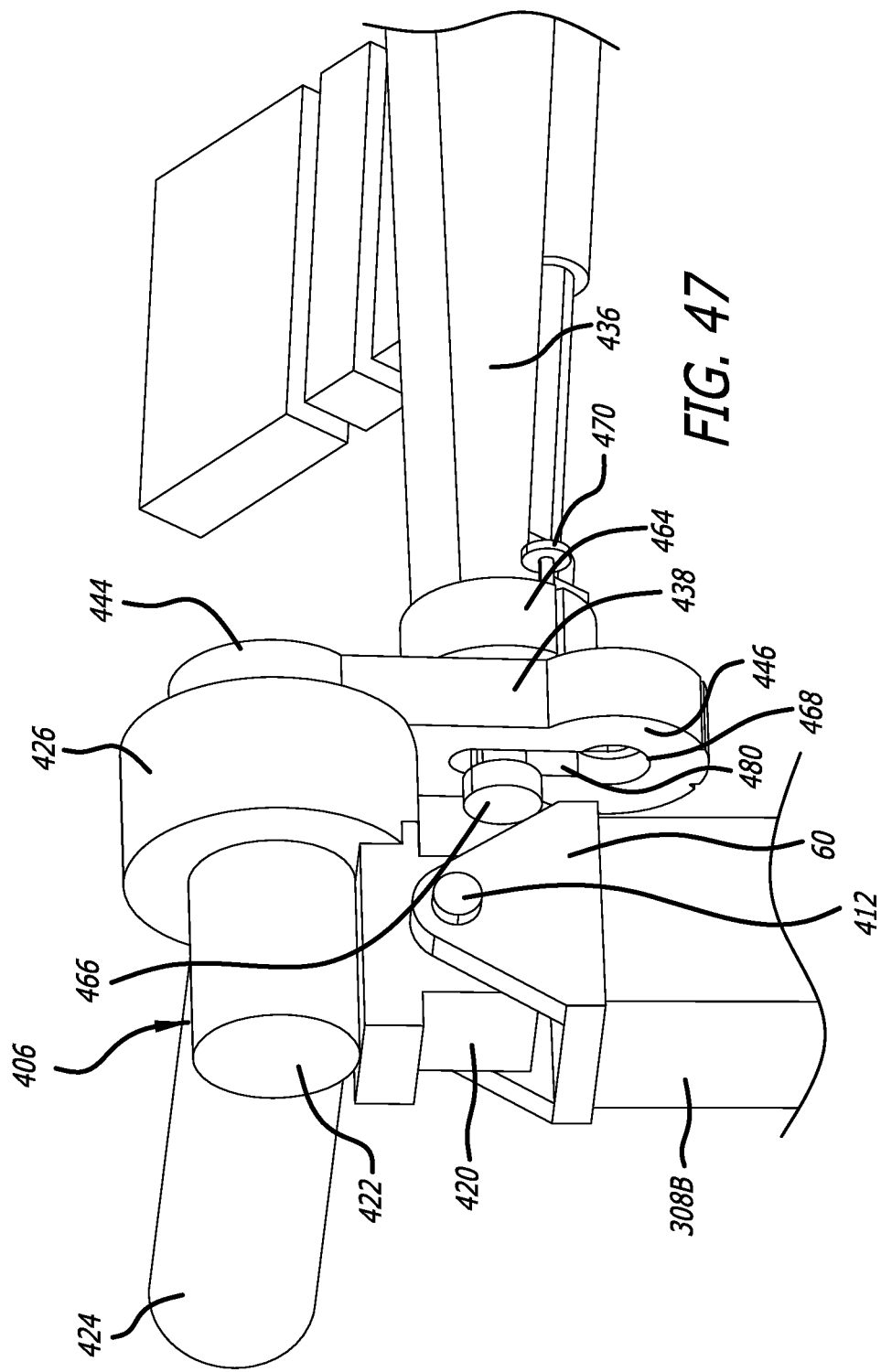
FIG. 47 is an enlarged top first side perspective view that illustrates an upper portion of the surgical table of FIG. 31 at and adjacent the second end depicting portions of the main beam thereof during the second portion of the reconfiguration process.
Figure 48:
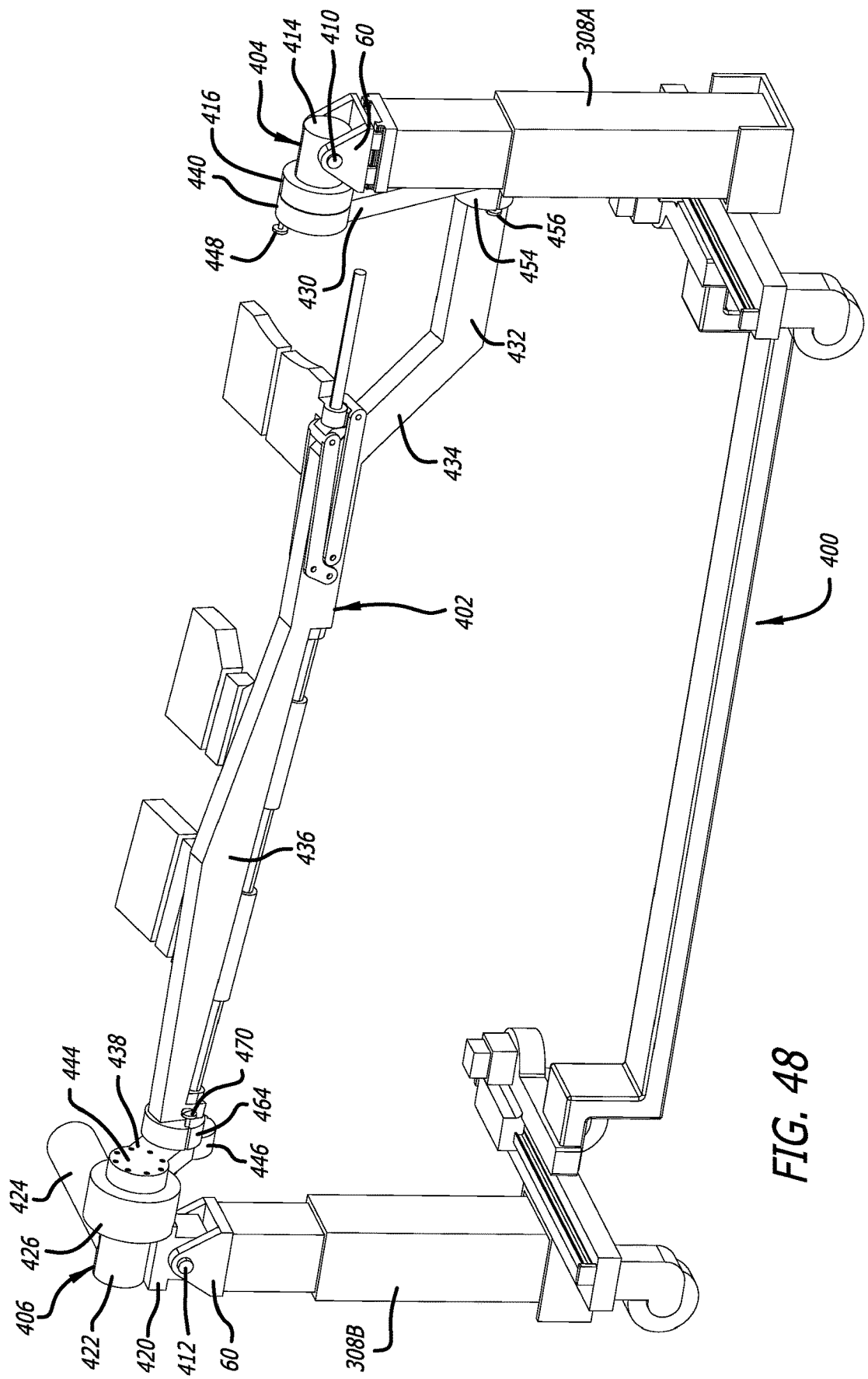
FIG. 48 is a top first side perspective view of the surgical table of FIG. 31 similar to FIGS. 43 and 46 that illustrates portions of the main beam thereof during the second portion of the reconfiguration process.
Figure 49:
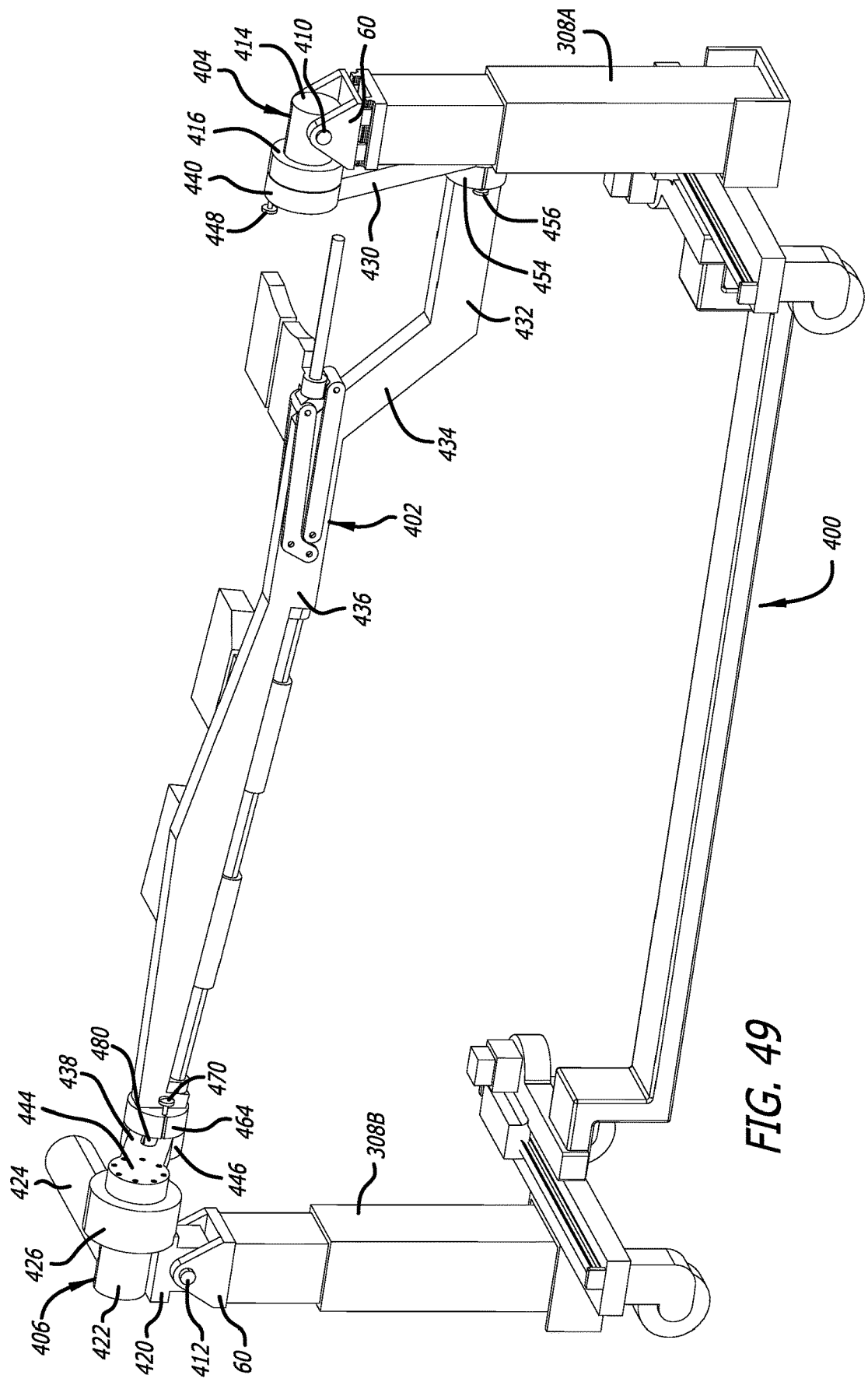
FIG. 49 is a top first side perspective view of the surgical table of FIG. 31 similar to FIGS. 43, 46, and 48 that illustrates portions of the main beam thereof during a third portion of the reconfiguration process.
Figure 50:
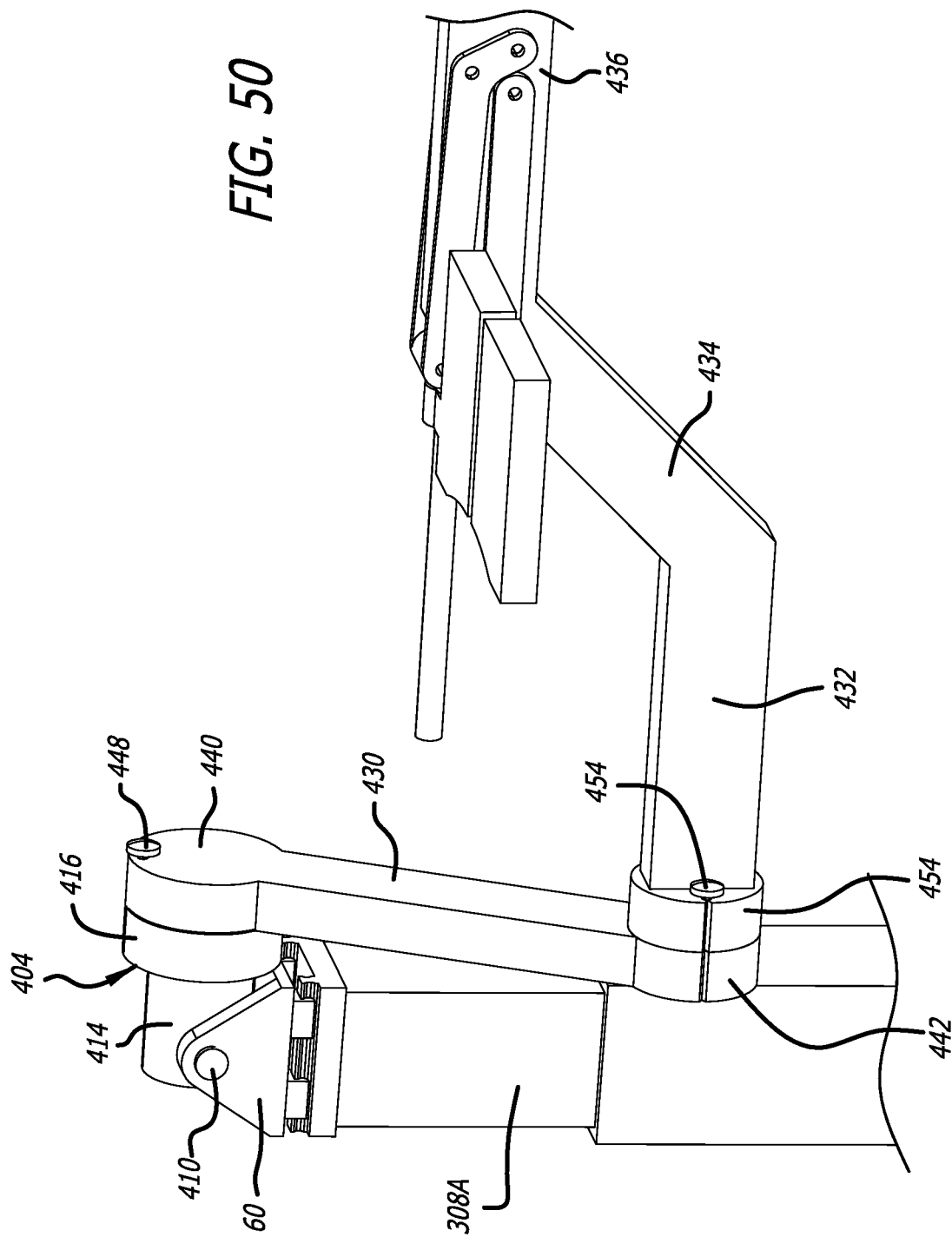
FIG. 50 is an enlarged top second side perspective view that illustrates an upper portion and a middle portion of the surgical table of FIG. 31 at and adjacent the first end depicting portions of the main beam thereof during the third portion of the reconfiguration process.
Figure 51:
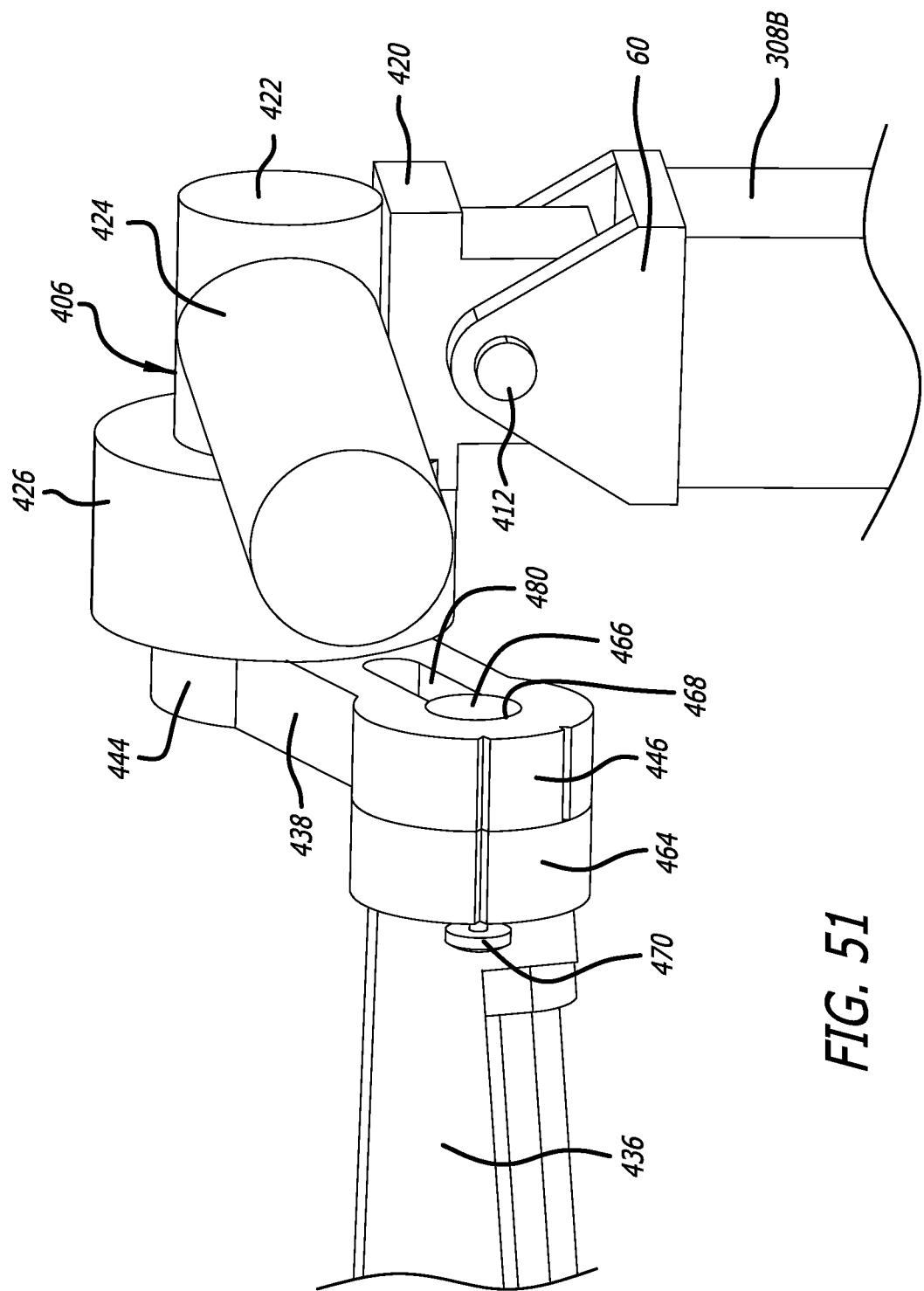
FIG. 51 is an enlarged top second side perspective view that illustrates an upper portion of the surgical table of FIG. 31 at and adjacent the first end depicting portions of the main beam thereof during the third portion of the reconfiguration process.
Figure 52:
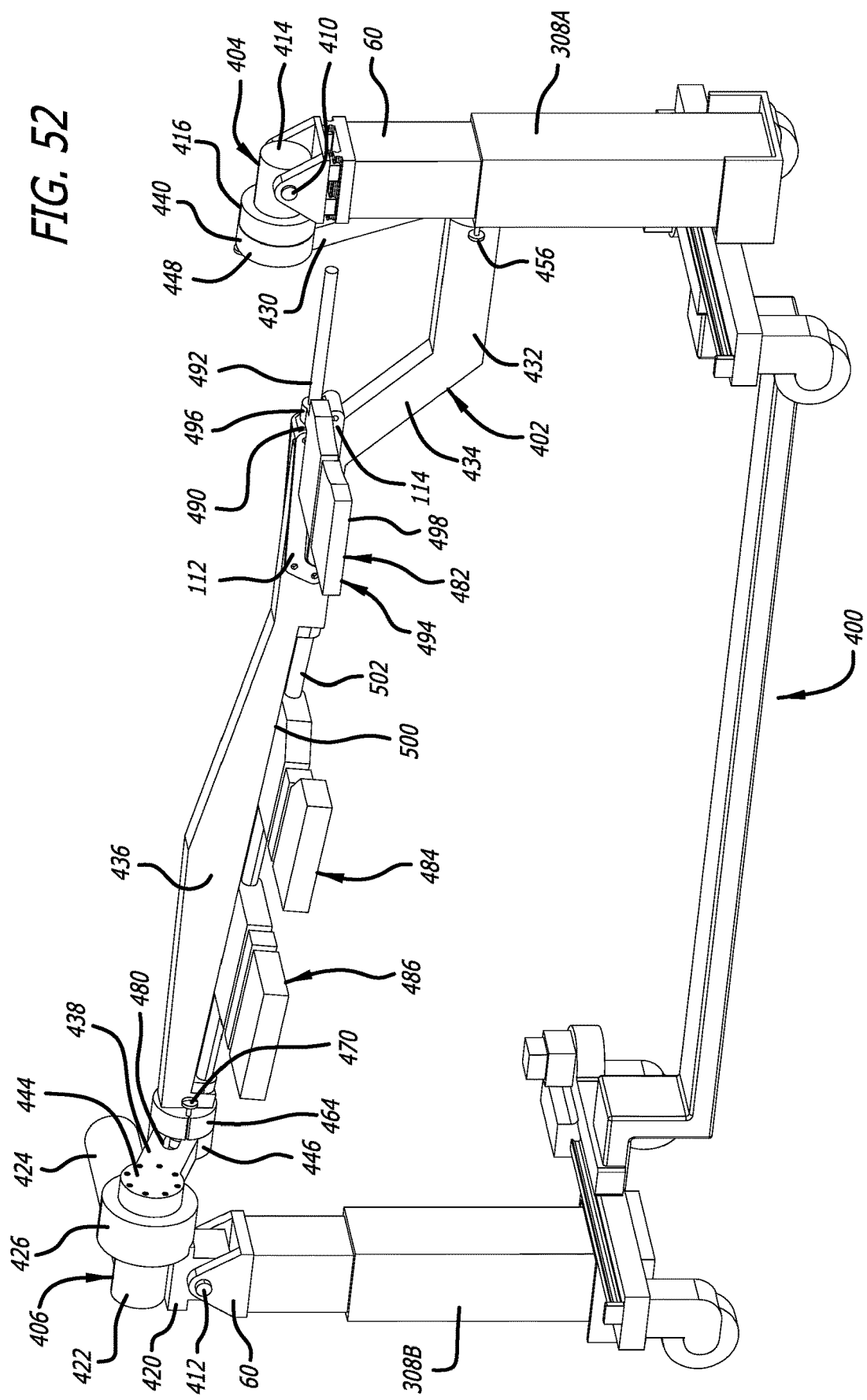
FIG. 52 is a top first side perspective view of the surgical table of FIG. 31 similar to FIGS. 43, 46, 48, and 49 that illustrates portions of the main beam thereof in the right configuration after completion of the reconfiguration process.
Figure 53:
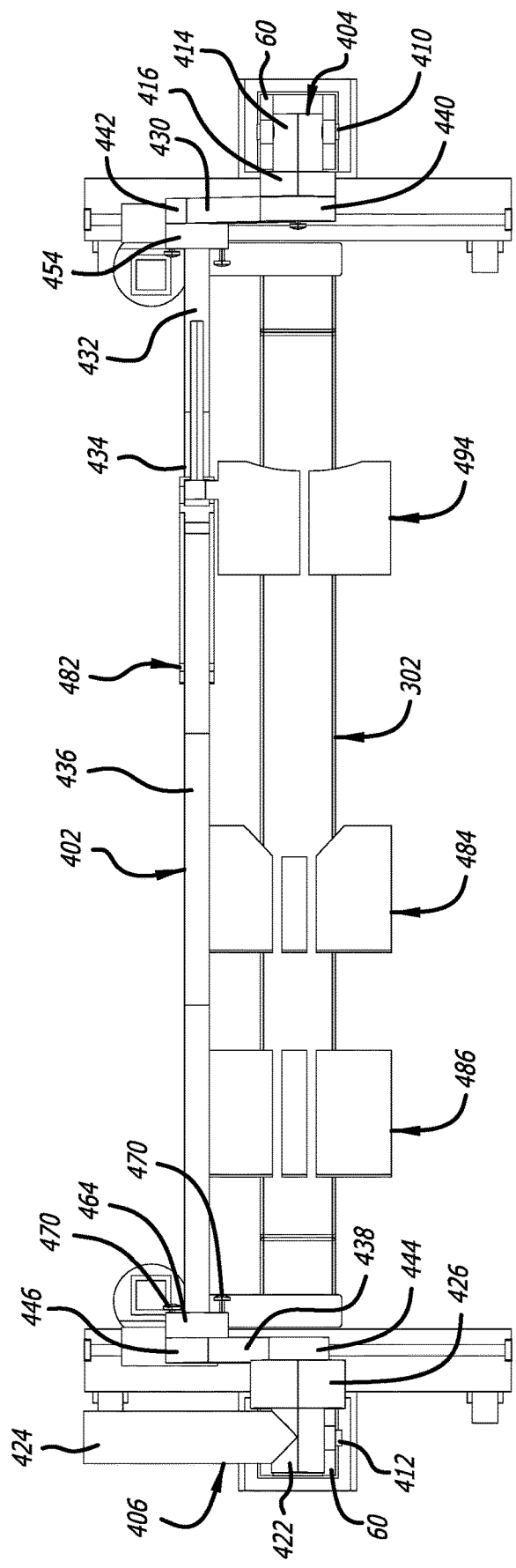
FIG. 53 is a top plan view that illustrates the surgical table of FIG. 31 in the right configuration.
Figure 54:
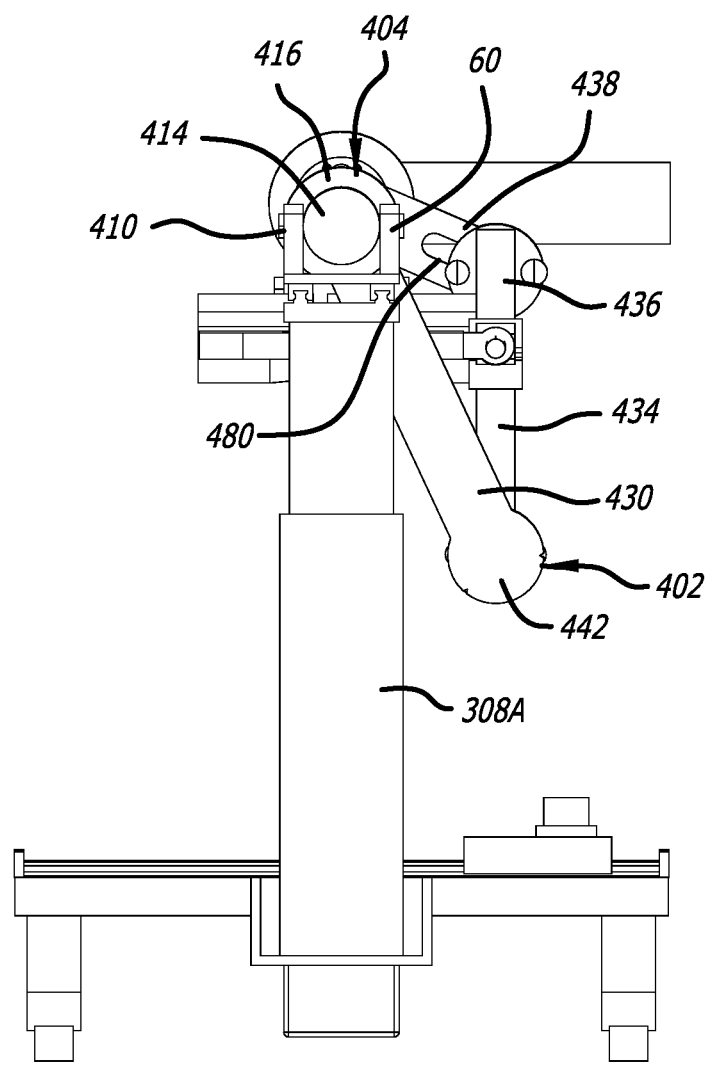
FIG. 54 is a first end elevational view that illustrates the surgical table of FIG. 31 in the right configuration.
Figure 55:
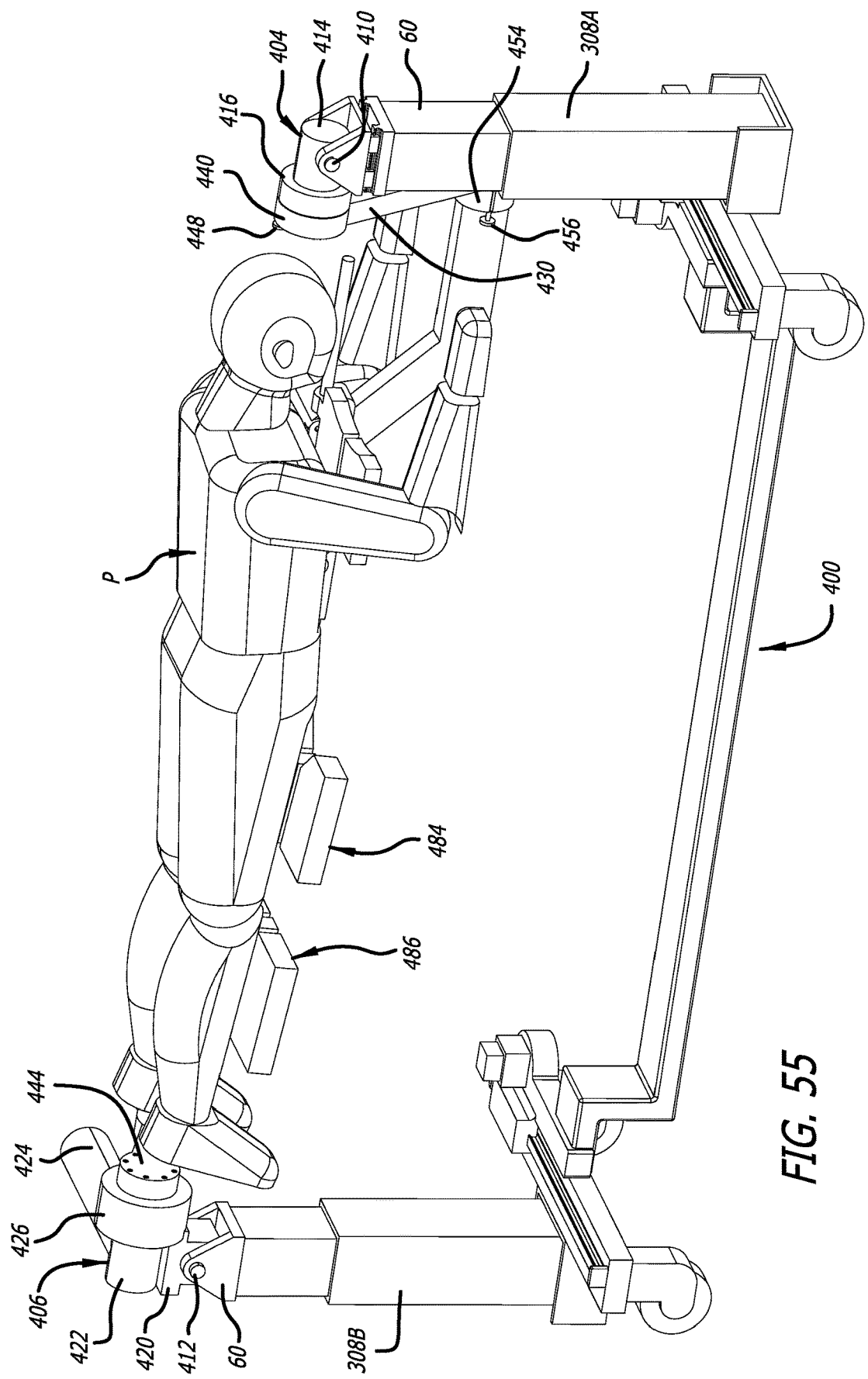
FIG. 55 is a top first side perspective view that illustrates the surgical table of FIG. 31 in the right configuration with the patient being supported on the main beam thereof in a prone position.
Figure 56:
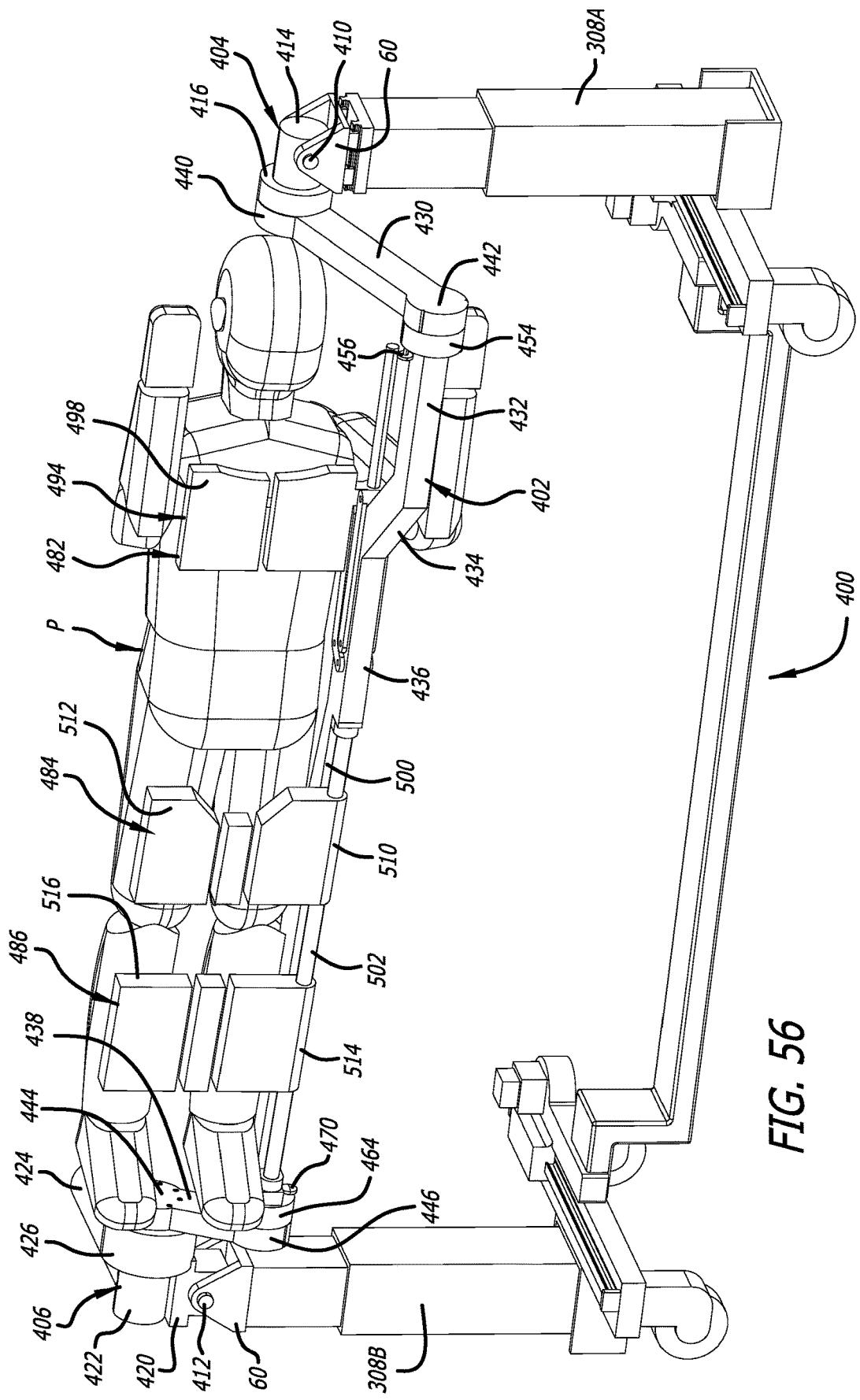
FIG. 56 is a top first side perspective view that illustrates the surgical table of FIG. 31 in the right configuration with the patient being supported on the main beam thereof in a lateral position.

As depicted in in FIGS. 31 and 32, the rotational adjustment of the second portion 432 relative to the first portion 430 occurs along an axis of rotation $A_2$, and rotational adjustment of the fourth portion 436 relative to the fifth portion 438 occurs along an axis of rotation $A_3$. The axes of rotation $A_2$ and $A_3$ are parallel, but not aligned, with one another. As such, the above-discussed adjustment between the first fixed positions and the second fixed positions potentially could lead to unwanted binding of the portions of the main beam 402 during reconfiguration from the left configuration to the right configuration, and vice versa. Such binding would interfere with the adjustment between the left configuration and the right configuration. To afford the adjustment between the left configuration and the right configuration, the fifth portion 438 includes an elongated slot 480 formed therein that communicates with the aperture 468, and the axle 466 is moveable between a first inward position and a second outward position with respect to the first end portion 464 of the fourth portion 436. When the axle 466 is in the first inward portion, the axle 466 is received in the aperture 468, and the when the axle 466 is in the second outward position, the axle 466 can be moved from the aperture 468 into and along the elongated slot 480. As depicted in FIG. 47, movement of the axle 466 along the elongated slot 480 affords reconfiguration from the left configuration to the right configuration, and vice versa, without the possibility of binding of the main beam 402 during such reconfiguration.

As depicted in at least FIG. 31, the main beam 402 includes various support structures provided thereon for supporting the patient P. Like the main beam 402, these support structures are moveable between a left configuration for supporting the patient P when the main beam 402 is in the left configuration, and a right configuration for supporting the patient P when the main beam 402 is in the right configuration.

A torso support 482, an upper leg support 484, and a lower leg support 486 are provided on the main beam 402, and are moveable between the left configuration and the right configuration. As depicted in FIGS. 31-36, the torso support 482, the upper leg support 484, and the lower leg support 486 are in the left configuration, and as depicted in in FIGS. 52-56, the torso support 482, the upper leg support 484, and the lower leg support 486 are in the right configuration.

The torso support 482 is supported on the main beam 402, and can be similar to and include various components of the torso-lift support 24. In particular, the torso support 482 includes the first links 112 and the second links 114. The first links 112 and the second links 114 are interconnected with one another by a plate 490, and a post 492 extends outwardly from the plate 490. In addition to a chest support 494, the post 492 also can support head supports (such as, for example, the head support 20), and arm supports (such as, for example, arm supports 22A and 22B). The chest support 494 includes a collar portion 496 and a support portion 498. The collar portion 496 is used to support the support portion 498 on the main beam 402, and the support portion 498 is used to support portions of the patient's chest thereon. To illustrate, the post 492 is received through the collar portion 496 to support the collar portion 496 thereon, and the support portion 498 extends outwardly from the collar portion 496. Using the interaction of the post 492 and the collar portion 496, the support portion 498 can be rotated between the left configuration and the right configuration thereof.

The upper leg support 484 and the lower leg support 486 also are supported on the main beam 402. The fourth portion 436 of the main beam 402 includes a recess 500 extending along a substantial portion thereof, and a post 502 supported by the fourth portion 436 extending from one end of the recess 500 to the other end of the recess 500. The upper leg support 484 includes a collar portion 510 and a support portion 512, and the lower leg support 486 includes a collar portion 514 and a support portion 516. The collar portions 510 and 514 are used to support the support portions 512 and 516 on the post 502, respectively, and the support portion 512 is used to support the patient's upper legs and the support portion 516 is used to support the patient's lower legs. To illustrate, the post 502 is received through the collar portions 510 and 514 to support the collar portions 510 and 514 thereon, and the support portions 512 and 516 extend outwardly from the collar portions 510 and 514. Using the interaction of the post 502 and the collar portions 510 and 514, the support portions 512 and 516 can be rotated between the left configuration and the right configuration.

Figure 43:
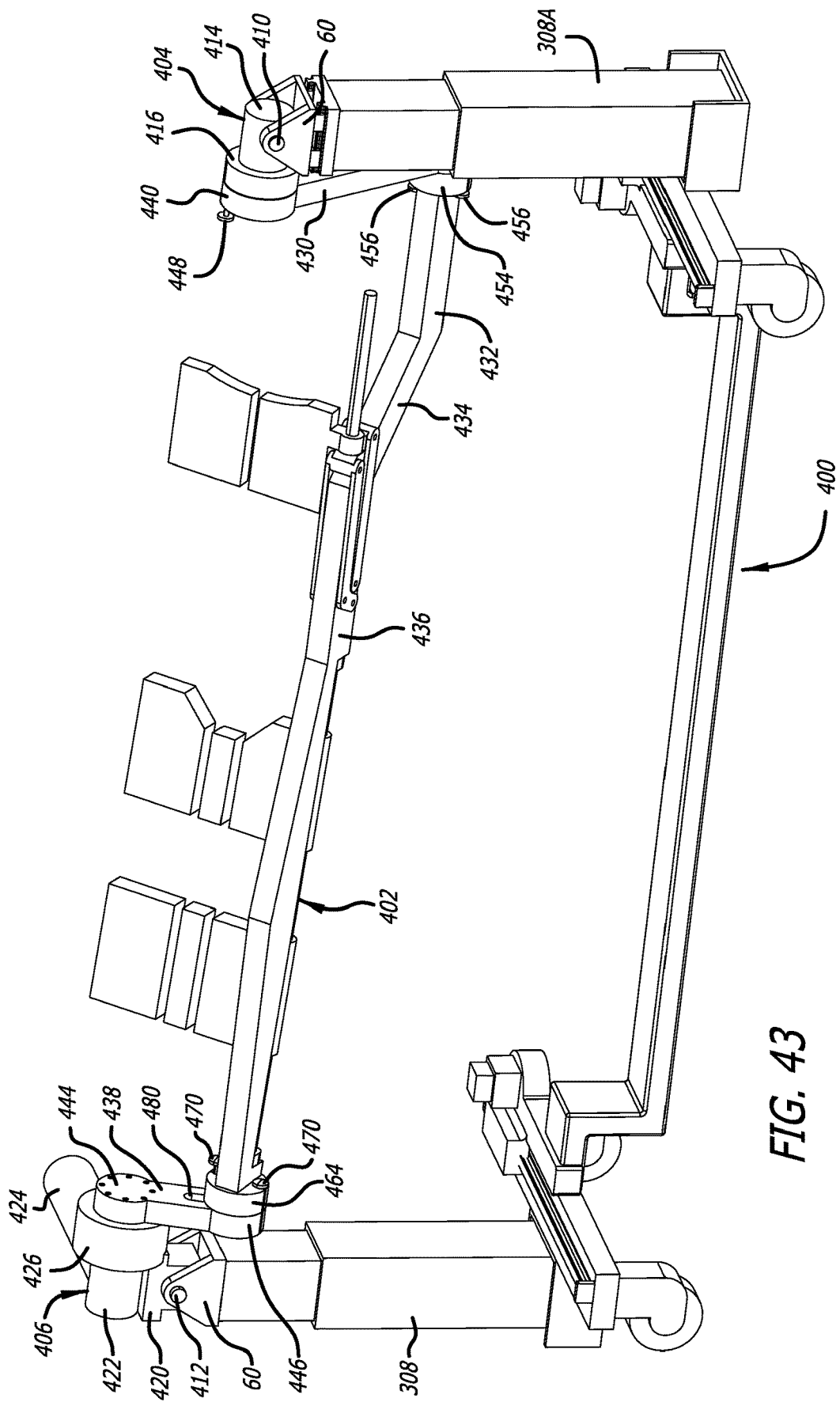
FIG. 43 is a top first side perspective view that illustrates the surgical table of FIG. 31 depicting portions of the main beam thereof during a first portion of the reconfiguration process from the left configuration to the right configuration.
Figure 44:
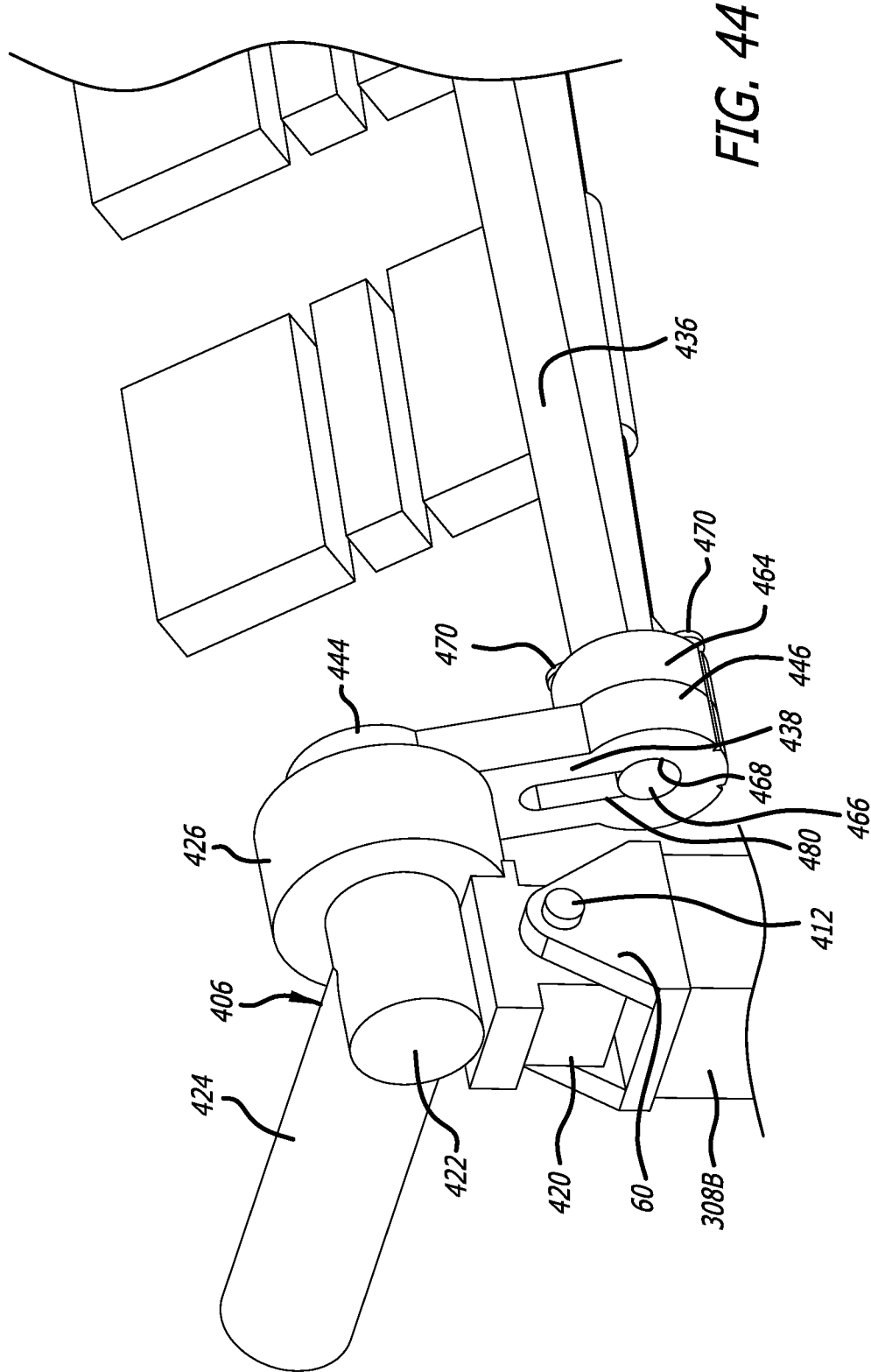
FIG. 44 is an enlarged top first side perspective view that illustrates an upper portion of the surgical table of FIG. 31 at and adjacent the second end depicting portions of the main beam thereof during a second portion of the reconfiguration process.
Figure 45:
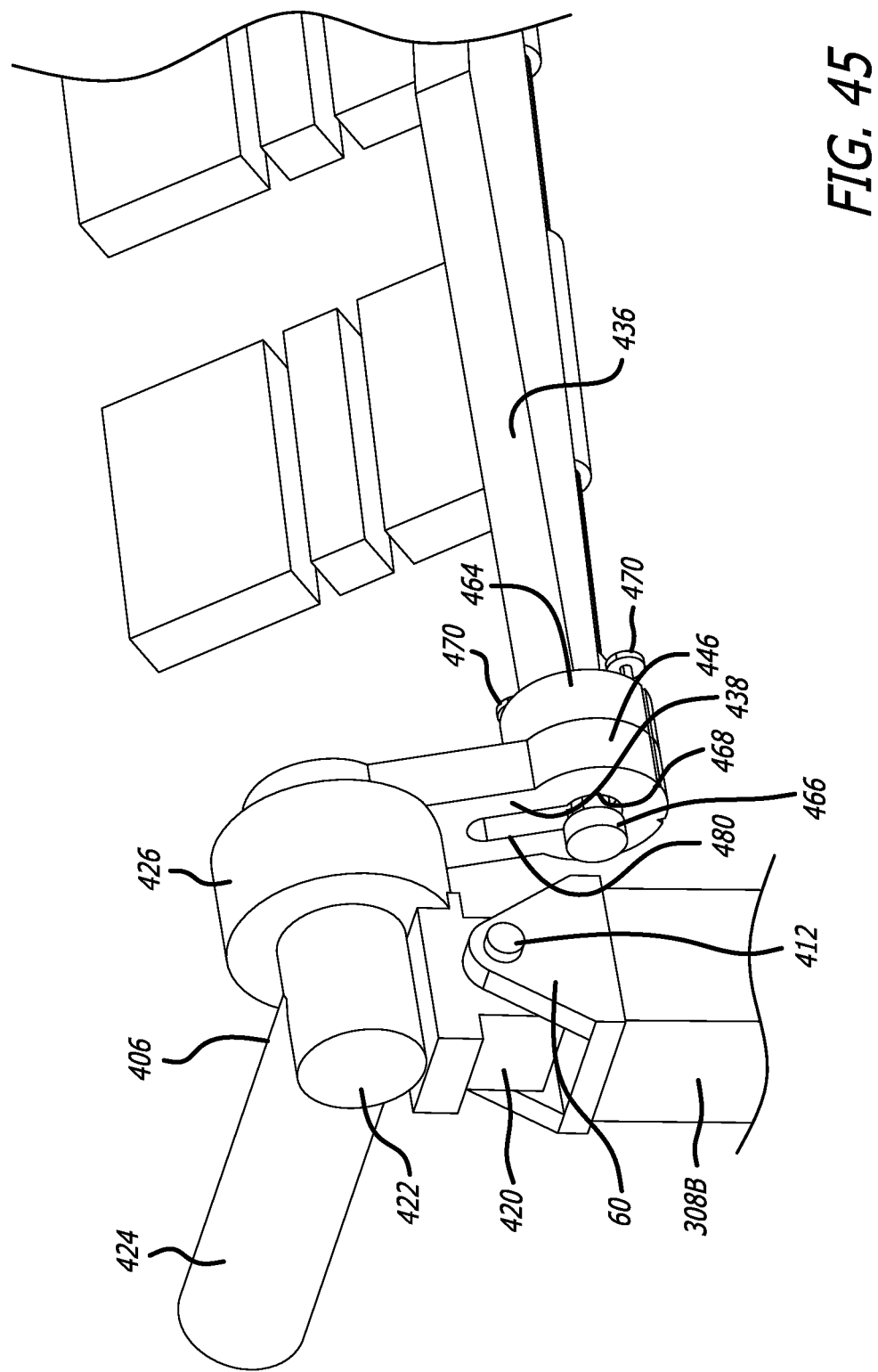
FIG. 45 is an enlarged top first side perspective view similar to FIG. 44 that illustrates an upper portion of the surgical table of FIG. 31 at and adjacent the second end depicting portions of the main beam thereof during the second portion of the reconfiguration process.
Figure 46:
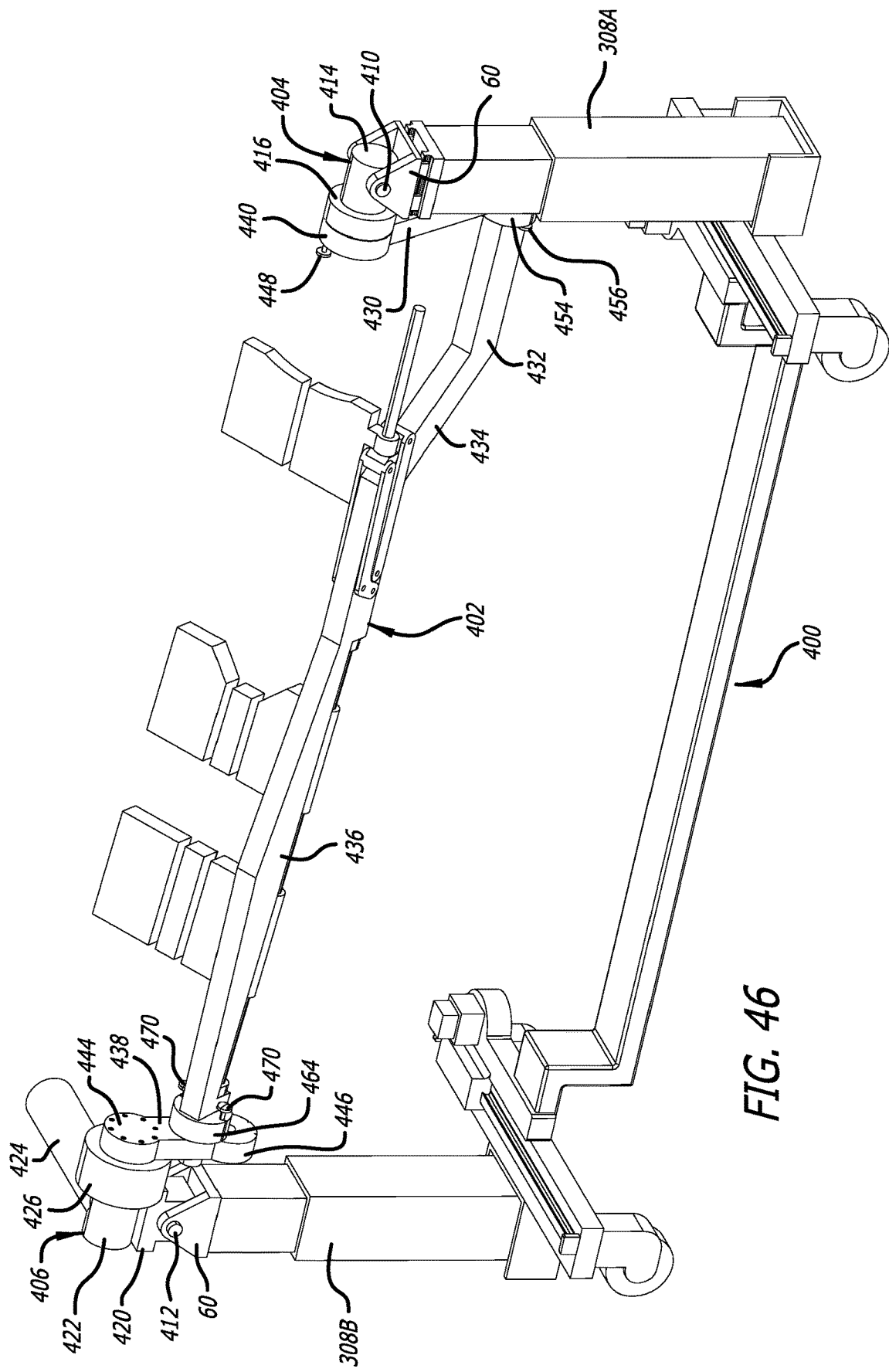
FIG. 46 is top first side perspective view of the surgical table of FIG. 31 similar to FIG. 43 that illustrates portions of the main beam thereof during the second portion of the reconfiguration process.

To facilitate reconfiguration of the main beam 402 from the left configuration to the right configuration, the pin 448, as depicted in FIG. 43, is disengaged from the head portion 416, the first portion 430 is rotated relative to the head portion 416 from a position corresponding to the first fixed position to a position corresponding to the second fixed position, and the pin 448 is reengaged to the head portion 416 to hold the first end portion 440 in the second fixed position.

Next, as depicted in FIGS. 44-48, one of the pins 456 and one of the pins 470 are disengaged from the second end portion 442 of the first portion 430 and the second end portion 446 of the fifth portion 438, the axle 466 is moved from the first inward position to the second outward position, and the second portion 432, the third portion 434, and the fourth portion 436 are rotated to move the second portion 432 and the fourth portion 436 from positions corresponding to the first fixed positions thereof to positions corresponding to the second fixed positions thereof. The rotation of the second portion 432, the third portion 434, and the fourth portion 436 avoids the above-discussed binding of the main beam by causing the axle 466 to slide within the elongated slot 480 and the fifth portion 438 (and the head portion 426 attached thereto) to rotate.

Thereafter, as depicted in FIGS. 49-52, the other of the pins 456 and the other of the pins 470 are engaged to the second end portion 442 of the first portion 430 and the second end portion 446 of the fifth portion 438, respectively, the axle 466 is moved from the second outward position to the first inward position, and the torso support 482, the upper leg support 484, and the lower leg support 486 are moved from the left configuration to the right configuration thereof.

Figure 57:
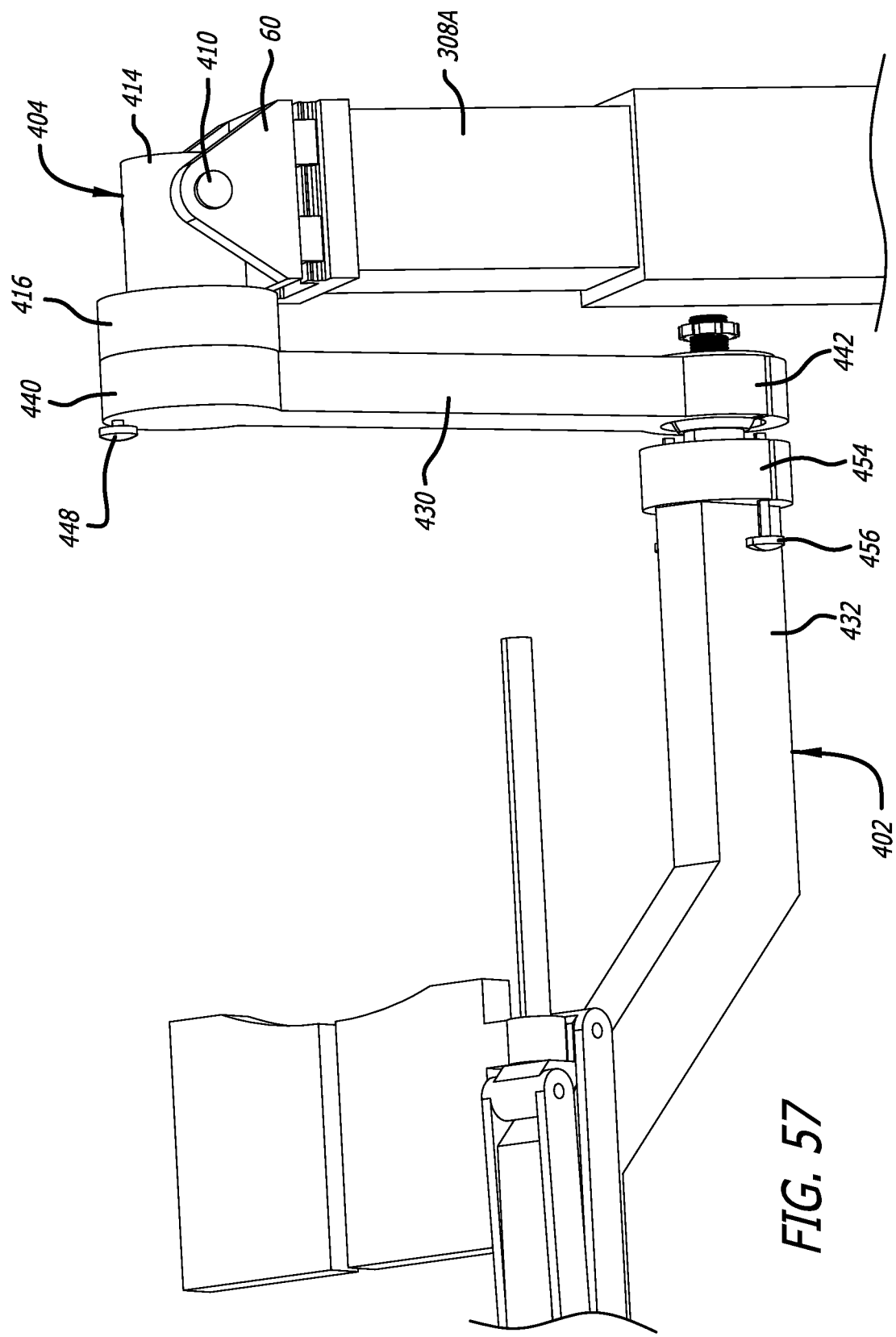
FIG. 57 is an enlarged top first side perspective view that illustrates an upper portion of a modified version of the first embodiment of the surgical table at and adjacent a first end thereof.
Figure 58:
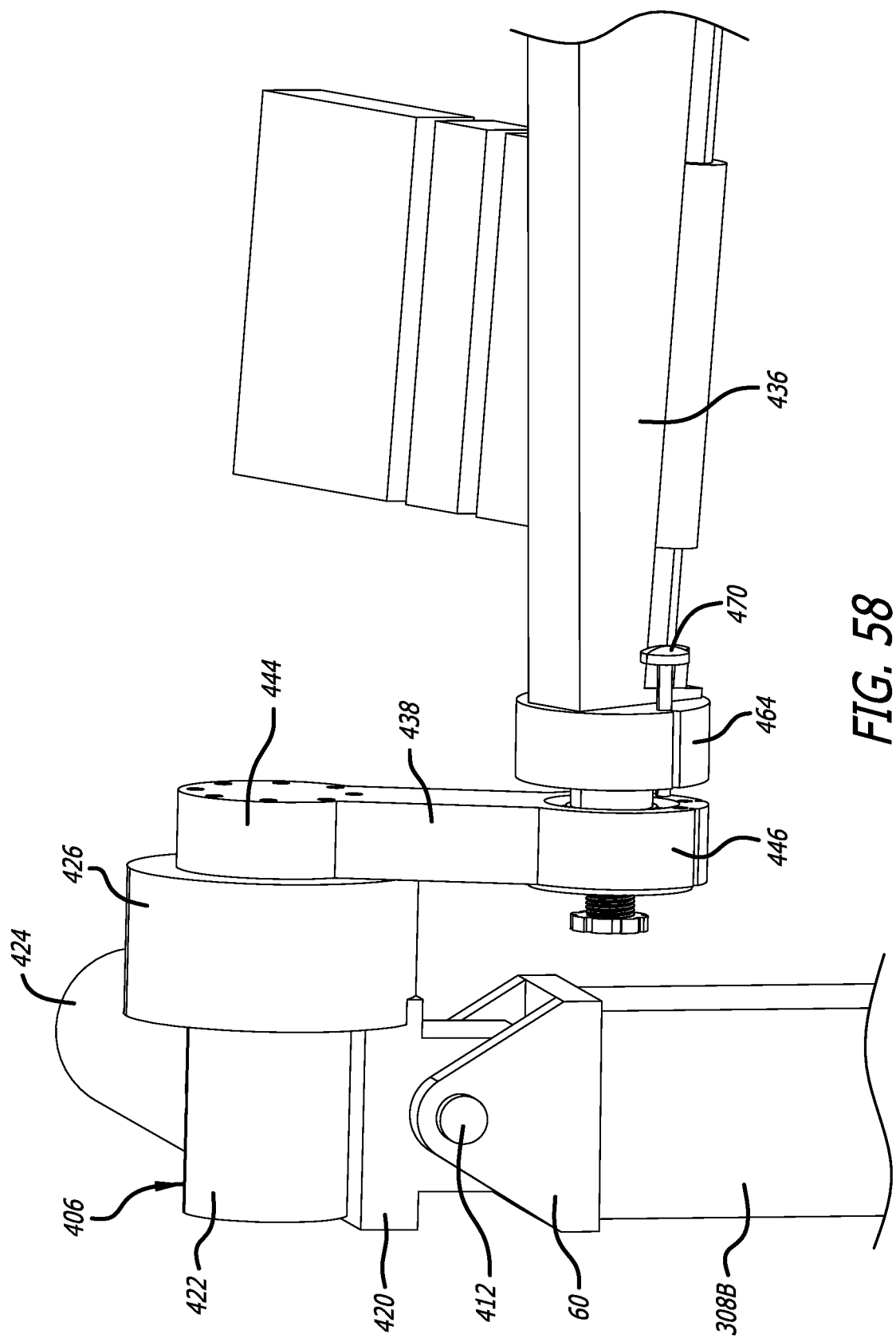
FIG. 58 is an enlarged top first side perspective view that illustrates an upper portion of the modified version of the first embodiment of the surgical table at and adjacent a second end thereof.

As depicted in FIGS. 57 and 58, rotation of the second portion 432, the third portion 434, and the fourth portion 436 without binding also can be facilitated via use of a first rotatable bearing 540 and a second rotatable bearing 542 to form articulable joints. The first rotatable bearing 540 can be received in a first aperture 544 formed in the second end portion 442 of the first portion 430, and the second rotatable bearing 542 can be received in a second aperture 546 formed in the second end portion 446 of the fifth portion 438. Furthermore, a first shaft 550 received in the first rotatable bearing 540 extends outwardly from the first end portion 454 of the second portion 432, and a second shaft 552 received in the second rotatable bearing 542 extends outwardly from the first end portion 464 of the fourth portion 436. The interaction of the first shaft 550 with the first rotatable bearing 540 and the interaction of the second shaft 552 with the second rotatable bearing 542 affords reconfiguration of the main beam 402 between the left configuration and the right configuration without binding.

Figure 59:
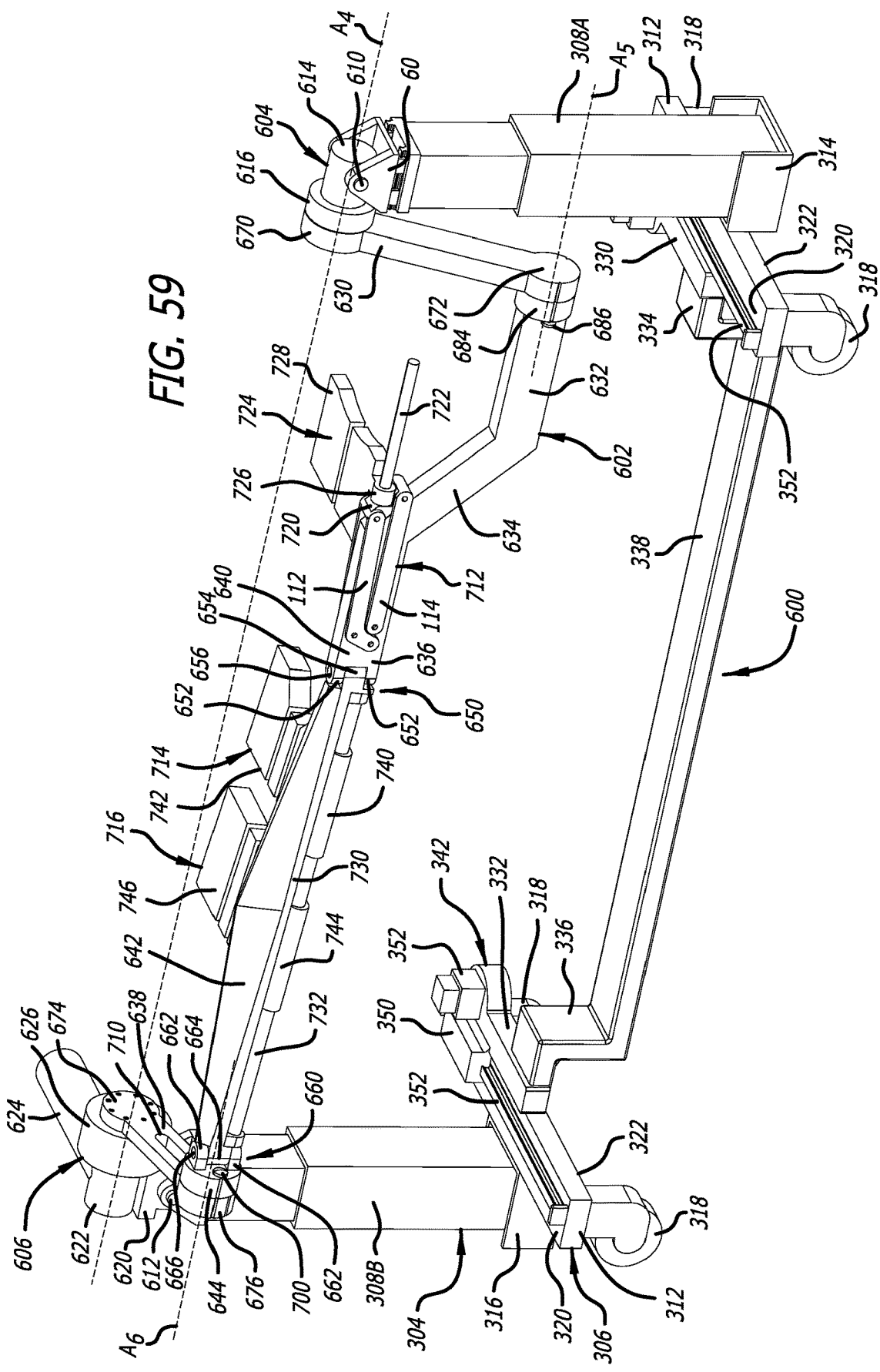
FIG. 59 is a top first side perspective view that illustrates a second embodiment of a surgical table being reconfigurable between a left configuration and a right configuration, where the surgical table is depicted in the left configuration.
Figure 60:
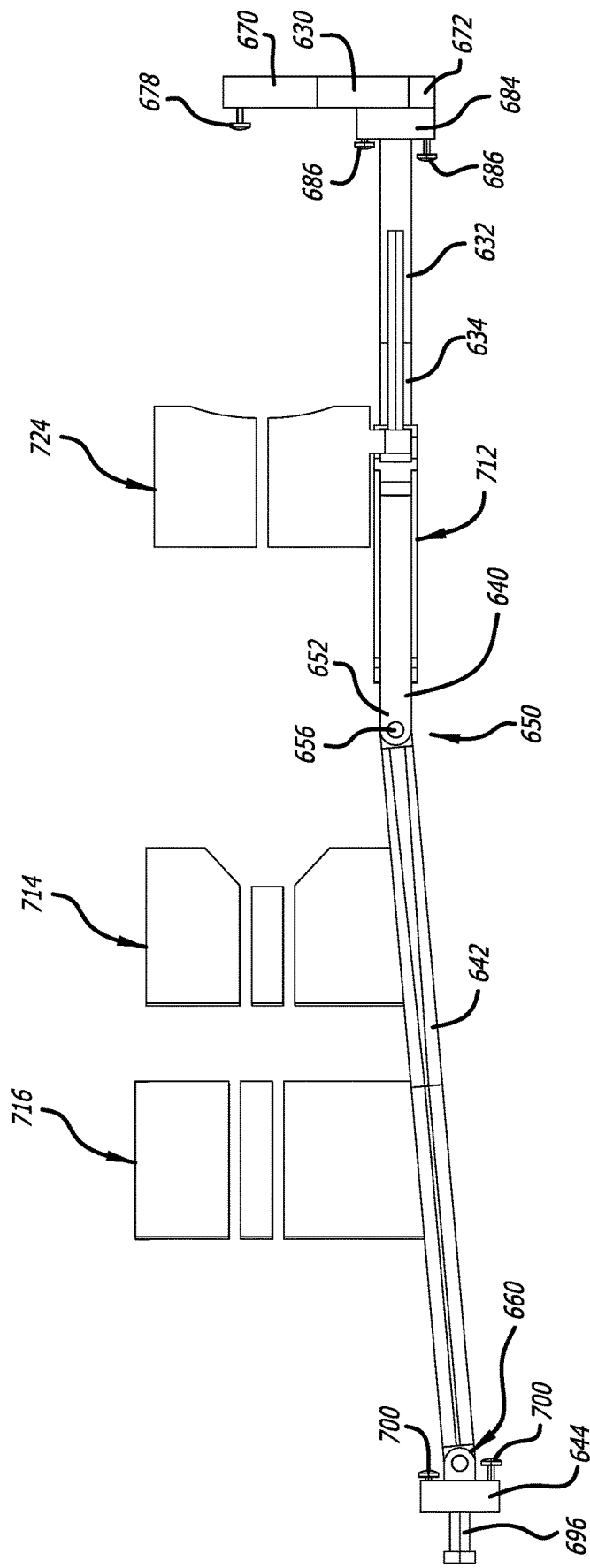
FIG. 60 is a top plan view that illustrates a portion of the surgical table of FIG. 59 depicting a portion of a main beam thereof in the left configuration and illustrating possible articulation thereof.
Figure 61:
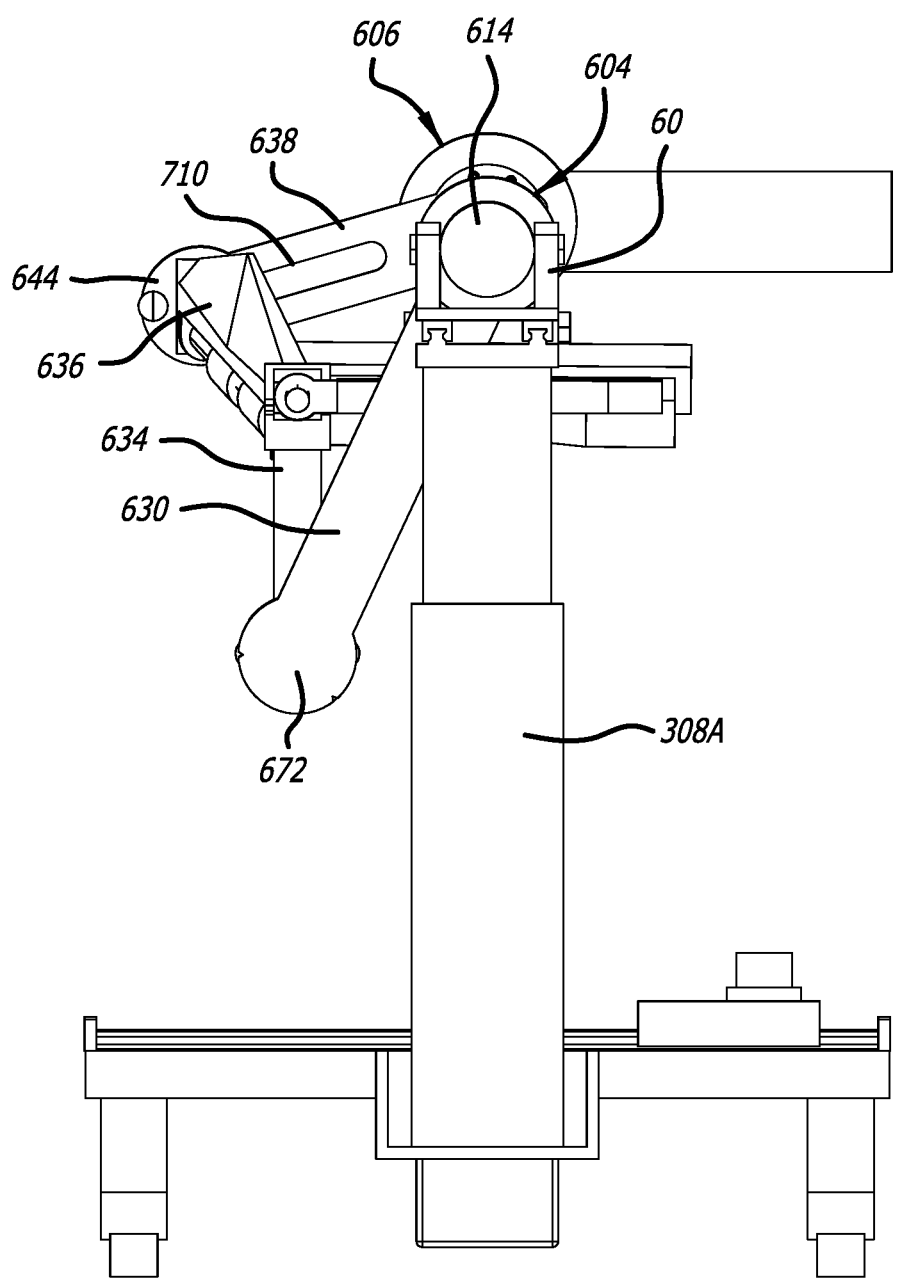
FIG. 61 is first end elevational view that illustrates the surgical table of FIG. 59 in the left configuration.
Figure 62:
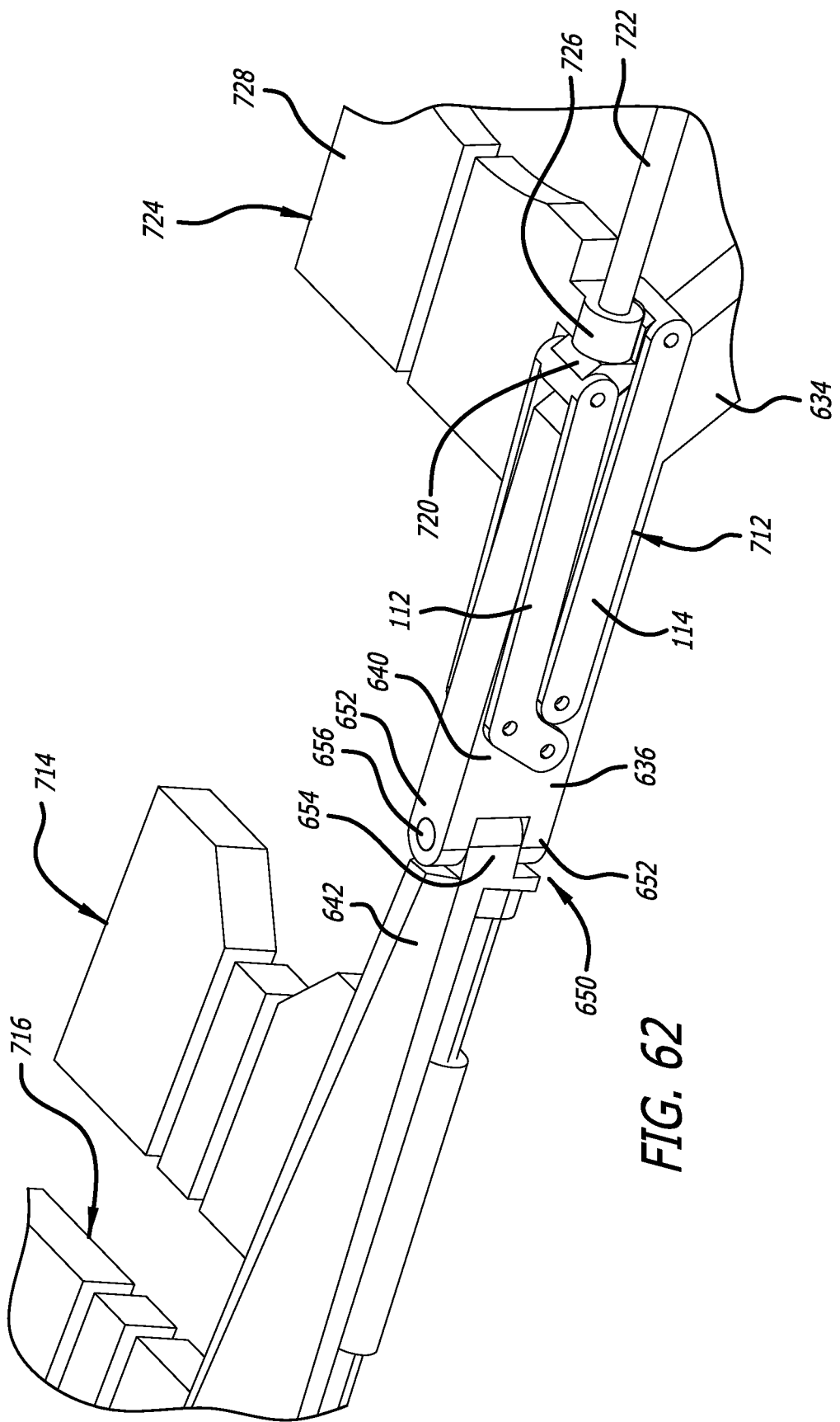
FIG. 62 is an enlarged top first side perspective view that illustrates a middle portion of the surgical table of FIG. 59 in the left configuration depicting a first articulable joint of the main beam.
Figure 63:
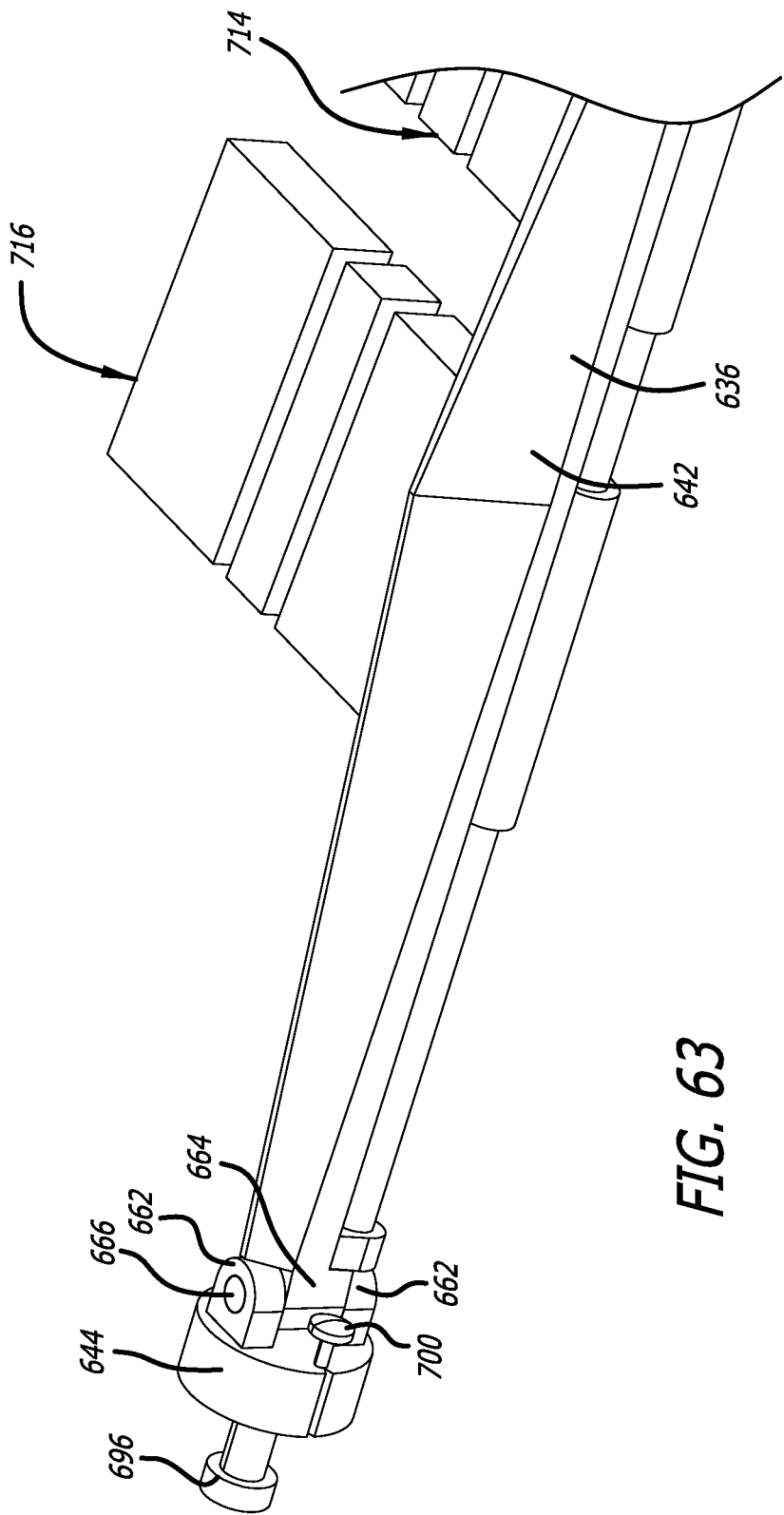
FIG. 63 is an enlarged top first side perspective view that illustrates another middle portion of the surgical table of FIG. 59 in the left configuration depicting a second articulable joint of the main beam.

As depicted in FIG. 59, for example, the surgical frame 600, like the surgical frames 300 and 400, includes the support structure 304 having the support platform 306 incorporating the translating beam 302. The support structure 304 of the surgical frame 600, like the surgical frames 300 and 400, also includes the first vertical support post 308A and the second vertical support post 308B. As such, the element numbering used to describe the surgical frames 300 and 400 is also applicable to portions of the surgical frame 600.

Unlike the surgical frame 300, the surgical frame includes an adjustable left-right main beam 602. The main beam 602 can be converted between a left configuration and a right configuration. The left configuration affords positioning of substantial portions of the main beam 602 adjacent the right side of the patient P to provide access to the left side of the patient. Furthermore, the right configuration affords positioning of substantial portions of the main beam 402 adjacent the left side of the patient P to provide access to the right side of the patient. In either of the left configuration or the right configuration, the main beam 602 affords positioning portions thereof in closer proximity to portions of the patient P than the main beam 402. The conversion between the left and right configurations allows the surgical frame 600 to be adapted to provide access to a surgical site on the left side or the right side of the patient P and/or be adapted to the preference of a surgeon.

The main beam 602 is supported at a first end by the first vertical support post 308A, the clevis 60, and a first coupler 604, and is supported at the second end by the second vertical support post 308B, the clevis 60, and a second coupler 606. The coupler 604 is pivotally attached to the clevis 60 at the first end via a pin 610, and the coupler 606 is pivotally attached to the clevis 60 at the second end via a pin 612.

As depicted in at least FIG. 59, the first coupler 604 includes a body portion 614 that is pinned to the clevis 60 with the pin 610, and a head portion 616 that is rotatable with respect to the body portion 614. Furthermore, the second coupler 606 includes a base portion 620 that is pinned to the clevis 60 with the pin 612, a body portion 622 that includes a transmission (not shown), a motor 624 that drives the transmission in the body portion 622, and a head portion 626 that is rotatable with respect to the body portion 622 and driven rotationally by the transmission via the motor 624. The head portion 616 is engageable to a portion of the main beam 602 and the head portion 626 is engageable to another portion of the main beam 602, and the rotatability of the head portions 616 and 626 define an axis of rotation $A_4$ (FIG. 59) of the main beam 602. The main beam 602 can be rotated using the motor 624 and the transmission interconnected with the motor 624. As such, the first coupler 604 and the second coupler 606 facilitate rotation of the main beam 602 and the patient P supported thereby.

As depicted in at least FIG. 59, the main beam 602 includes a first portion 630, a second portion 632, a third portion 634, a fourth portion 636, and a fifth portion 638. The first portion 630 is attached to the head portion 616, the fifth portion 638 is attached to the head portion 626, and the second portion 632, the third portion 634, and the fourth portion 636 can be formed as a elongated beam portion that extends between the first portion 630 and the fifth portion 638. As depicted in FIG. 59, the first portion 630 and the fifth portion 638 extend transversely to the axis of rotation $A_4$ and space the second portion 632, the third portion 634, and the fourth portion 636 apart from the axis of rotation $A_4$ of the main beam 602. As discussed above with respect to the surgical frames 10 and 400 and as depicted in FIG. 59, this offset affords positioning of the cranial-caudal axis of patient P approximately aligned with the axis of rotation $A_4$ of the offset main beam 602. Furthermore, the second portion 632 and the fourth portion 636 at the very least extend substantially parallel to the axis of rotation $A_4$, and the third portion 634 transitions between the second portion 632 and the fourth portion 636.

The second portion 632, the third portion 634, and portions the fourth portion 636 can be unitarily formed with another. Furthermore, the second portion 632 and the fourth portion 636 are attached to the first portion 630 and the fifth portion 638, respectively, to afford the reconfiguration of the main beam 602 between the left configuration and the right configuration. The left configuration of the main beam 602 is depicted in FIGS. 59-63, and the right configuration of the main beam 602 is depicted in FIGS. 71-74. Additionally, the fourth portion 636 includes a first section 640, a second section 642, and a third section 644 that are articulable with respect to one another. The first section 640 can be unitarily formed with the second portion 632 and the third portion 634, the first section 640 and second section 642 can be articulable with respect to one another, and the second section 642 and the third section 644 can be articulable with respect to one another.

The first section 640 and the second section 642 are joined by a first hinged connection 650, and the second section 642 and the third section 644 are joined by a second hinged connection 660. The first hinged connection 650, for example, employs two knuckles 652 formed on the first section 640, a knuckle 654 formed the second section 642, and a pin 656. To facilitate the connection afforded by the first hinged connection 650, the knuckle 654 is received between the knuckles 652, and the pin 656 is received through the knuckles 652 and the knuckle 654. Furthermore, the second hinged connection 660, for example, employs two knuckles 662 formed on the third section 644, a knuckle 664 formed on the second section 642, and a pin 666. To facilitate the connection afforded by the second hinged connection 660, the knuckle 664 is received between the knuckles 662, and the pin 666 is received through the knuckles 662 and the knuckle 654.

The first portion 630 includes a first end portion 670 and an opposite second end portion 672, and the fifth portion 638 includes a first end portion 674 and a second end portion 676. The first end portion 670 can be or include a flange that is attached to the head portion 616, and the second end portion 672 can be or include a flange that is attached to the second portion 632. Furthermore, the first end portion 674 can be or include a flange that is attached to the head portion 626, and the second end portion 676 can be or include a flange that is attached to the fourth portion 636. Rotation of the main beam 602 is possible because the head portion 616, and hence, the first portion 630 of the main beam 602 attached thereto are rotatable relative to the body portion 614, and because the head portion 626, and hence, the fifth portion 638 of the main beam 602 attached thereto are rotatable relative to the body portion 622. To facilitate conversion between the left configuration and the right configuration, the attachment of the first end portion 670 to the head portion 616, the attachment of the second end portion 672 to the second portion 632, the attachment of the second end portion 676 to the fourth portion 636 are adjustable.

The first portion 630 is rotatably adjustable between a first fixed position and a second fixed position relative to the head portion 616 to facilitate the left configuration and the right configuration, respectively, of the main beam 602. For example, one of the head portion 616 and the first end portion 670 of the first portion 630 can include an axle (not shown) that can be received in an aperture (not shown) formed in the other of the head portion 616 and the first end portion 670. As such, the first portion 630 can be rotatable relative to the head portion 616 between the first fixed position and the second fixed position, and a pin 678 can be received through portions of the head portion 616 and the first end portion 670 to facilitate fixation in the first fixed position and the second fixed position. Furthermore, indicia can be provided on the head portion 616 and the first end portion 670 indicating the first fixed position corresponding to the left configuration, and indicia can be provided on the head portion 616 and the first end portion 670 indicating the second fixed positon corresponding to the right configuration.

The second portion 632 is rotatably adjustable between a first fixed position and a second fixed position relative to the first portion 630 to facilitate the left configuration and the right configuration, respectively, of the main beam 602. For example, one of the second end portion 672 of the first portion 630 and a first end portion 684 of the second portion 632 (that can be or include a flange) can include an axle (not shown) that can be received in an aperture (not shown) formed in the other of the second end portion 672 of the first portion 630 and the first end portion 684 of the second portion 632. As such, the second portion 632 (as well as at least the third portion 634 and the fourth portion 636 attached thereto) can be rotatable relative to the first portion 630 between the first fixed position and the second fixed position, and pins 686 can be received through portions of the second end portion 672 and the first end portion 684 to facilitate fixation in the first fixed position and the second fixed position. Furthermore, indicia can be provided on the second end portion 672 and the first end portion 684 indicating the first fixed position corresponding to the left configuration, and indicia can be provided on the second end portion 672 and the first end portion 684 indicating the second fixed position corresponding to the right configuration.

The fourth portion 636 is adjustable between a first fixed position and a second fixed position relative to the fifth portion 638 to facilitate the left configuration and the right configuration, respectively, of the main beam 602. For example, one of the second end portion 676 of the fifth portion 638 and the third section 644 (that can be or include a flange) of the fourth portion 636 can include an axle (not shown) that can be received in an aperture (not shown) formed in the other of the second end portion 676 of the fifth portion 638 and the third section 644 of the fourth portion 636. As depicted in at least FIGS. 60, 63, 66, and 67, the third section 644 of the fourth portion 636 includes an axle 696, and the second end portion 676 of the fifth portion 638 includes an aperture 698 for receiving the axle 696. As such, the fourth portion 636 (as well as at least the second portion 632 and the third portion 634 attached thereto) can be rotatable relative to the fifth portion 638 between the first fixed position and the second fixed position, and pins 700 can be received through portions of the second end portion 676 and the third section 644 to facilitate fixation in the first fixed position and the second fixed position. Furthermore, indicia can be provided on the second end portion 676 and the third section 644 indicating the first fixed position corresponding to the left configuration, and indicia can be provided on the second end portion 676 and the third section 644 indicating the second fixed position corresponding to the right configuration.

Figure 69:
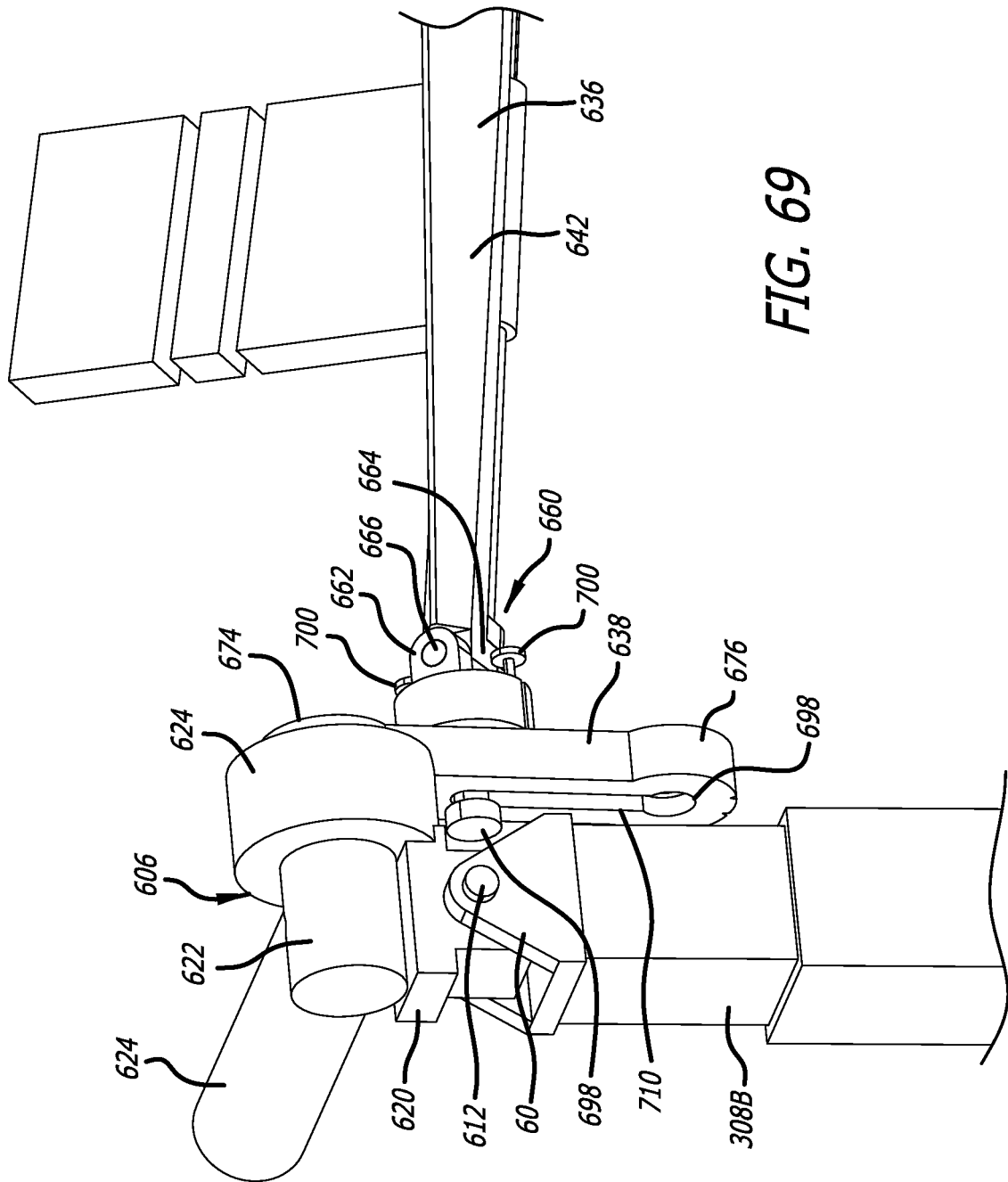
FIG. 69 is an enlarged top first side perspective view that illustrates an upper portion of the surgical table of FIG. 59 at and adjacent the second end depicting portions of the main beam thereof during the second portion of the reconfiguration process.
Figure 70:
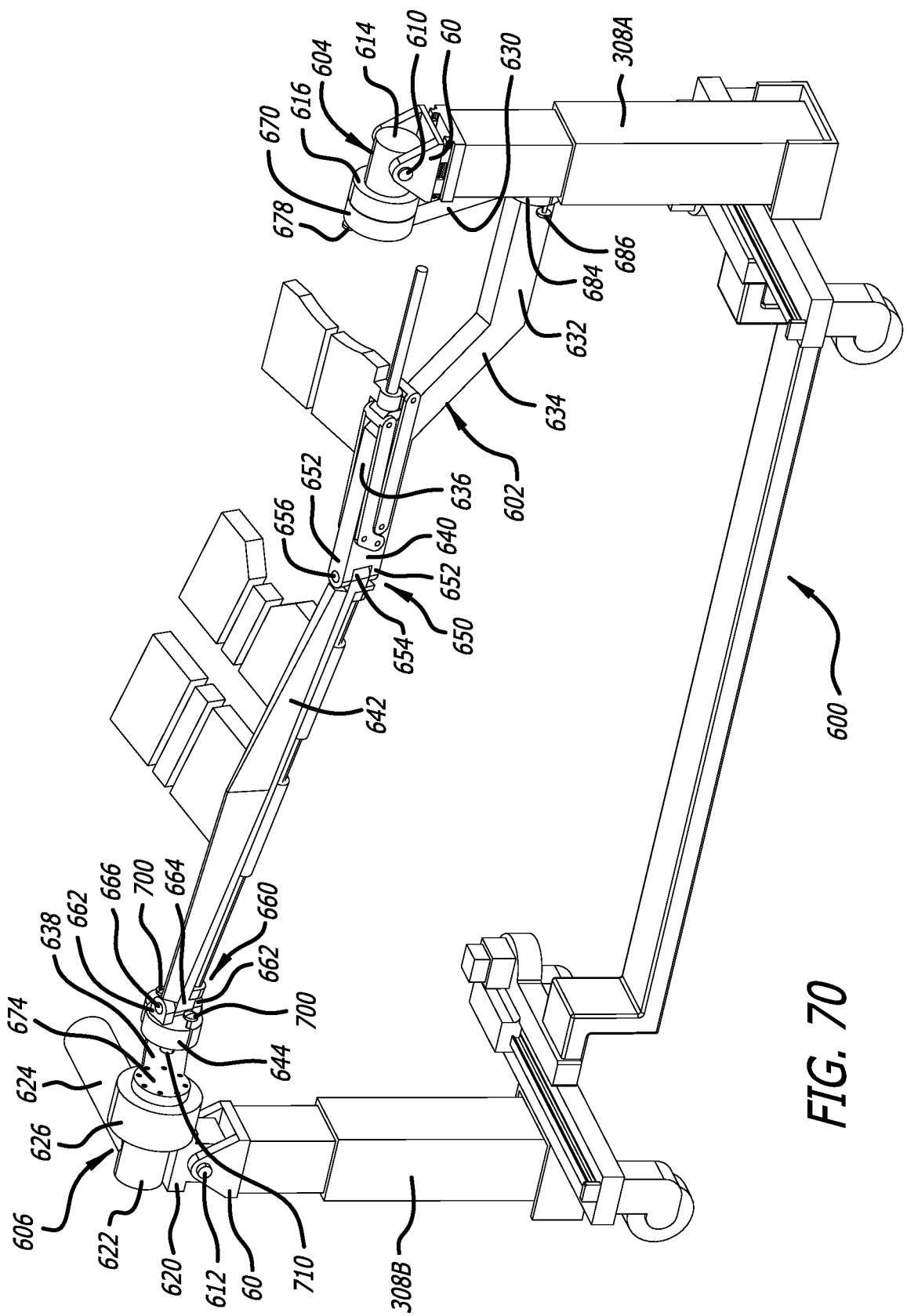
FIG. 70 is a top first side perspective view of the surgical table of FIG. 59 similar to FIGS. 64 and 68 that illustrates portions of the main beam thereof during the second portion of the reconfiguration process.

As depicted in in FIG. 59, the rotational adjustment of the second portion 632 relative to the first portion 630 occurs along an axis of rotation $A_5$, and rotational adjustment of the fourth portion 636 relative to the fifth portion 638 occurs along an axis of rotation $A_6$. The axes of rotation $A_5$ and $A_6$ are parallel, but not aligned, with one another. As such, the above-discussed adjustment between the first fixed positions and the second fixed positions potentially could lead to unwanted binding of the portions of the main beam 602 during reconfiguration from the left configuration to the right configuration, and vice versa. Such binding would interfere with the adjustment between the left configuration and the right configuration. To afford the adjustment between the left configuration and the right configuration, the fifth portion 638 includes an elongated slot 710 formed therein that communicates with the aperture 698, and the axle 696 is moveable between a first inward position and a second outward position with respect to the third section 644 of the fourth portion 646. When the axle 696 is in the first inward portion, the axle 696 is received in the aperture 698, and the when the axle 696 is in the second outward position, the axle 696 can be moved from the aperture 698 into and along the elongated slot 710. As depicted in FIG. 69, movement of the axle 696 along the elongated slot 710 affords reconfiguration from the left configuration to the right configuration, and vice versa, without the possibility of binding of the main beam 602 during such reconfiguration.

As depicted at in FIG. 59, the main beam 602 includes various support structures provided thereon for supporting the patient P. Like the main beam 602, these support structures are moveable between a left configuration for supporting the patient P when the main beam 602 is in the left configuration, and a right configuration for supporting the patient P when the main beam 602 is in the right configuration.

A torso support 712, an upper leg support 714, and a lower leg support 716 are provided on the main beam 602, and are moveable between the left configuration and the right configuration. As depicted in FIGS. 59-63, the torso support 712, the upper leg support 714, and the lower leg support 716 are in the left configuration, and as depicted in FIGS. 71-74, the torso support 712, the upper leg support 714, and the lower leg support 716 are in the right configuration.

The torso support 712 is supported on the main beam 602, and can be similar to and include various components of the torso-lift support 24. In particular, the torso support 712 includes the first links 112 and the second links 114. The first links 112 and the second links 114 are interconnected with one another by a plate 720, and a post 722 extends outwardly from the plate 720. In addition to a chest support 724, the post 722 also can support head supports (such as, for example, the head support 20), and arm supports (such as, for example, arm supports 22A and 22B). The chest support 724 includes a collar portion 726 and a support portion 728. The collar portion 726 is used to support the support portion 728 on the main beam 602, and the support portion 728 is used to support portions of the patient's chest thereon. To illustrate, the post 722 is received through the collar portion 726 to support the collar portion 726 thereon, and the support portion 728 extends outwardly from the collar portion 726. Using the interaction of the post 722 and the collar portion 726, the support portion 728 can be rotated between the left configuration and the right configuration thereof.

The upper leg support 714 and the lower leg support 716 also are supported on the main beam 602. The second section 642 of the fourth portion 636 of the main beam 602 includes a recess 730 extending along a substantial portion thereof, and a post 732 supported by the fourth portion 636 extending from one end of the recess 730 to the other end of the recess 730. The upper leg support 714 includes a collar portion 740 and a support portion 742, and the lower leg support 716 includes a collar portion 744 and a support portion 746. The collar portions 740 and 744 are used to support the support portions 742 and 746 on the post 732, respectively, and the support portion 742 is used to support the patent's upper legs and the support portion 746 is used to the support the patient's lower legs. To illustrate, the post 732 is received through the collar portions 740 and 744 to support the collar portions 740 and 744 thereon, and the support portions 742 and 746 extend outwardly from the collar portions 740 and 744. Using the interaction of the post 742 and the collar portions 740 and 744, the support portions 742 and 746 can be rotated between the left configuration and the right configuration.

Figure 64:
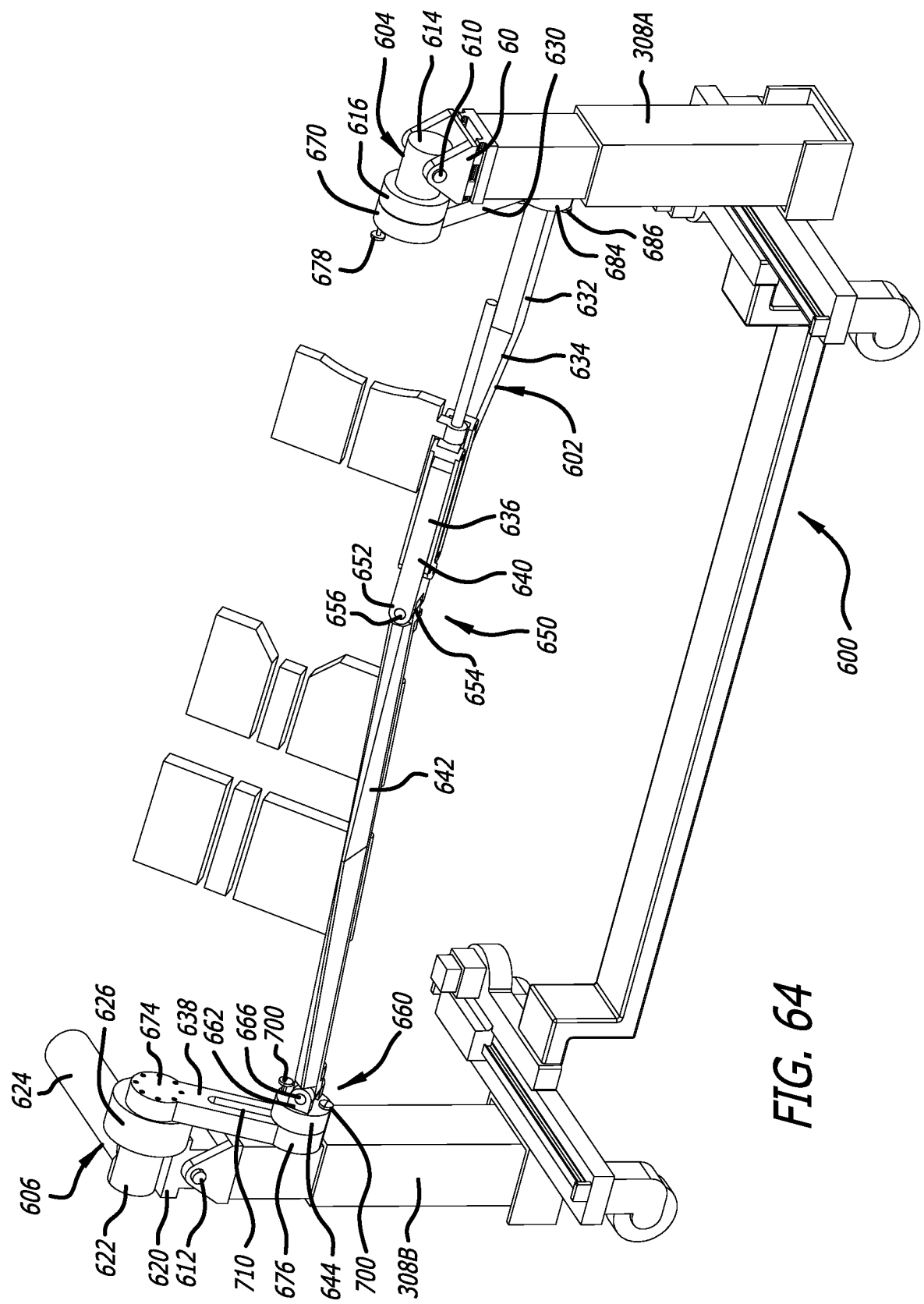
FIG. 64 is a top first side perspective view that illustrates the surgical table of FIG. 59 depicting portions of the main beam thereof during a first portion of the reconfiguration process from the left configuration to the right configuration.
Figure 65:
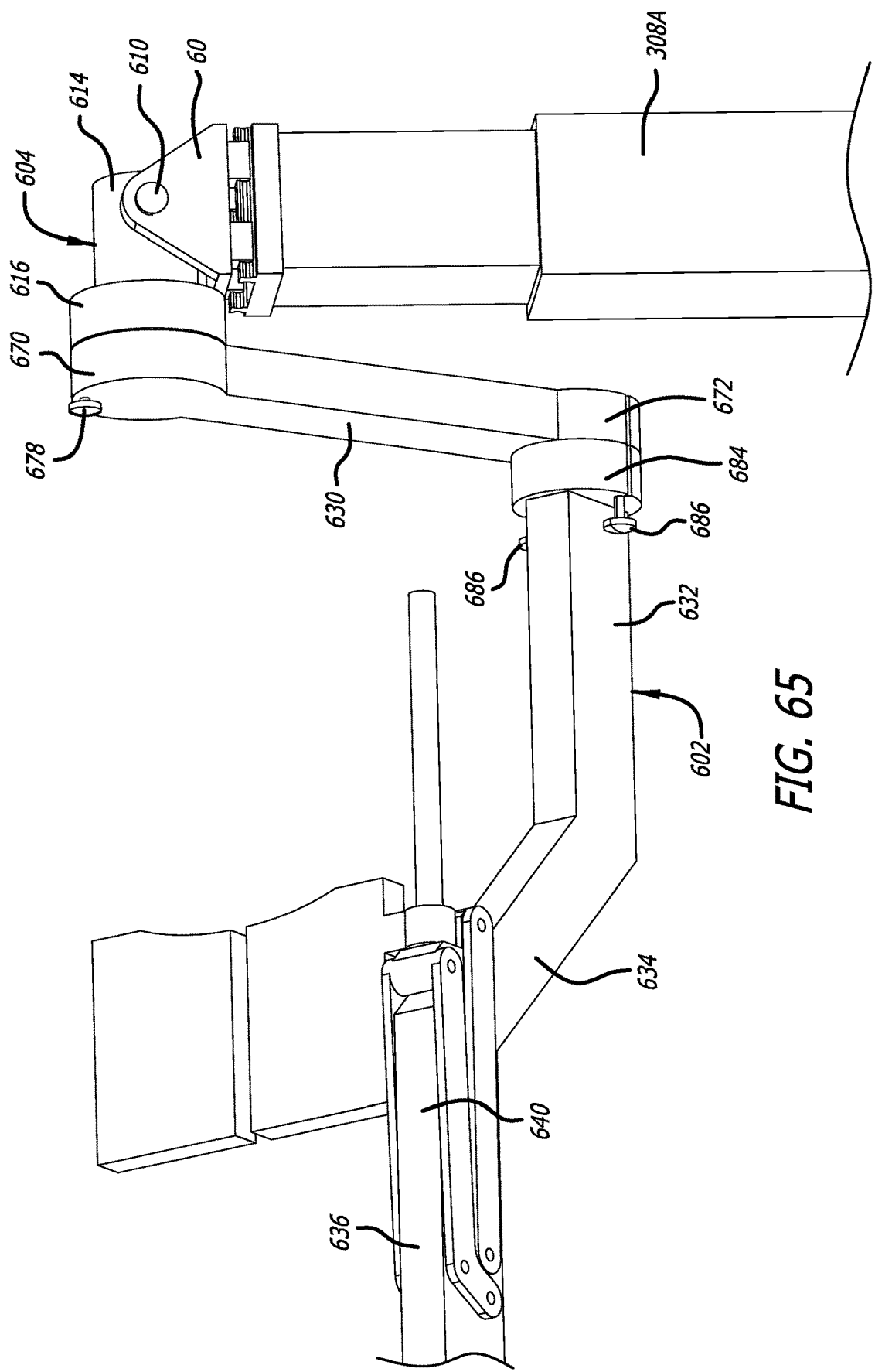
FIG. 65 is an enlarged top first side perspective view that illustrates an upper portion of the surgical table of FIG. 59 at and adjacent the first end depicting portions of the main beam thereof during a second portion of the reconfiguration process.
Figure 66:
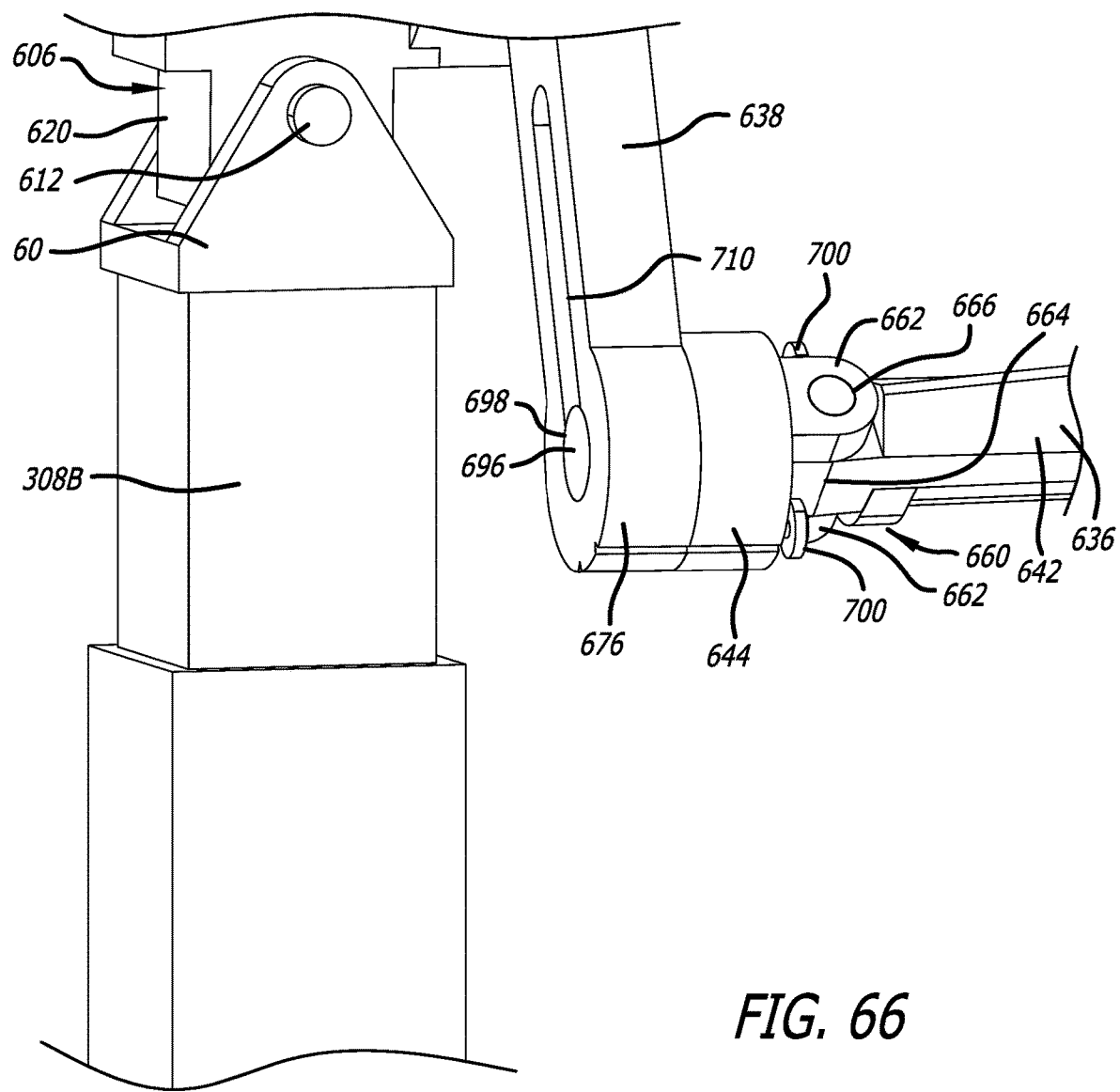
FIG. 66 is an enlarged top first side perspective view that illustrates an upper portion of the surgical table of FIG. 59 at and adjacent the second end depicting portions of the main beam thereof during the second portion of the reconfiguration process.
Figure 67:
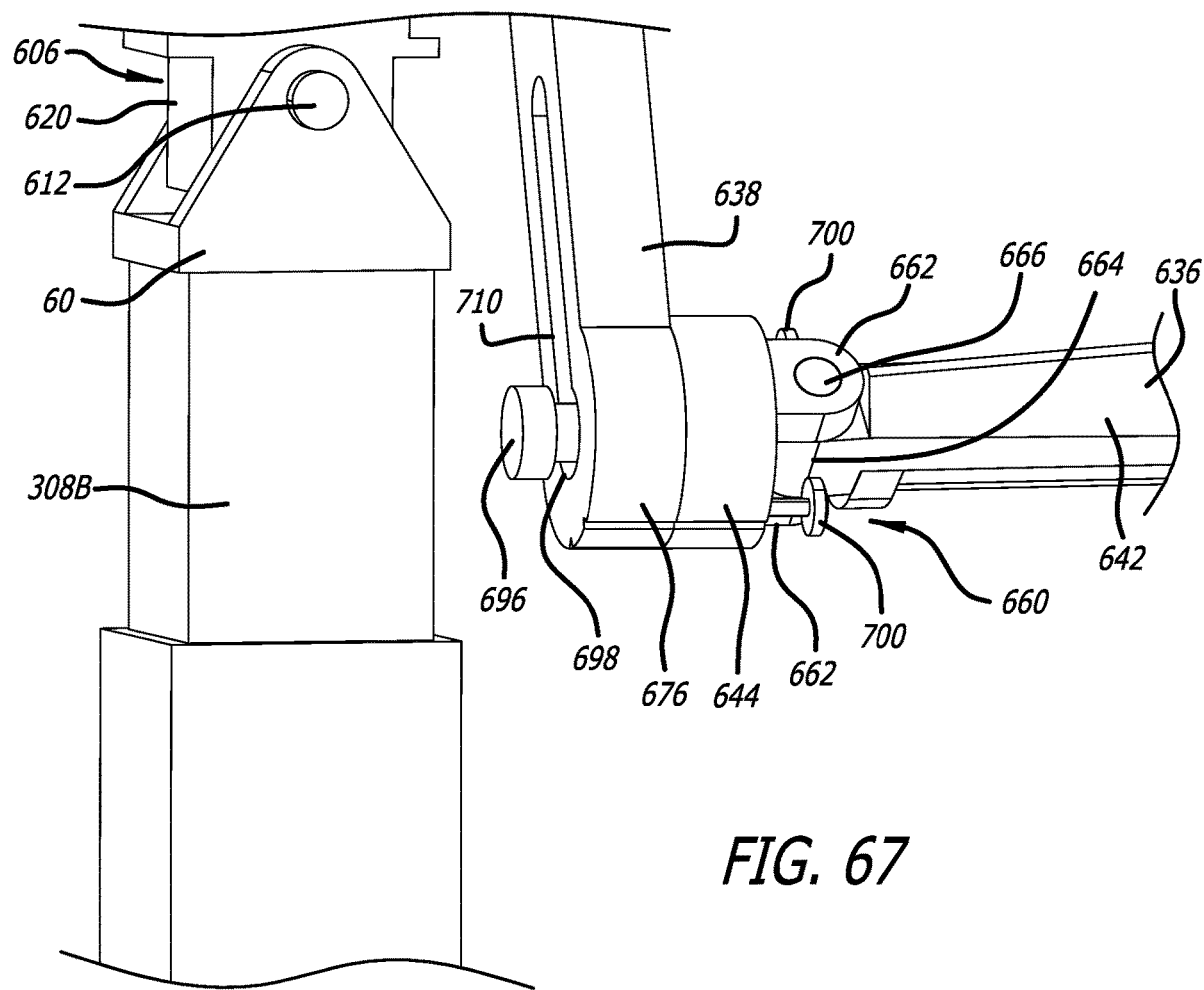
FIG. 67 is an enlarged top first side perspective view similar to FIG. 66 that illustrates an upper portion of the surgical table of FIG. 59 at and adjacent the second end depicting portions of the main beam thereof during the second portion of the reconfiguration process.
Figure 68:
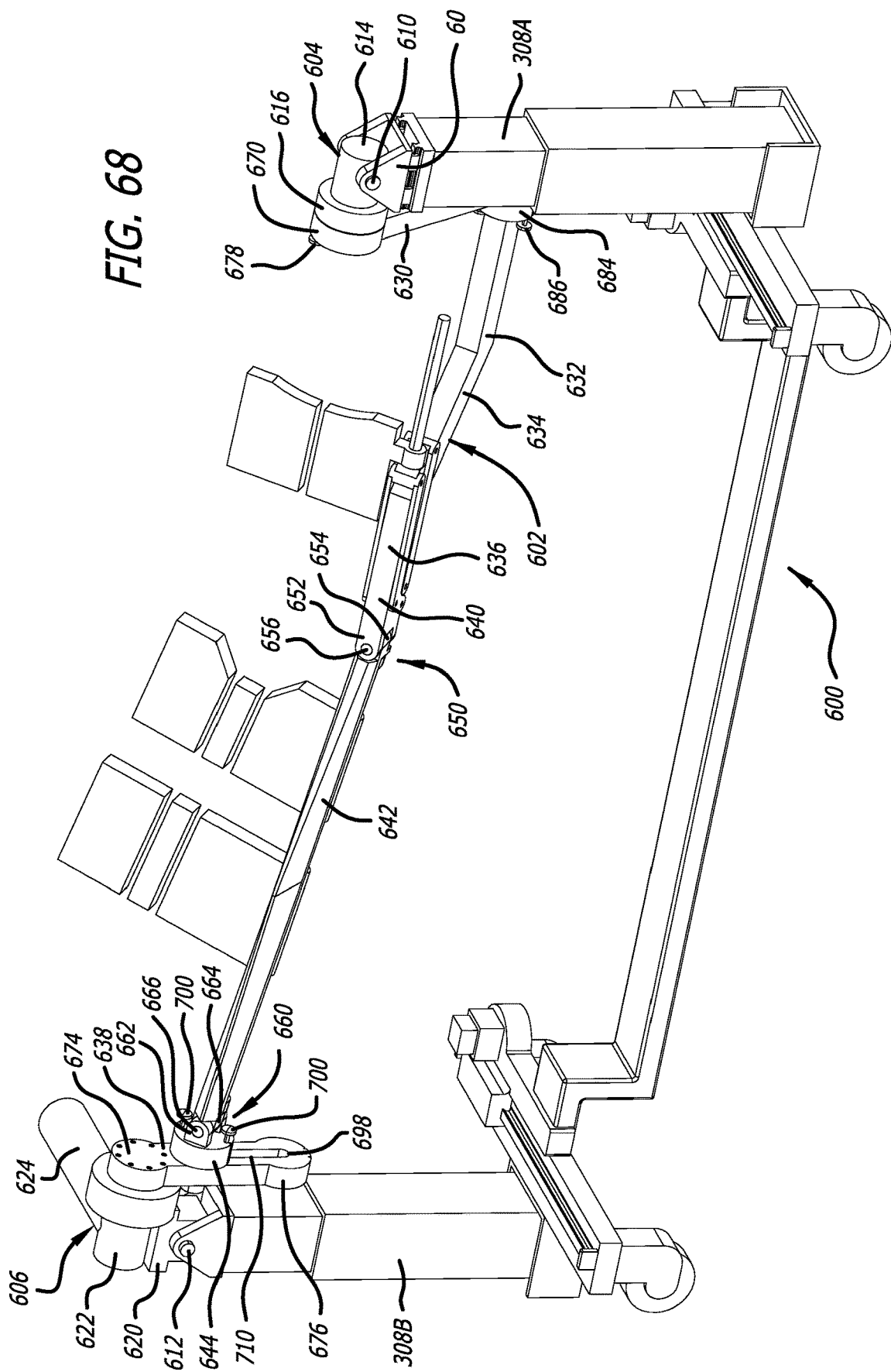
FIG. 68 is a top first side perspective view of the surgical table of FIG. 59 similar to FIG. 64 that illustrates portions of the main beam thereof during the second portion of the reconfiguration process.

To facilitate reconfiguration of the main beam 602 from the left configuration to the right configuration, the pin 678, as depicted in FIG. 64, is disengaged from the head portion 616, the first portion 630 is rotated relative to the head portion 616 from a position corresponding to the first fixed position to a position corresponding to the second fixed position, and the pin 678 is reengaged to the head portion 616 to hold the first end portion 670 in the second fixed position.

Next, as depicted in FIGS. 65-70, one of the pins 686 and one of the pins 700 are disengaged from the second end portion 672 of the first portion 630 and the second end portion 676 of the fifth portion 638, the axle 696 is moved from the first inward position to the second outward position, and the second portion 632, the third portion 634, and the fourth portion 636 are rotated to move the second portion 632 and the fourth portion 636 from positions corresponding to the first fixed positions thereof to positions corresponding to the second fixed positions thereof. The rotation of the second portion 632, the third portion 634, and the fourth portion 636 avoids the above-discussed binding of the main beam by causing the axle 696 to slide within the elongated slot 710 and the fifth portion 638 (and the head portion 626 attached thereto) to rotate.

Figure 71:
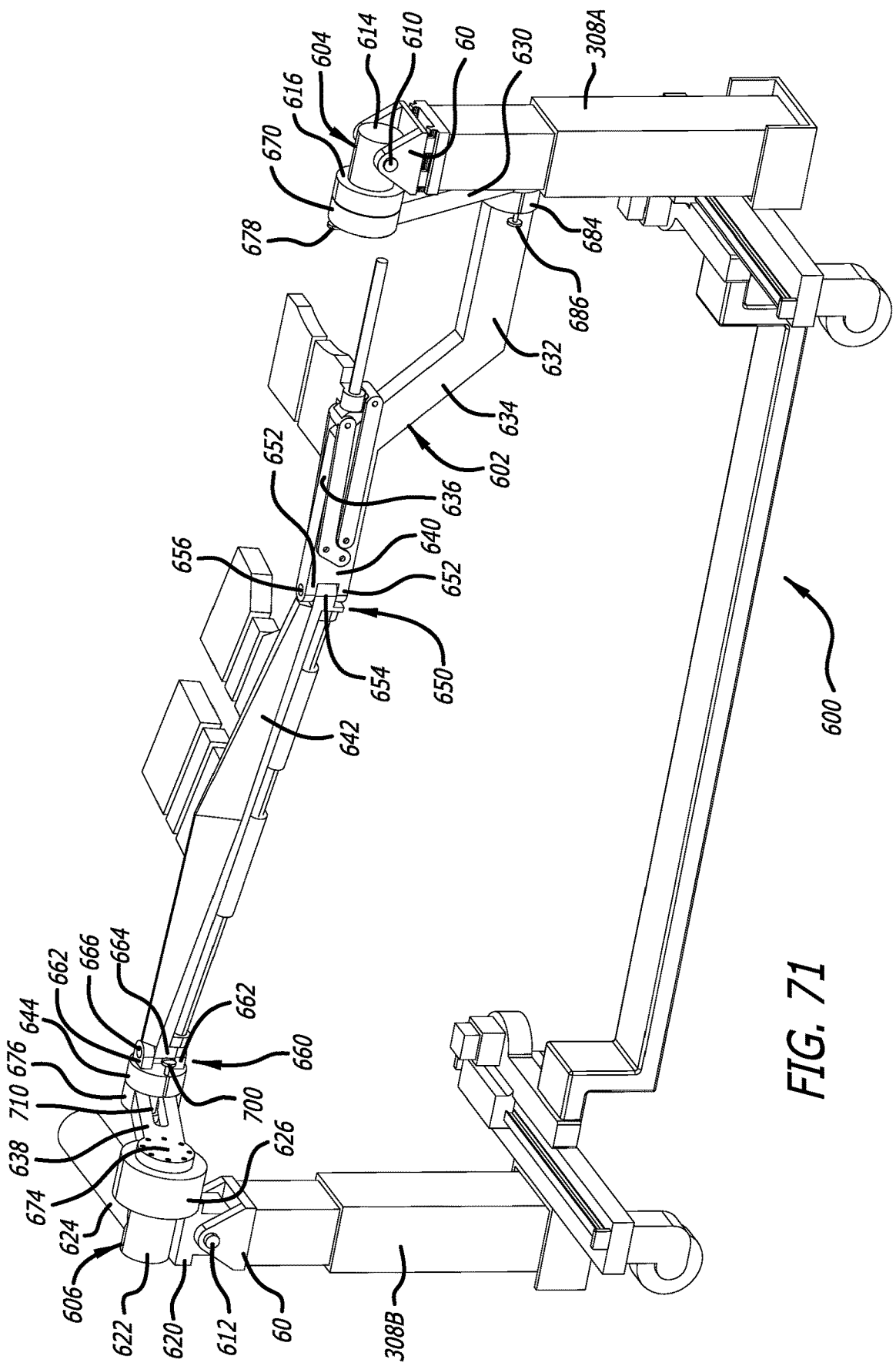
FIG. 71 is a top first side perspective view of the surgical table of FIG. 59 similar to FIGS. 64, 68, and 70 that illustrates portions of the main beam thereof during a third portion of the reconfiguration process.
Figure 72:
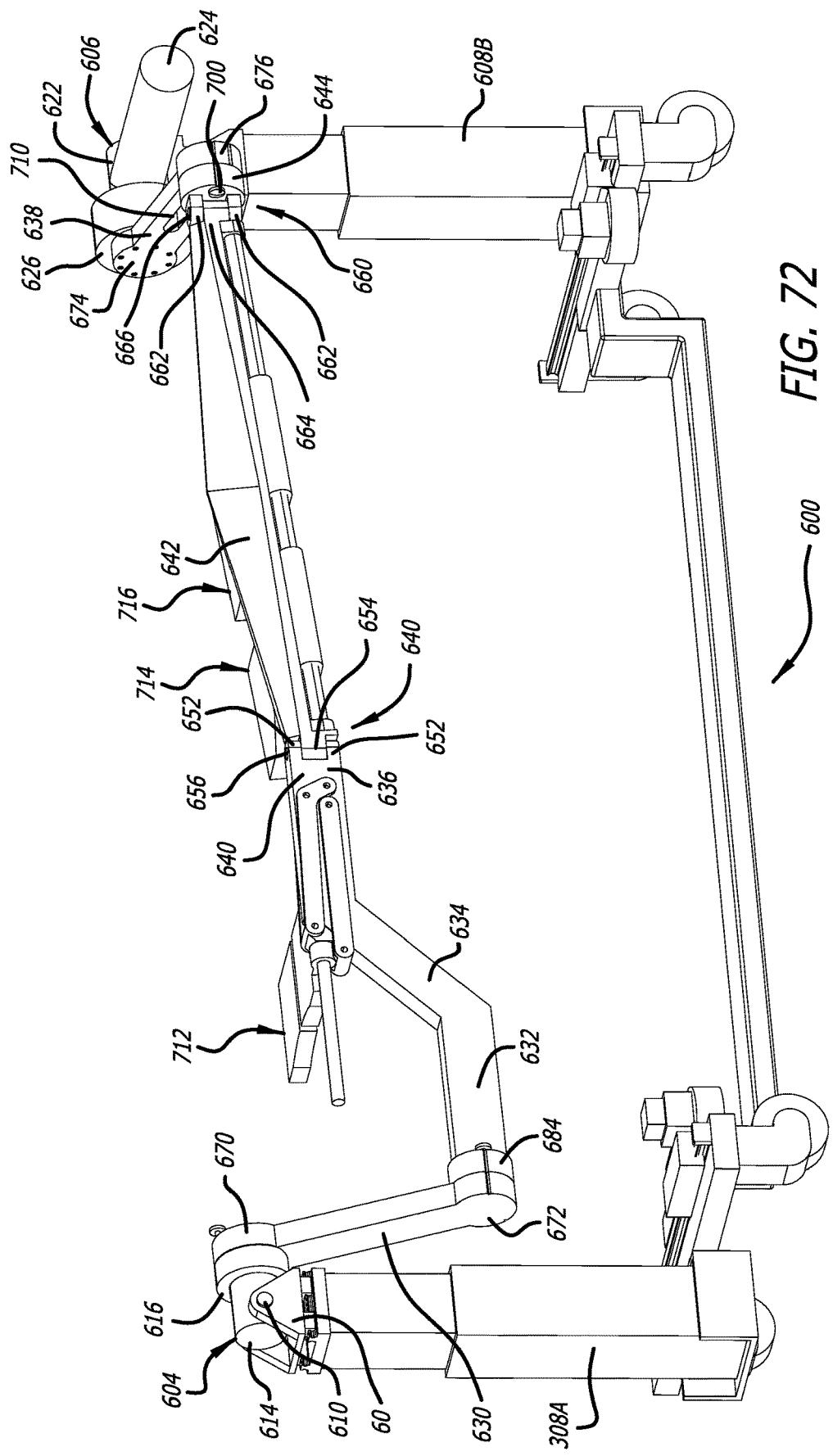
FIG. 72 is a top second side perspective view that illustrates the surgical table of FIG. 59 depicting portions of the main beam thereof in the right configuration after completion of the reconfiguration process.
Figure 73:
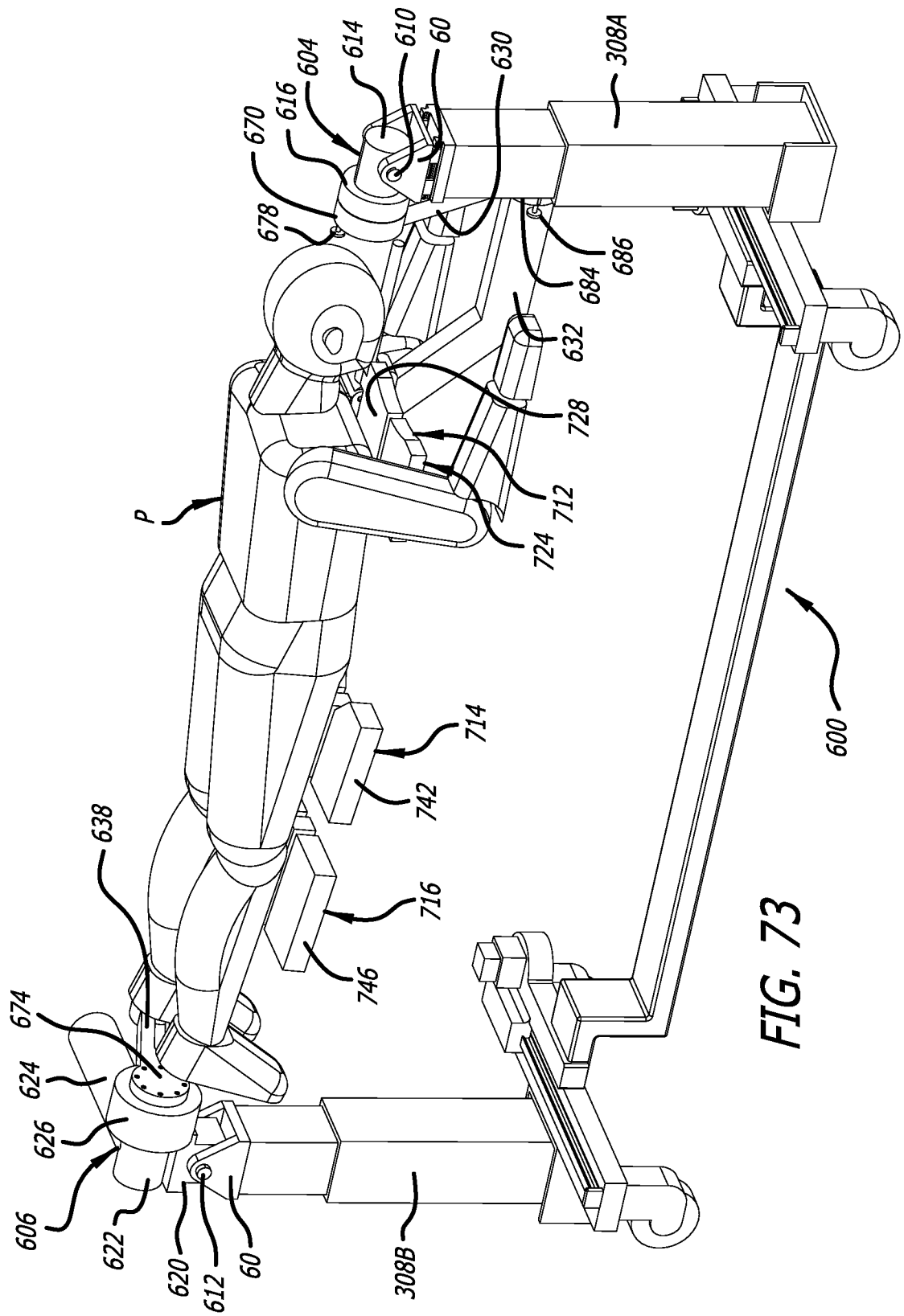
FIG. 73 is a top first side perspective view that illustrates the surgical table of FIG. 59 in the right configuration with the patient being supported on the main beam thereof in a prone position.
Figure 74:
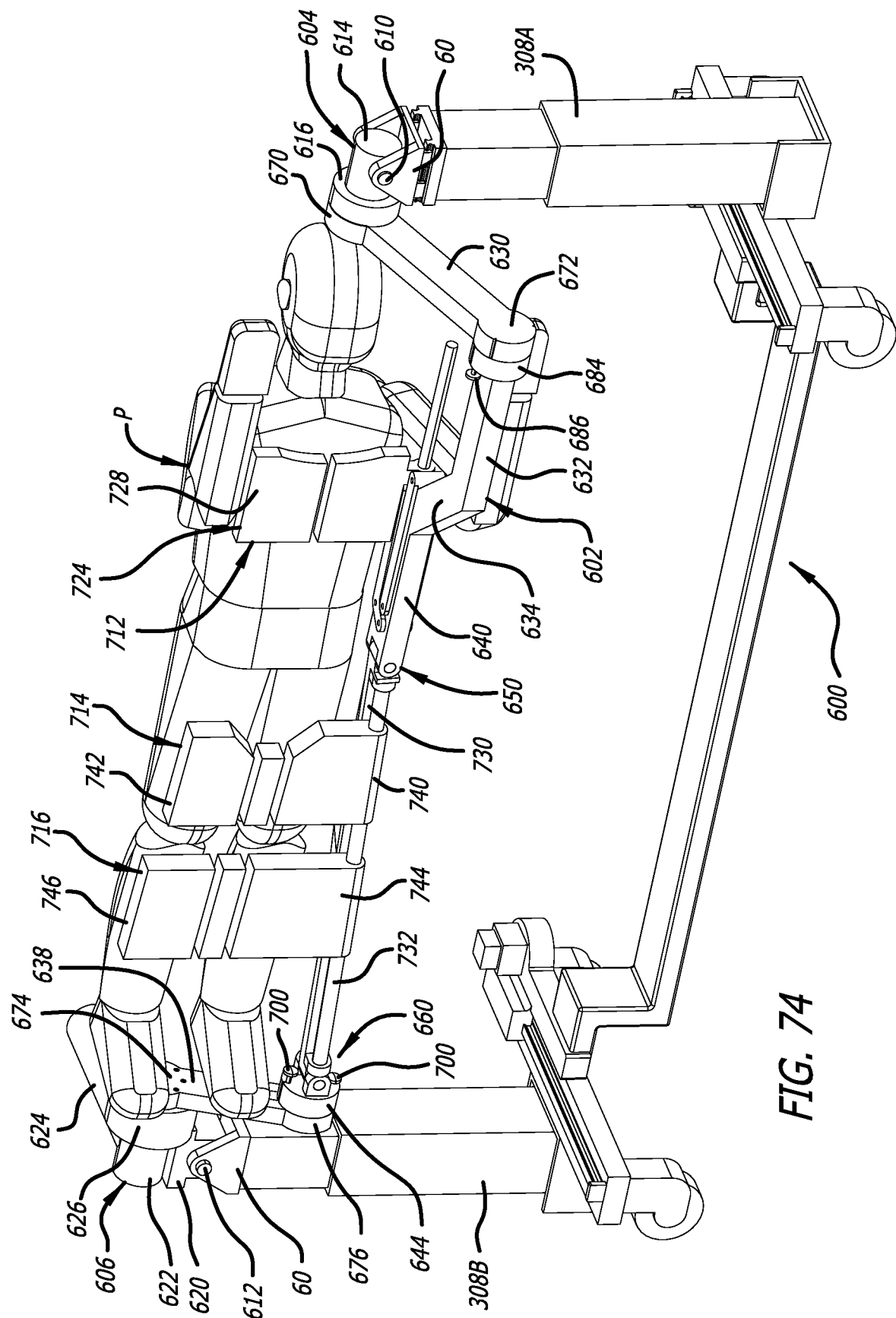
FIG. 74 is a top first side perspective view that illustrates the surgical table of FIG. 59 in the right configuration with the patient being supported on the main beam thereof in a lateral position.

Thereafter, as depicted in FIGS. 71 and 72, the other of the pins 686 and the other of the pins 700 are engaged to the second end portion 672 of the first portion 630 and the second end portion 676 of the fifth portion 638, respectively, the axle 696 is moved from the second outward position to the first inward position, and the torso support 712, the upper leg support 714, and the lower leg support 716 are moved from the left configuration to the right configuration thereof.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A positioning frame for supporting a patient being reconfigurable between a left configuration and a right configuration, the positioning frame comprising:
   a main beam having a first end, a second end, and a length extending between the first and second end, the main beam having an axis of rotation relative to a first portion and a second portion of the positioning frame, the main beam being rotatable about the axis of rotation between at least a first position and a second position, the main beam including a first main beam portion at the first end rotatably interconnected relative to the first portion of the positioning frame, a second main beam portion at the second end rotatably interconnected relative to the second portion of the positioning frame, and an elongated main beam portion extending between the first main beam portion and the second main beam portion,
   a first end of the elongated main beam portion being rotatably adjustable between a first fixed position and a second fixed position relative to the first main beam portion and a second end of the elongated main beam portion being rotatably adjustable between a first fixed position and a second fixed position relative to the second main beam portion;
   at least one patient support being moveably attached to the elongated main beam portion, the at least one patient support each being moveable between a first location on a first side of the elongated main beam portion and a second location on a second side of the elongated main beam portion; and
   wherein, when in the left configuration,
   the first end of the elongated main beam portion is in the first fixed position relative to the first main beam portion,
   the second end of the elongated main beam portion is in the first fixed position relative to the second main beam portion, and
   the at least one patient support is in the first location, the positioning frame is in the left configuration and is capable of supporting the patient to provide greater access to a left lateral side of the patient,
   wherein, when in the right configuration,
   the first end of the elongated main beam portion is in the second fixed position relative to the first main beam portion,
   the second end of the elongated main beam portion is in the second fixed position relative to the second main beam portion, and
   the at least one patient support is in the second location, the positioning frame is in the right configuration and is capable of supporting the patient to provide greater access to a right lateral side of the patient.

2. The positioning frame of claim 1, wherein the elongated main beam portion includes a first section extending from the first end toward the second end, a second section extending from the first section toward the second end, and a third section extending from the second section to the second end, the first section being rotatably adjustable with the first end of the elongated main beam between the first fixed position and the second fixed position thereof, the first section and the second section being pivotally attached to one another, the second section and the third section being pivotally attached to one another, and the third section being rotatably adjustable with the second end of the elongated main beam between the first fixed position and the second fixed position thereof.

3. The positioning frame of claim 2, wherein each of the first section, the second section, and the third section includes a first end and a second end, the first end of the first section being collocated with the first end of the elongated main beam portion, the second end of the first section and the first end of the second section being pivotally attached to one another, the second end of the second section and the first end of the third section being pivotally attached to one another, and the second end of the third section being collocated with the second end of the elongated main beam portion.

4. The positioning frame of claim 3, wherein portions of the second end of the first section and the first end of the second section form portions of a first clevis facilitating pivotal attachment of the first section and the second section, and portions of the second end of the second section and the first end of the third section form portions of a second clevis facilitating pivotal attachment of the second section and the third section.

5. The positioning frame of claim 1, wherein the first main beam portion and the second main beam portion extend transversely to the axis of rotation of the main beam, and the elongated main beam portion is offset from the axis of rotation by the first and second portions.

6. The positioning frame of claim 1, wherein the main beam is configured to support the patient in a prone position in the first position thereof, and is configured to support the patient in a lateral position in the second position thereof.

7. The positioning frame of claim 2, wherein rotatable adjustment of the first end of the elongated main beam portion between the first fixed position and the second fixed position thereof is about a second axis of rotation, and rotatable adjustment of the second end of the elongated main beam portion between the first fixed position and the second fixed position thereof is about a third axis of rotation, the second axis and the third axis of rotation being offset from the axis of rotation.

8. The positioning frame of claim 7, wherein the second axis of rotation and the third axis of rotation are offset from one another, one of the first section and the third section includes an axle, and one of the first main beam portion and the second main beam portion corresponding to the location of the axle includes a slot for receiving the axle, the slot affording repositioning of the axle therein to prevent binding of the elongated main beam portion relative to the first main beam portion and the second main beam portion as the first end of the elongated main beam portion is rotated between the first fixed position and the second fixed position thereof and the second end of the elongated main beam portion is rotated between the first fixed position and the second fixed position thereof.

9. A positioning frame for supporting a patient being reconfigurable between a left configuration and a right configuration, the positioning frame comprising:
   a main beam having a first end, a second end, and a length extending between the first and second end, the main beam having an axis of rotation relative to a first portion and a second portion of the positioning frame, the main beam being rotatable about the axis of rotation between at least a first position and a second position, the main beam including a first main beam portion at the first end rotatably interconnected relative to the first portion of the positioning frame, a second main beam portion at the second end rotatably interconnected relative to the second portion of the positioning frame, and an elongated main beam portion extending between the first main beam portion and the second main beam portion, the main beam being convertible between the left configuration and the right configuration, a first end of the elongated main beam portion being rotatably adjustable between a first fixed position and a second fixed position relative to the first main beam portion and a second end of the elongated main beam portion being rotatably adjustable between a first fixed position and a second fixed position relative to the second main beam portion;

at least one patient support being moveably attached to the elongated main beam portion, the at least one patient support each being moveable between a first location on a first side of the elongated main beam portion and a second location on a second side of the elongated main beam portion; and wherein, when in the left configuration, the patient is supported by the at least one patient support in an area defined by the first main beam portion, the second main beam portion, and the first side of the elongated main beam; and wherein, when in the right configuration, the patient is supported by the at least one patient support in an area defined by the first main beam portion, the second main beam portion, and the second side of the elongated main beam.

10. The positioning frame of claim 9, wherein the elongated main beam portion includes a first section extending from the first end toward the second end, a second section extending from the first section toward the second end, and a third section extending from the second section to the second end, the first section being rotatably adjustable with the first end of the elongated main beam between the first fixed position and the second fixed position thereof, the first section and the second section being pivotally attached to one another, the second section and the third section being pivotally attached to one another, and the third section being rotatably adjustable with the second end of the elongated main beam between the first fixed position and the second fixed position thereof.

11. The positioning frame of claim 10, wherein each of the first section, the second section, and the third section includes a first end and a second end, the first end of the first section being collocated with the first end of the elongated main beam portion, the second end of the first section and the first end of the second section being pivotally attached to one another, the second end of the second section and the first end of the third section being pivotally attached to one another, and the second end of the third section being collocated with the second end of the elongated main beam portion.

12. The positioning frame of claim 11, wherein portions of the second end of the first section and the first end of the second section form portions of a first clevis facilitating pivotal attachment of the first section and the second section, and portions of the second end of the second section and the first end of the third section form portions of a second clevis facilitating pivotal attachment of the second section and the third section.

13. The positioning frame of claim 9, wherein the first main beam portion and the second main beam portion extend transversely to the axis of rotation of the main beam, and the elongated main beam portion is offset from the axis of rotation by the first and second portions.

14. The positioning frame of claim 9, wherein the main beam is configured to support the patient in a prone position in the first position thereof, and is configured to support the patient in a lateral position in the second position thereof.

15. The positioning frame of claim 10, wherein rotatable adjustment of the first end of the elongated main beam portion between the first fixed position and the second fixed position thereof is about a second axis of rotation, and rotatable adjustment of the second end of the elongated main beam portion between the first fixed position and the second fixed position thereof is about a third axis of rotation, the second axis and the third axis of rotation being offset from the axis of rotation.

16. The positioning frame of claim 15, wherein the second axis of rotation and the third axis of rotation are offset from one another, one of the first section and the third section includes an axle, and one of the first main beam portion and the second main beam portion corresponding to the location of the axle includes a slot for receiving the axle, the slot affording repositioning of the axle therein to prevent binding of the elongated main beam portion relative to the first main beam portion and the second main beam portion as the first end of the elongated main beam portion is rotated between the first fixed position and the second fixed position thereof and the second end of the elongated main beam portion is rotated between the first fixed position and the second fixed position thereof.

17. A positioning frame for supporting a patient being reconfigurable between a left configuration and a right configuration, the positioning frame comprising:

a main beam having a first end, a second end, and a length extending between the first and second end, the main beam having an axis of rotation relative to a first portion and a second portion of the positioning frame, the main beam being rotatable about the axis of rotation between at least a first position and a second position, the main beam including a first main beam portion at the first end rotatably interconnected relative to the first portion of the positioning frame, a second main beam portion at the second end rotatably interconnected relative to the second portion of the positioning frame, and an elongated main beam portion extending between the first main beam portion and the second main beam portion, the main beam being convertible between the left configuration and the right configuration by rotatably adjusting the elongated main beam portion relative to the first main portion and the second main beam portion, at least one patient support being moveably attached to the elongated main beam portion, the at least one patient support being moveable between a first location on a first side of the elongated main beam portion and a second location on a second side of the elongated main beam portion; and wherein, when in the left configuration, the patient is supported by the at least one patient support in an area defined by the first main beam portion, the second main beam portion, and the first side of the elongated main beam; and wherein, when in the right configuration, the patient is supported by the at least one patient support in an area defined by the first main beam portion, the second main beam portion, and the second side of the elongated main beam.

18. The positioning frame of claim 17, wherein the first main beam portion and the second main beam portion extend transversely to the axis of rotation of the main beam, and the elongated main beam portion is offset from the axis of rotation by the first and second portions.

19. The positioning frame of claim 17, wherein rotatable adjustment of a first end of the elongated main beam portion between a first fixed position and a second fixed position relative to the first main beam portion, and rotatable adjustment of a second end of the elongated main beam portion between a first fixed position and a second fixed position relative to the second main beam serves in converting the main beam between the left configuration and the right configuration.

20. The positioning frame of claim 19, wherein the rotation of the first end of the elongated main beam is about a second axis of rotation and the rotation of the second of the elongated main beam is about a third axis of rotation, and wherein the second axis of rotation and the third axis of rotation are offset from one another.

\* \* \* \* \*